United States Patent
Jaminet et al.

(10) Patent No.: US 11,208,495 B2
(45) Date of Patent: Dec. 28, 2021

(54) ANTI-TM4SF1 ANTIBODIES AND METHODS OF USING SAME

(71) Applicant: ANGIEX, INC., Cambridge, MA (US)

(72) Inventors: Paul A. Jaminet, Cambridge, MA (US); Shou-Ching S. Jaminet, Cambridge, MA (US); Harold F. Dvorak, Newton Centre, MA (US); Leonard G. Presta, San Francisco, CA (US)

(73) Assignee: ANGIEX, INC., Cambridge, MA (US)

( * ) Notice: Subject to any disclaimer, the term of this patent is extended or adjusted under 35 U.S.C. 154(b) by 0 days.

(21) Appl. No.: 16/642,995

(22) PCT Filed: Aug. 28, 2018

(86) PCT No.: PCT/US2018/048402
§ 371 (c)(1),
(2) Date: Feb. 28, 2020

(87) PCT Pub. No.: WO2019/046338
PCT Pub. Date: Mar. 7, 2019

(65) Prior Publication Data
US 2020/0270360 A1    Aug. 27, 2020

Related U.S. Application Data

(60) Provisional application No. 62/550,994, filed on Aug. 28, 2017.

(51) Int. Cl.
| | | |
|---|---|---|
| *C07K 16/00* | (2006.01) | |
| *C07K 16/46* | (2006.01) | |
| *C07K 16/28* | (2006.01) | |
| *A61P 35/04* | (2006.01) | |
| *A61K 39/00* | (2006.01) | |

(52) U.S. Cl.
CPC .......... *C07K 16/2896* (2013.01); *A61P 35/04* (2018.01); *A61K 2039/505* (2013.01); *A61K 2039/545* (2013.01); *C07K 2317/24* (2013.01); *C07K 2317/33* (2013.01); *C07K 2317/565* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,500,362 A | 3/1996 | Robinson et al. |
| 5,530,101 A | 6/1996 | Queen et al. |
| 5,565,332 A | 10/1996 | Hoogenboom et al. |
| 5,585,089 A | 12/1996 | Queen et al. |
| 5,587,458 A | 12/1996 | King et al. |
| 5,693,761 A | 12/1997 | Queen et al. |
| 5,693,762 A | 12/1997 | Queen et al. |
| 5,821,337 A | 10/1998 | Carter et al. |
| 5,869,046 A | 2/1999 | Presta et al. |
| 6,180,370 B1 | 1/2001 | Queen et al. |
| 6,194,551 B1 | 2/2001 | Idusogie et al. |
| 6,982,321 B2 | 1/2006 | Winter |
| 7,087,409 B2 | 8/2006 | Barbas, III et al. |
| 7,527,791 B2 | 5/2009 | Adams et al. |
| 8,088,387 B2 | 1/2012 | Steeves et al. |
| 8,163,888 B2 | 4/2012 | Steeves et al. |
| 8,198,417 B2 | 6/2012 | Steeves et al. |
| 8,969,526 B2 | 3/2015 | Baehner et al. |
| 10,844,135 B2 | 11/2020 | Chari et al. |
| 2004/0214872 A1 | 10/2004 | Suto et al. |
| 2009/0136494 A1 | 5/2009 | Ponath et al. |
| 2014/0170140 A1 | 6/2014 | Bennett et al. |
| 2016/0229910 A1* | 8/2016 | Jaminet .................. A61P 27/02 |
| 2020/0268713 A1 | 8/2020 | Hutchinson et al. |

FOREIGN PATENT DOCUMENTS

| | | |
|---|---|---|
| EP | 0239400 B1 | 8/1994 |
| EP | 0592106 B1 | 11/2004 |
| EP | 0519596 B1 | 2/2005 |
| WO | WO-8807089 A1 | 9/1988 |
| WO | WO-9109967 A1 | 7/1991 |
| WO | WO-9951642 A1 | 10/1999 |
| WO | WO-2009100309 A3 | 12/2009 |
| WO | WO-2015054427 A1 | 4/2015 |

OTHER PUBLICATIONS

Lowenthal et al. Identification of novel N-glycosylation sites at non-canonical protein consensus motifs. J Proteome Res. Jul. 1, 2016; 15(7): 2087-2101. (Year: 2016).*
Valliere-Douglass et al. Asparagine-linked oligosaccharides present on a non-consensus amino acid sequence in the CH1 domain of human antibodies. J Biol Chem Nov. 20, 2009;284(47):32493-506. (Year: 2009).*
Brown et al. Tolerance of single, but not multiple, amino acid replacements in antibody VH CDR2: a means of minimizing B cell wastage from somatic hypermutation? J Immunol. May 1, 1996; 156(9):3285-91. (Year: 1996).*
Vajdos et al. Comprehensive functional maps of the antigen-binding site of an anti-ErbB2 antibody obtained with shotgun scanning mutagenesis . J. Mol. Biol. Jul. 5, 2002, 320(2):415-28. (Year: 2002).*
Sciuto et al., Intracellular distribution of TM4SF1 and internalization of TM4SF1-antibody complex in vascular endothelial cells Biochem Biophys Res Commun, vol. 465, pp. 338-343 (2015).

(Continued)

*Primary Examiner* — Maher M Haddad
(74) *Attorney, Agent, or Firm* — Wilson Sonsini Goodrich & Rosati

(57) ABSTRACT

Anti-TM4SF1 antibodies, and antigen-binding fragments thereof, are described that bind to an epitope on the ECL2 loop of human TM4SF1. Methods of use of said antibodies and fragments are also described, including for the inhibition of metastasis.

15 Claims, 13 Drawing Sheets
Specification includes a Sequence Listing.

(56) References Cited

OTHER PUBLICATIONS

Lin et al. TM4SF1: a new vascular therapeutic target in cancer, Angiogenesis vol. 17, pp. 897-907 (2014).

Visintin et al., Novel Anti-TM4SF1 Antibody-Drug Conjugates with Activity against Tumor Cells and Tumor Vasculature Mol Cancer Ther, vol. 14, No. 8, pp. 1868-1876 (2015).

Edwards, C P , et al., "Cloning of the Murine Counterpart of the Tumor-Associated Antigen H--6: Epitope Mapping of the Human and Murine L6 Antigens", Biochemistry, Vo. 34, Jan. 1, 1995, pp. 12653-12660.

"Extended European search Report for corresponding EP Application No. 18849908.1 dated Apr. 28, 2021".

"Fell, H P , et al., "Chimeric L6 antitumor antibody", Journal of Biological Chemistry, American Society for Biochemistry and Molecular Biology, vo. 267, No. 22, Aug. 5, 1992, pp. 15552-15558".

"Hellstrom, I et al., "Antitumor effects of L6, and IgG2a antibody that reacts with most human carcinomas", Proceedings of the National Academy of Sciences, National Academy of Sciences, US, Vo. 83, No. 18, Sep. 1, 1986, pp. 7059-7063".

"Hellstrom, I, et al. "Monoclonal Mouse Antibodies Raised Against Human Lung Carcinoma", Cancer Research, Vo. 46, No. 8, Aug. 1, 1986, pp. 3917-3923".

"Liu, A Y et al., "Chimeric Mouse-Human IGG1 Antibody That can Mediate Lysis of Cancer Cells" Proceedings of the National Academy of Sciences, National Academy of Sciences, US, vol. 84, May 1, 1987, pp. 3439-3443".

"Markens, John S, et al., "Membrane Topology of the L6 Antigen an identification of the Protein Epitope Recognized by the L6 Monoclonal Antibody" INC the Journal of Biological Chemistry, vo. 269, No. 10, Mar. 11, 1994, pp. 7397-7401".

"Stenzel-Johnson, P R, et al., "Identification of Residues in the Monoclonal Antitumor Antibody L6 Important for Binding to its Tumor Antigen", Biochemistry, Vo. 33, Jan. 1, 1994, p. 14400-14406".

* cited by examiner

FIG. 5

FR1-CDR1-FR2-CDR2-FR3-CDR3-FR4

VL

DVLMTQTPLSLPVRLGDQASISCRSSQTLVHSNGNTYLEWYLQKPGQSPKLLIYKVSNRLSGVPDRFSGSGSGTDF
TLKISRVETEDLGVYYCFQGSHGPWTFGGGTKLEIK

VH

QIQLVQSGPELKKPGETVKISCKASGYSFRDYGMNWVKQAPGRTFKWMGWINTYTGAPVYAADFKGRFAFSLDTSA
SAAFLQINNLKNEDTATYFCARWVSYGNNRNWFFDFWGAGTTVTVSS

FIG. 6

FR1-<u>CDR1</u>-FR2-<u>CDR2</u>-FR3-<u>CDR3</u>-FR4

VL: DIVMSQSPSSLAVSAGEKVTMSC<u>KSSQSLLNSRTRKNYLA</u>WYQQKPGQSPKLLIY<u>WASTRES</u>GVPDRFTGSGSGTD FTLTISNVQAEDLTVYYC<u>KQSYNPPWT</u>FGGGTKLEIK

VH: EVQLQQSGPELVKPGASVKISCKTSG<u>YTFTDYTMH</u>WVRQSHGKSLEWIG<u>GSFNPNPNNGLTNYNQKFKG</u>KATLTVDKS SSTVYMDLRSLTSEDSAVYYCTR<u>IRATGFDS</u>WGQGTTLTVSS

FIG. 7

FR1 - <u>CDR1</u> - FR2 - <u>CDR2</u> - FR3 - <u>CDR3</u> - FR4

VL: DIQMTQSPASLSASVGETVTITC<u>RTSKNIFNFLA</u>WYHQKQGRSPRLLVS<u>HTKTLAA</u>GVPSRFSGSGSGTQFSLKINSLQPEDFGIYYC<u>QHHYGTPWT</u>FGGGTKLEIK

VH: EVQVQQSGPELVKPGASVKMSCKASGYTFT<u>SYVMH</u>WVKQKPGQGLEWIG<u>YINPNNDNINYNEKFKG</u>KASLTSDKSSNTVYMELSSLTSEDSAVYYCAG<u>YGNSGANW</u>GQGTLVTVSA

FIG. 8

FR1-CDR1-FR2-CDR2-FR3-CDR3-FR4

VL
QIILSQSPAILSASPGEKVTMTCRANSGISFINWYQQKPGSSPKPWIYGTANLASGVPARFGGSGSGTSYSLTISR
VEAEDAATYYCQQWSSNPLTFGAGTKLELR

VH
QIQLVQSGPELKKPGETVKISCKASGYTFTNYGVKWVKQAPGKDLKWMGWINTYTGNPIYAADFKGRFAFSLETS
ASTAFLQINNLKNEDTATYFCVRFQYGDYRYFDVWGAGTTVTVSS

FIG. 9

FR1 - CDR1 - FR2 - CDR2 - FR3 - CDR3 - FR4

VL  DIQMTQSPASLSASVGEPVTITCRASKNIYTYLAWYHQKQGKSPQFLVYNARTLAGGVPSRLSGSGSVTQFSLNINTLH
REDLGTYFCQHHYDTPYTFGGGTNLEIK

VH  EVQLQQSGPELVKPGASVKLSCKASGYTVTSYVMHWVKQKPGQGLEWIGYINPYSDVTNCNEKFKGKATLTSDKTSSTA
YMELSSLTSEDSAVYYCSSYGGGFAYWGQGTLVTVSA

FIG. 10

FR1-CDR1-FR2-CDR2-FR3-CDR3-FR4

VL  DIQMTQSPASLSASVGETVTITCRASKNVYSYLAWFQQKQGKSPQLLVYNAKTLAEGVPSRFSGGGSGTQFSLKINSL
QPADFGSYYCQHHYNIPFTFGSGTKLEIK

VH  EVQLQQSGPELVKPGASVKMSCKASGYTFSSYVMHWVKQKPGQGLEWIGYINPYSDVTNYNEKFKGKATLTSDRSSN
TAYMELSSLTSEDSAVYYCARNYFDWGRGTLVTVSA

FIG. 11

FR1-CDR1-FR2-CDR2-FR3-CDR3-FR4

VL  DIVLTQSPASLAASLGQRATTSYRASKSVSTSGYSYMHWNQQKPGQPPRLLIYLVSNLESGVPARFSGSGSGTDFTLNIH
PVEEEDAATYYCQHIRELTTFGGGTKLEIK

VH  QIQLVQSGPELKKPGETVKISCKASGFTFTNYPMHWVKQAPGKGLKWMGWINTYSGVPTYADDFKGRFAFSLETSASTAY
LQINNLKNEDMATYFCARGGYDGSREFAYWGQGTLVTVS

ANTI-TM4SF1 ANTIBODIES AND METHODS OF USING SAME

CROSS-REFERENCE

This application is a U.S. National Stage Entry of PCT/US2018/048402, filed Aug. 28, 2018, which claims the benefit of U.S. Provisional Application No. 62/550,994 filed Aug. 28, 2017, each incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 28, 2018, is named 52628-703_601_SL.txt and is 105,071 bytes in size.

BACKGROUND

A therapy that can block attachment of tumor cells to endothelial cells and/or prevent migration of tumor cells across the endothelial monolayer, also referred to as transendothelial migration, can inhibit or prevent tumor metastasis. There remains a need in the art for cancer therapeutics, and in particular therapeutics that can prevent metastasis.

SUMMARY OF THE INVENTION

Provided herein in one embodiment is an anti-TM4SF1 binding protein comprising a heavy chain variable domain comprising a CDR3 domain comprising an amino acid sequence that has at least 75% identity to SEQ ID NO: 8, 20, 32, 44, 56, 68, or 80, 96, 118, 119, 120, or 121; a CDR2 domain comprising an amino acid sequence that has at least 75% identity to SEQ ID NO: 7, 19, 31, 43, 55, 67, 79, 95, 116, or 117; and a CDR1 domain comprising an amino acid sequence that has at least 75% identity to SEQ ID NO: 6, 18, 30, 42, 54, 66, 78, 94, or 115; and a light chain variable domain comprising a CDR3 domain comprising an amino acid sequence that has at least 75% identity to SEQ ID NO: 14, 26, 38, 50, 62, 74, 86, 110, or 129; a CDR2 domain comprising an amino acid sequence that has at least 75% identity to SEQ ID NO: 13, 25, 37, 49, 61, 73, 85, or 109, or 128; and a CDR1 comprising an amino acid sequence that has at least 75% identity to SEQ ID NO: 12, 24, 36, 48, 60, 72, or 84, 107, 108, 124, 125, 126, or 127. In some embodiments, the anti-TM4SF1 binding protein comprises: a heavy chain variable domain comprising a CDR3 domain comprising an amino acid sequence as set forth in SEQ ID NO: 8, 20, 32, 44, 56, 68, 80, 96, 118, 119, 120, or 121; a CDR2 domain comprising an amino acid sequence as set forth in SEQ ID NO: 7, 19, 31, 43, 55, 67, 79, 95, 116, or 117; and a CDR1 domain comprising an amino acid sequence as set forth in SEQ ID NO: 6, 18, 30, 42, 54, 66, 78, 94, or 115; and a light chain variable domain comprising a CDR3 domain comprising an amino acid sequence as set forth in SEQ ID NO: 14, 26, 38, 50, 62, 74, 86, 110, or 129; a CDR2 domain comprising an amino acid sequence as set forth in SEQ ID NO: 13, 25, 37, 49, 61, 73, 85, 109, or 128; and a CDR1 domain comprising an amino acid sequence as set forth in SEQ ID NO: 12, 24, 36, 48, 60, 72, or 84, 107, 108, 124, 125, 126, or 127. In some embodiments, the anti-TM4SF1 binding protein comprises: a heavy chain variable domain comprising an amino acid sequence that has at least 75% identity to SEQ ID NO: 3, 15, 27, 39, 51, 63, 75, 90, 92, 112, or 114, and a variable light chain comprising an amino acid sequence that has at least 75% identity to SEQ ID NO: 9, 21, 33, 45, 57, 69, 81, 97, 99, 101 or 122. In some embodiments, the anti-TM4SF1 binding protein comprises: a heavy chain variable domain comprising a sequence as set forth in SEQ ID NO: 3, 15, 27, 39, 51, 63, 75, 90, 92, 112, or 114, and a variable light chain comprising a sequence as set forth in SEQ ID NO: 9, 21, 33, 45, 57, 69, 81, 97, 99, 101, or 122. In some embodiments, the anti-TM4SF1 binding protein binds to an epitope on the ECL2 loop of human TM4SF1 with a $K_D$ of about $5 \times 10^{-8}$ M or less. In some embodiments, the anti-TM4SF1 binding protein binds to an epitope on the ECL2 loop of human TM4SF1 with a $K_D$ about $5 \times 10^{-8}$ M or less, and wherein said protein is an IgG antibody. In some embodiments, the anti-TM4SF1 binding protein comprises the IgG antibody, wherein the antibody is humanized. In some embodiments, the protein binds to human TM4SF1 and cross reacts with cynomolgus TM4SF1. In some embodiments, the binding of the protein to human TM4SF1 is not dependent on glycosylation of the ECL2 loop of human TM4SF1. In some embodiments, the protein binds to cynomolgus TM4SF1 with a $K_D$ about $1 \times 10^{-8}$ M or less in a standard flow cytometry assay using HEK293 overexpressing cells. In some embodiments, the protein binds to human TM4SF1 with a $K_D$ of about $1 \times 10^{-9}$ M or less in a standard flow cytometry assay using HUVEC cells. In some embodiments, the protein binds to human TM4SF1 with a $K_D$ of about $5 \times 10^{-8}$ M to about $5 \times 10^{-11}$ M in a standard flow cytometry assay using HUVEC cells. In some embodiments, the protein binds to human TM4SF1 with a $K_D$ of about $5 \times 10^{-10}$ M or less in a standard flow cytometry assay using HUVEC cells. In some embodiments, the binding protein is an anti-TM4SF1 antibody or an antigen binding fragment thereof comprising a human IgG1, IgG2, or IgG4 isotype. In some embodiments, the anti-TM4SF1 binding protein comprises an Fc region comprising at least one mutation that reduces or ablates ADCC or CDC effector function of the binding protein. In some embodiments, the anti-TM4SF1 binding protein comprises an Fc region comprising at least one mutation that reduces or ablates ADCC and CDC effector function of the anti-TM4SF1 antibody, or antigen-binding fragment thereof. In some embodiments, the anti-TM4SF1 binding protein is an IgG1 isotype and comprises an Fc region comprising one or more mutations selected from the group consisting of: E233P, L234V, L234A, L235A, G236Delta (deletion), G237A, V263L, N297A, N297D, N297G, N297Q, K322A, A327G, P329A, A330S, P331A and P331S. In some embodiments, the binding protein is an IgG2 isotype and comprises an Fc region comprising one or more mutations selected from the group consisting of: V234A, G237A, P238S, H268A or H268Q, V309L, A330S and P331S. In some embodiments, the binding protein is an IgG4 isotype and comprises an Fc region comprising a one or more mutations selected from the group consisting of: S228P, E233P, F234A, F234V, L235E, L235A, G236Delta (deletion), N297A, N297D, N297G and N297Q. In some embodiments, the anti-TM4SF1 binding protein comprises an antigen-binding fragment of an anti-TM4SF1 antibody, wherein the antigen-binding fragment comprises a Fab, a Fab', a F(ab')₂, an Fv, or an scFv.

One embodiment provides an anti-TM4SF1 antibody, or an antigen-binding fragment thereof, comprising
a heavy chain variable domain comprising a CDR3 domain comprising an amino acid sequence that has at least 75% identity to SEQ ID NO: 8, a CDR2 domain comprising an amino acid sequence that has at least 75% identity to SEQ ID NO: 7, and a CDR1 domain comprising an amino acid sequence that has at least 75% identity to SEQ ID NO: 6; and a light chain variable domain comprising a CDR3 domain comprising an amino acid sequence that has at least 75% identity to SEQ ID NO: 14, a CDR2 domain comprising an amino acid that has at least 75% identity to SEQ ID NO: 13, and a CDR1 domain comprising an amino acid sequence that has at least 75% identity to SEQ ID NO: 12. In some embodiments, the anti-TM4SF1 antibody, or an antigen-binding fragment thereof comprises:

a heavy chain variable domain comprising a CDR3 domain comprising an amino acid sequence as set forth in SEQ ID NO: 8, a CDR2 domain comprising an amino acid sequence as set forth in SEQ ID NO: 7, and a CDR1 domain comprising an amino acid sequence as set forth in SEQ ID NO: 6; and a light chain variable domain comprising a CDR3 domain comprising an amino acid sequence as set forth in SEQ ID NO: 14, a CDR2 domain comprising an amino acid sequence as set forth in SEQ ID NO: 13, and a CDR1 domain comprising an amino acid sequence as set forth in SEQ ID NO: 12. In some embodiments, the heavy chain variable domain comprises an amino acid sequence as set forth in SEQ ID NO: 3, and the light chain variable domain comprises an amino acid sequence as set forth in SEQ ID NO: 9.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 20, a CDR2 domain comprising an amino acid sequence that has at least 75% identity to SEQ ID NO: 19, and a CDR1 domain comprising an amino acid sequence that has at least 75% identity to SEQ ID NO: 18; and a light chain variable domain comprising a CDR3 domain comprising an amino acid sequence that has at least 75% identity to SEQ ID NO: 26, a CDR2 domain comprising an amino acid sequence that has at least 75% identity to SEQ ID NO: 25, and a CDR1 domain comprising an amino acid sequence that has at least 75% identity to SEQ ID NO: 24. In some embodiments, the anti-TM4SF1 antibody, or an antigen-binding fragment thereof of claim comprises:

a heavy chain variable domain comprising a CDR3 domain comprising an amino acid sequence as set forth in SEQ ID NO: 20, a CDR2 domain comprising an amino acid sequence as set forth in SEQ ID NO: 19, and a CDR1 domain comprising an amino acid sequence as set forth in SEQ ID NO: 18; and a light chain variable domain comprising a CDR3 domain comprising an amino acid sequence as set forth in SEQ ID NO: 26, a CDR2 domain comprising an amino acid sequence as set forth in SEQ ID NO: 25, and a CDR1 domain comprising an amino acid sequence as set forth in SEQ ID NO: 24. In some embodiments, the heavy chain variable domain comprises an amino acid sequence as set forth in SEQ ID NO: 15, and the light chain variable domain comprises an amino acid sequence as set forth in SEQ ID NO: 21.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 32, a CDR2 domain comprising an amino acid sequence an amino acid sequence that has at least 75% identity to SEQ ID NO: 31, and a CDR1 domain comprising an amino acid sequence an amino acid sequence that has at least 75% identity to SEQ ID NO: 30; and a lightchain variable domain comprising a CDR3 domain comprising an amino acid sequence that has at least 75% identity to SEQ ID NO: 38, a CDR2 domain comprising an amino acid sequence that has at least 75% identity to SEQ ID NO: 37, and a CDR1 domain comprising an amino acid sequence that has at least 75% identity to SEQ ID NO: 36. In some embodiments, the anti-TM4SF1 antibody, or an antigen-binding fragment thereof comprises:

a heavy chain variable domain comprising a CDR3 domain comprising an amino acid sequence as set forth in SEQ ID NO: 32, a CDR2 domain comprising an amino acid sequence as set forth in SEQ ID NO: 31, and a CDR1 domain comprising an amino acid sequence as set forth in SEQ ID NO: 30; and a light chain variable domain comprising a CDR3 domain comprising an amino acid sequence as set forth in SEQ ID NO: 38, a CDR2 domain comprising an amino acid sequence as set forth in SEQ ID NO: 37, and a CDR1 domain comprising an amino acid sequence as set forth in SEQ ID NO: 36. In some embodiments, the heavy chain variable domain comprises an amino acid sequence as set forth in SEQ ID NO: 27, and the light chain comprises an amino acid sequence as set forth in SEQ ID NO: 33.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 44, a CDR2 domain comprising an amino acid sequence that has at least 75% identity to SEQ ID NO: 43, and a CDR1 domain comprising an amino acid sequence that has at least 75% identity to SEQ ID NO: 42; and a light chain variable domain comprising a CDR3 domain comprising an amino acid sequence that has at least 75% identity to SEQ ID NO: 50, a CDR2 domain comprising an amino acid sequence that has at least 75% identity to SEQ ID NO: 49, and a CDR1 domain comprising an amino acid sequence that has at least 75% identity to SEQ ID NO: 48. In some embodiments, the anti-TM4SF 1 antibody, or an antigen-binding fragment thereof comprises:

a heavy chain variable domain comprising a CDR3 domain comprising an amino acid sequence as set forth in SEQ ID NO: 44, a CDR2 domain comprising an amino acid sequence as set forth in SEQ ID NO: 43, and a CDR1 domain comprising an amino acid sequence as set forth in SEQ ID NO: 42; and a light chain variable domain comprising a CDR3 domain comprising an amino acid sequence as set forth in SEQ ID NO: 50, a CDR2 domain comprising an amino acid sequence as set forth in SEQ ID NO: 49, and a CDR1 domain comprising an amino acid sequence as set forth in SEQ ID NO: 48. In some embodiments, the heavy chain variable domain comprises an amino acid sequence as set forth in SEQ ID NO: 39, and the light chain variable domain comprises an amino acid sequence as set forth in SEQ ID NO: 45.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 56, a CDR2 domain comprising an amino acid sequence that has at least 75% identity to SEQ ID NO: 55, and a CDR1 domain comprising an amino acid sequence that has at least 75% identity to SEQ ID NO: 54; and a light chain variable domain comprising a CDR3 domain comprising an amino acid sequence that has at least 75% identity to SEQ ID NO: 62, a CDR2 domain comprising an amino acid sequence that has at least 75% identity to SEQ ID NO: 61, and a CDR1 domain comprising an amino acid sequence that has at least 75% identity to SEQ ID NO: 60. In some embodiments, the anti-TM4SF1 antibody, or an antigen-binding fragment thereof comprises:

a heavy chain variable domain comprising a CDR3 domain comprising an amino acid sequence as set forth in SEQ ID NO: 56, a CDR2 domain comprising an amino acid sequence as set forth in SEQ ID NO: 55, and a CDR1 domain comprising an amino acid sequence as set forth in SEQ ID NO: 54; and a light chain variable domain comprising a CDR3 domain comprising an amino acid sequence as set forth in SEQ ID NO: 62, a CDR2 domain comprising an amino acid sequence as set forth in SEQ ID NO: 61, and a CDR1 domain comprising an amino acid sequence as set forth in SEQ ID NO: 60. In some embodiments, the heavy chain variable domain comprises an amino acid sequence as set forth in SEQ ID NO: 51, and the light chain variable domain comprises an amino acid sequence as set forth in SEQ ID NO: 57.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 68, a CDR2 domain comprising an amino acid sequence that has at least 75% identity to SEQ ID NO: 67, and a CDR1 domain comprising an amino acid sequence that has at least 75% identity to SEQ ID NO: 66; and a light chain variable domain comprising a CDR3 domain comprising an amino acid sequence that has at least 75% identity to SEQ ID NO: 74, a CDR2 domain comprising an amino acid sequence that has at least 75% identity to SEQ ID NO: 73, and a CDR1 domain comprising an amino acid sequence that has at least 75% identity to SEQ ID NO: 72. In some embodiments, the anti-TM4SF1 antibody, or an antigen-binding fragment thereof comprises:

a heavy chain variable domain comprising a CDR3 domain comprising an amino acid sequence as set forth in SEQ ID NO: 68, a CDR2 domain comprising an amino acid sequence as set forth in SEQ ID NO: 67, and a CDR1 domain comprising an amino acid sequence as set forth in SEQ ID NO: 66; and a light chain variable domain comprising a CDR3 domain comprising an amino acid sequence as set forth in SEQ ID NO: 74, a CDR2 domain comprising an amino acid sequence as set forth in SEQ ID NO: 73, and a CDR1 domain comprising an amino acid sequence as set forth in SEQ ID NO: 72. In some embodiments, the heavy chain variable domain comprises an amino acid sequence as set forth in SEQ ID NO: 63, and the light chain variable domain comprises an amino acid sequence as set forth in SEQ ID NO: 69.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 80, a CDR2 domain comprising an amino acid sequence that has at least 75% identity to SEQ ID NO: 79, and a CDR1 domain comprising an amino acid sequence that has at least 75% identity to SEQ ID NO: 78; and a light chain variable domain comprising a CDR3 domain comprising an amino acid sequence that has at least 75% identity to SEQ ID NO: 86, a CDR2 domain comprising an amino acid sequence that has at least 75% identity to SEQ ID NO: 85, and a CDR1 domain comprising an amino acid sequence that has at least 75% identity to SEQ ID NO: 84. In some embodiments, the anti-TM4SF1 antibody, or an antigen-binding fragment thereof comprises:

a heavy chain variable domain comprising a CDR3 domain comprising an amino acid sequence as set forth in SEQ ID NO: 80, a CDR2 domain comprising an amino acid sequence as set forth in SEQ ID NO: 79, and a CDR1 domain comprising an amino acid sequence as set forth in SEQ ID NO: 78; and a light chain variable domain comprising a CDR3 domain comprising an amino acid sequence as set forth in SEQ ID NO: 86, a CDR2 domain comprising an amino acid sequence as set forth in SEQ ID NO: 85, and a CDR1 domain comprising an amino acid sequence as set forth in SEQ ID NO: 84. In some embodiments, the heavy chain variable domain comprises an amino acid sequence as set forth in SEQ ID NO: 75, and the light chain variable domain comprises an amino acid sequence as set forth in SEQ ID NO: 81. In some embodiments, the light chain variable region comprises a human IgG framework region and the heavy chain variable region comprises a human IgG framework region. In some embodiments, the antibody or antigen-binding fragment thereof, further comprises an IgG backbone comprising an amino acid sequence set forth in SEQ ID NO: 87 or 88. In some embodiments, the antibody or antigen-binding fragment thereof, further comprises an IgG backbone comprising an amino acid sequence set forth in SEQ ID NO: 89.

One embodiment provides an anti-TM4SF1 antibody, or an antigen-binding fragment thereof, comprising a heavy chain variable domain comprising a CDR3 domain comprising an amino acid sequence that has at least 75% identity to SEQ ID NO: 96, a CDR2 domain comprising an amino acid sequence that has at least 75% identity to SEQ ID NO: 95, and a CDR1 domain comprising an amino acid sequence that has at least 75% identity to SEQ ID NO: 94; and a light chain variable domain comprising a CDR3 domain comprising an amino acid sequence that has at least 75% identity to SEQ ID NO: 110, a CDR2 domain comprising an amino acid sequence that has at least 75% identity to SEQ ID NO: 109, and a CDR1 domain comprising an amino acid sequence that has at least 75% identity to SEQ ID NO: 107. In some embodiments, the anti-TM4SF1 antibody, or an antigen-binding fragment thereof comprises:

a heavy chain variable domain comprising a CDR3 domain comprising an amino acid sequence as set forth in SEQ ID NO: 96, a CDR2 domain comprising an amino acid sequence as set forth in SEQ ID NO: 95, and a CDR1 domain comprising an amino acid sequence as set forth in SEQ ID NO: 94; and a light chain variable domain comprising a CDR3 domain comprising an amino acid sequence as set forth in SEQ ID NO: 110, a CDR2 domain comprising an amino acid sequence as set forth in SEQ ID NO: 109, and a CDR1 domain comprising an amino acid sequence as set forth in SEQ ID NO: 107. In some embodiments, the heavy chain variable domain comprises an amino acid sequence as set forth in SEQ ID NO: 90, and the light chain variable domain comprises an amino acid sequence as set forth in SEQ ID NO: 97.

One embodiment provides an anti-TM4SF1 antibody, or an antigen-binding fragment thereof, comprising
- a heavy chain variable domain comprising a CDR3 domain comprising an amino acid sequence that has at least 75% identity to SEQ ID NO: 96, a CDR2 domain comprising an amino acid sequence that has at least 75% identity to SEQ ID NO: 95, and a CDR1 domain comprising an amino acid sequence that has at least 75% identity to SEQ ID NO: 94; and
- a light chain variable domain comprising a CDR3 domain comprising an amino acid sequence that has at least 75% identity to SEQ ID NO: 110, a CDR2 domain comprising an amino acid sequence that has at least 75% identity to SEQ ID NO: 109, and a CDR1 domain comprising an amino acid sequence that has at least 75% identity to SEQ ID NO: 108. In some embodiments, the anti-TM4SF1 antibody, or an antigen-binding fragment thereof comprises:
- a heavy chain variable domain comprising a CDR3 domain comprising an amino acid sequence as set forth in SEQ ID NO: 96, a CDR2 domain comprising an amino acid sequence as set forth in SEQ ID NO: 95, and a CDR1 domain comprising an amino acid sequence as set forth in SEQ ID NO: 94; and
- a light chain variable domain comprising a CDR3 domain comprising an amino acid sequence as set forth in SEQ ID NO: 110, a CDR2 domain comprising an amino acid sequence as set forth in SEQ ID NO: 109, and a CDR1 domain comprising an amino acid sequence as set forth in SEQ ID NO: 108. In some embodiments, the heavy chain variable domain comprises an amino acid sequence as set forth in SEQ ID NO: 90 or 92, and the light chain variable domain comprises an amino acid sequence as set forth in SEQ ID NO: 101.

One embodiment provides an anti-TM4SF1 antibody, or an antigen-binding fragment thereof, comprising
- a heavy chain variable domain comprising a CDR3 domain comprising an amino acid sequence that has at least 75% identity to SEQ ID NO: 96, a CDR2 domain comprising an amino acid sequence that has at least 75% identity to SEQ ID NO: 95, and a CDR1 domain comprising an amino acid sequence that has at least 75% identity to SEQ ID NO: 94; and
- a light chain variable domain comprising a CDR3 domain comprising an amino acid sequence that has at least 75% identity to SEQ ID NO: 110, a CDR2 domain comprising an amino acid sequence that has at least 75% identity to SEQ ID NO: 109, and a CDR1 domain comprising an amino acid sequence that has at least 75% identity to SEQ ID NO: 107. In some embodiments, the anti-TM4SF1 antibody, or an antigen-binding fragment thereof comprises:
- a heavy chain variable domain comprising a CDR3 domain comprising an amino acid sequence as set forth in SEQ ID NO: 96, a CDR2 domain comprising an amino acid sequence as set forth in SEQ ID NO: 95, and a CDR1 domain comprising an amino acid sequence as set forth in SEQ ID NO: 94; and
- a light chain variable domain comprising a CDR3 domain comprising an amino acid sequence as set forth in SEQ ID NO: 110, a CDR2 domain comprising an amino acid sequence as set forth in SEQ ID NO: 109, and a CDR1 domain comprising an amino acid sequence as set forth in SEQ ID NO: 107. In some embodiments, the heavy chain variable domain comprises an amino acid sequence as set forth in SEQ ID NO: 90 or 92, and the light chain variable domain comprises an amino acid sequence as set forth in SEQ ID NO: 99.

One embodiment provides an anti-TM4SF1 antibody, or an antigen-binding fragment thereof, comprising
- a heavy chain variable domain comprising a CDR3 domain comprising an amino acid sequence that has at least 75% identity to SEQ ID NO: 118, a CDR2 domain comprising an amino acid sequence that has at least 75% identity to SEQ ID NO: 116, and a CDR1 domain comprising an amino acid sequence that has at least 75% identity to SEQ ID NO: 115; and
- a light chain variable domain comprising a CDR3 domain comprising an amino acid sequence that has at least 75% identity to SEQ ID NO: 129, a CDR2 domain comprising an amino acid sequence that has at least 75% identity to SEQ ID NO: 128, and a CDR1 domain comprising an amino acid sequence that has at least 75% identity to SEQ ID NO: 124. In some embodiments, the anti-TM4SF1 antibody, or an antigen-binding fragment thereof comprises:
- a heavy chain variable domain comprising a CDR3 domain comprising an amino acid sequence as set forth in SEQ ID NO: 118, a CDR2 domain comprising an amino acid sequence as set forth in SEQ ID NO: 116, and a CDR1 domain comprising an amino acid sequence as set forth in SEQ ID NO: 115; and
- a light chain variable domain comprising a CDR3 domain comprising an amino acid sequence as set forth in SEQ ID NO: 129, a CDR2 domain comprising an amino acid sequence as set forth in SEQ ID NO: 128, and a CDR1 domain comprising an amino acid sequence as set forth in SEQ ID NO: 124. In some embodiments, the heavy chain variable domain comprises an amino acid sequence as set forth in SEQ ID NO: 112, and the light chain variable domain comprises an amino acid sequence as set forth in SEQ ID NO: 122.

One embodiment provides an anti-TM4SF1 antibody, or an antigen-binding fragment thereof, comprising
- a heavy chain variable domain comprising a CDR3 domain comprising an amino acid sequence that has at least 75% identity to SEQ ID NO: 118, SEQ ID NO: 119, SEQ ID NO: 120 or SEQ ID NO: 121, a CDR2 domain comprising an amino acid sequence that has at least 75% identity to SEQ ID NO: 116 or SEQ ID NO: 117, and a CDR1 domain comprising an amino acid sequence that has at least 75% identity to SEQ ID NO: 115; and
- a light chain variable domain comprising a CDR3 domain comprising an amino acid sequence that has at least 75% identity to SEQ ID NO: 129, a CDR2 domain comprising an amino acid sequence that has at least 75% identity to SEQ ID NO: 128, and a CDR1 domain comprising an amino acid sequence that has at least 75% identity to SEQ ID NO: 124, SEQ ID NO: 125, SEQ ID NO: 126, or SEQ ID NO: 127. In some embodiments, the anti-TM4SF1 antibody, or an antigen-binding fragment thereof of claim 57, comprising
- a heavy chain variable domain comprising a CDR3 domain comprising an amino acid sequence as set forth in SEQ ID NO: 118, SEQ ID NO: 119, SEQ ID NO: 120 or SEQ ID NO: 121, a CDR2 domain comprising an amino acid sequence as set forth in SEQ ID NO: 116 or SEQ ID NO: 117, and a CDR1 domain comprising an amino acid sequence as set forth in SEQ ID NO: 115; and a light chain variable domain comprising a CDR3 domain comprising an amino acid sequence as set forth in SEQ ID NO: 129, a CDR2 domain comprising an amino acid sequence as set forth in SEQ ID NO: 128, and a CDR1 domain comprising an amino acid sequence as set forth in SEQ ID NO: 124, SEQ ID NO: 125, SEQ ID NO: 126, or SEQ ID NO: 127. In some embodiments, the heavy chain variable domain comprises an amino acid sequence as set forth in SEQ ID NO: 112 or 114, and the light chain variable domain comprises an amino acid sequence as set forth in SEQ ID NO: 122.

One embodiment provides an anti-TM4SF1 antibody, or antigen-binding fragment thereof, that binds to an epitope on the ECL2 loop of human TM4SF1 with a $K_D$ of about $5 \times 10^{-8}$ M or less, wherein the anti-TM4SF1 antibody, or antigen-binding fragment thereof, comprises a light chain variable region comprising a human IgG framework region and comprises a heavy chain variable region comprising a human IgG framework region. One embodiment provides an anti-TM4SF1 antibody, or antigen-binding fragment thereof, that binds to an epitope on the ECL2 loop of human TM4SF1 with a $K_D$ about $5 \times 10^{-8}$ M or less, wherein the anti-TM4SF1 antibody, or antigen-binding fragment thereof, is an IgG antibody. In some embodiments, the anti-TM4SF1 antibody or antigen-binding fragment thereof is humanized. In some embodiments, the anti-TM4SF 1 antibody, or antigen-binding fragment thereof, cross reacts with cynomolgus TM4SF1. In some embodiments, the binding of the anti-TM4SF1 antibody to human TM4SF1 is not dependent on glycosylation of the ECL2 loop of human TM4SF1. In some embodiments, the anti-TM4SF1 antibody, or antigen-binding fragment thereof, binds to cynomolgus TM4SF1 with a $K_D$ about $1 \times 10^{-8}$ M or less in a standard flow cytometry assay using HEK293 overexpressing cells. In some embodiments, the anti-TM4SF1 antibody, or antigen-binding fragment thereof, binds to human TM4SF1 with a $K_D$ of about $1 \times 10^{-9}$ M or less in a standard flow cytometry assay using HUVEC cells. In some embodiments, the anti-TM4SF1 antibody, or antigen-binding fragment thereof, binds to human TM4SF1 with a $K_D$ of about $5 \times 10^{-8}$ M to about $5 \times 10^{-11}$ M in a standard flow cytometry assay using HUVEC cells. In some embodiments, the anti-TM4SF1 antibody, or antigen-binding fragment thereof, binds to human TM4SF1 with a $K_D$ of about $5 \times 10^{-10}$ M or less in a standard flow cytometry assay using HUVEC cells. In some embodiments, the anti-TM4SF 1 antibody, or antigen-binding fragment thereof comprises a human IgG1, IgG2, or IgG4 isotype. In some embodiments, the antibody, or antigen binding fragment thereof, comprises an Fc region comprising at least one mutation that reduces or ablates ADCC or CDC effector function of the antibody, or antigen-binding fragment thereof. In some embodiments, the antibody, or antigen binding fragment thereof, is an IgG1 isotype and comprises an Fc region comprising one or more mutations selected from the group consisting of: E233P, L234V, L234A, L235A, G236Delta (deletion), G237A, V263L, N297A, N297D, N297G, N297Q, K322A, A327G, P329A, A330S, P331A and P331S. In some embodiments, the antibody, or antigen binding fragment thereof, is an IgG2 isotype and comprises an Fc region comprising a one or more mutations selected from the group consisting of: V234A, G237A, P238S, H268A or H268Q, V309L, A330S and P331S. In some embodiments, the antibody, or antigen binding fragment thereof, is an IgG4 isotype and comprises an Fc region comprising a one or more mutations selected from the group consisting of: S228P, E233P, F234A, F234V, L235E, L235A, G236Delta (deletion), N297A, N297D, N297G and N297Q. In some embodiments, the anti-TM4SF1 antibody, or antigen-binding fragment thereof, comprises the antigen-binding fragment thereof, wherein the antigen-binding fragment thereof comprises a Fab, a Fab', a F(ab')$_2$, an Fv, or an scFv.

One embodiment provides a method of treating or preventing a disease or disorder in a subject, wherein the disease or disorder is characterized by abnormal endothelial cell (EC)-cell interaction, said method comprising administering the binding protein of any one of claims 1-20, or the antibody, or antigen-binding fragment thereof, of any one of claims 21-74 to the subject. In some embodiments, the EC-cell interaction comprises one or more of EC-mesenchymal stem cell, EC-fibroblast, EC-smooth muscle cell, EC-tumor cell, EC-leukocyte, EC-adipose cell, and EC-neuronal cell interactions. In some embodiments, the disease or disorder comprises an inflammatory disease or a cancer.

One embodiment provides a method of treating or preventing inflammation in a subject, said method comprising administering a binding protein according to any one of claims 1-20, or an anti-TM4SF1 antibody, or antigen-binding fragment thereof, according to any one of claims 21-74 to the subject. One embodiment provides a method of preventing metastasis in a subject, said method comprising administering a binding protein of this disclosure, or an anti-TM4SF1 antibody, or antigen-binding fragment thereof, according to this disclosure, to the subject, wherein the subject is in partial or complete remission from a cancer. One embodiment provides a method of treating a subject having a cancer which is associated with a high risk of metastasis, said method comprising administering a binding protein according to this disclosure, or an anti-TM4SF1 antibody, or antigen-binding fragment thereof, according to this disclosure, to the subject having the cancer which is associated with the high risk of metastasis. One embodiment provides a method of treating or preventing metastasis in a subject having a cancer, said method comprising administering a binding protein according to this disclosure, or an anti-TM4SF1 antibody, or antigen-binding fragment thereof, according to this disclosure to the subject having the cancer. In some embodiments, the subject is undergoing a treatment which may induce metastasis. In some embodiments, the treatment comprises surgery, radiation treatment and chemotherapy. In some embodiments, the subject is a human. In some embodiments, the cancer is a carcinoma or a sarcoma. In some embodiments, the carcinoma comprises breast cancer, lung cancer, colon cancer, or prostate cancer. In some embodiments, the sarcoma comprises an osteosarcoma or a soft tissue sarcoma. In some embodiments, the cancer is a glioblastoma.

One embodiment provides a method of treating or preventing lymphatic or hematogenous metastasis in a human subject comprising administering to the human subject a binding protein according to this disclosure, or an anti-TM4SF1 antibody, or antigen-binding fragment thereof, according to this disclosure. One embodiment provides a pharmaceutical composition comprising (i) a TM4SF1 binding protein according to this disclosure and (ii) a pharmaceutically acceptable carrier. One embodiment provides a pharmaceutical composition comprising (i) an anti-TM4SF1 antibody according to this disclosure, or an antigen binding fragment thereof and (ii) a pharmaceutically acceptable carrier.

One embodiment provides a process for the production of a TM4SF1 binding protein according to this disclosure, said process comprising culturing a host transformed or transfected with a vector comprising a nucleic acid sequence encoding a TM4SF1 binding protein according to this disclosure under conditions allowing the expression of the TM4SF1 binding protein and recovering and purifying the produced protein from the culture.

One embodiment provides a process for the production of an anti-TM4SF1 antibody according to this disclosure, or an antigen binding fragment thereof, said process comprising culturing a host transformed or transfected with a vector comprising a nucleic acid sequence encoding anti-TM4SF1 antibody according to this disclosure, or an antigen binding fragment thereof under conditions allowing the expression of the anti-TM4SF1 antibody or antigen binding fragments thereof and recovering and purifying the produced antibody or the antigen binding fragment thereof from the culture. One embodiment provides an anti-TM4SF1 binding protein having an improved binding affinity to TM4SF1 as compared to an anti-TM4SF1 antibody produced by a hybridoma mouse cell line 8G4-5-13-13F (PTA-120523), as determined by Scatchard analysis. One embodiment provides an anti-TM4SF1 binding protein having an improved specificity to TM4SF1 as compared to an anti-TM4SF1 antibody produced by a hybridoma mouse cell line 8G4-5-13-13F (PTA-120523), as determined by Scatchard analysis. One embodiment provides an anti-TM4SF1 binding protein having a reduced immunogenicity as compared to an anti-TM4SF1 antibody produced by a hybridoma mouse cell line 8G4-5-13-13F (PTA-120523), as determined by HLA molecule binding. One embodiment provides an anti-TM4SF1 binding protein having improved stability as compared to an anti-TM4SF1 antibody produced by a hybridoma mouse cell line 8G4-5-13-13F (PTA-120523). In some embodiments, the TM4SF1 binding protein has improved chemical stability. In some embodiments, the TM4SF1 binding protein has improved physical stability. One embodiment provides an anti-TM4SF1 binding protein having reduced aggregation as compared to an anti-TM4SF1 antibody produced by a hybridoma mouse cell line 8G4-5-13-13F (PTA-120523). One embodiment provides an anti-TM4SF1 binding protein having improved solubility as compared to an anti-TM4SF1 antibody produced by a hybridoma mouse cell line 8G4-5-13-13F (PTA-120523). In some embodiments, the protein binds to cynomolgus TM4SF1 with a $K_D$ about $1 \times 10^{-8}$ M or less in a standard flow cytometry assay using HEK293 overexpressing cells. In some embodiments, the protein binds to human TM4SF1 with a $K_D$ of about $1 \times 10^{-9}$ M or less in a standard flow cytometry assay using HUVEC cells. In some embodiments, the protein binds to human TM4SF1 with a $K_D$ of about $5 \times 10^{-8}$ M to about $5 \times 10^{-11}$ M in a standard flow cytometry assay using HUVEC cells. In some embodiments, the protein binds to human TM4SF1 with a $K_D$ of about $5 \times 10^{-10}$ M or less in a standard flow cytometry assay using HUVEC cells. In some embodiments, the protein comprises: a heavy chain variable domain comprising a CDR3 domain comprising an amino acid sequence that has at least 75% identity to SEQ ID NO: 8, 20, 32, 44, 56, 68, or 80, 96, 118, 119, 120, or 121; a CDR2 domain comprising an amino acid sequence that has at least 75% identity to SEQ ID NO: 7, 19, 31, 43, 55, 67, 79, 95, 116, or 117; and a CDR1 domain comprising an amino acid sequence that has at least 75% identity to SEQ ID NO: 6, 18, 30, 42, 54, 66, 78, 94, or 115; and a light chain variable domain comprising a CDR3 domain comprising an amino acid sequence that has at least 75% identity to SEQ ID NO: 14, 26, 38, 50, 62, 74, 86, 110, or 129; a CDR2 domain comprising an amino acid sequence that has at least 75% identity to SEQ ID NO: 13, 25, 37, 49, 61, 73, 85, or 109, or 128; and a CDR1 comprising an amino acid sequence that has at least 75% identity to SEQ ID NO: 12, 24, 36, 48, 60, 72, 84, 107, 108, 124, 125, 126, or 127. In some embodiments, the anti-TM4SF1 binding protein comprises: a heavy chain variable domain comprising a CDR3 domain comprising an amino acid sequence as set forth in SEQ ID NO: 8, 20, 32, 44, 56, 68, 80, 96, 118, 119, 120, or 121; a CDR2 domain comprising an amino acid sequence as set forth in SEQ ID NO: 7, 19, 31, 43, 55, 67, 79, 95, 116, or 117; and a CDR1 domain comprising an amino acid sequence as set forth in SEQ ID NO: 6, 18, 30, 42, 54, 66, 78, 94, or 115; and a light chain variable domain comprising a CDR3 domain comprising an amino acid sequence as set forth in SEQ ID NO: 14, 26, 38, 50, 62, 74, 86, 110, or 129; a CDR2 domain comprising an amino acid sequence as set forth in SEQ ID NO: 13, 25, 37, 49, 61, 73, 85, 109, or 128; and a CDR1 domain comprising an amino acid sequence as set forth in SEQ ID NO: 12, 24, 36, 48, 60, 72, or 84, 107, 108, 124, 125, 126, or 127. In some embodiments, the anti-TM4SF1 binding protein comprises a heavy chain variable domain comprising an amino acid sequence that has at least 85% identity to SEQ ID NO: 3, 15, 27, 39, 51, 63, 75, 90, 92, 112, or 114, and a variable light chain comprising an amino acid sequence that has at least 85% identity to SEQ ID NO: 9, 21, 33, 45, 57, 69, 81, 97, 99, 101 or 122. In some embodiments, the anti-TM4SF1 binding protein of comprises a heavy chain variable domain comprising a sequence as set forth in SEQ ID NO: 3, 15, 27, 39, 51, 63, 75, 90, 92, 112, or 114, and a variable light chain comprising a sequence as set forth in SEQ ID NO: 9, 21, 33, 45, 57, 69, 81, 97, 99, 101, or 122. In some embodiments, the anti-TM4SF1 binding protein comprises a heavy chain comprising at least one amino acid substitution in the sequence set forth as SEQ ID NO: 90. In some embodiments, the anti-TM4SF1 binding protein comprises a light chain comprising at least one amino acid substitution in the sequence set forth as SEQ ID NO: 97. In some embodiments, the at least one amino acid substitution in the sequence set forth as SEQ ID NO: 90 is in an amino acid position selected from amino acid positions 1, 44, and 80 of SEQ ID NO: 90. In some embodiments, the at least one amino acid substitution in the sequence set forth as SEQ ID NO: 97 is in an amino acid position selected from amino acid positions 3, 26, and 62 of SEQ ID NO: 97. In some embodiments, position 1 of SEQ ID NO: 90 is substituted from glutamine to glutamic acid. In some embodiments, position 44 of SEQ ID NO: 90 is substituted from aspartic acid to glutamic acid. In some embodiments, position 80 of SEQ ID NO: 90 is substituted from pheylanine to tyrosine. In some embodiments, position 3 of SEQ ID NO: 97 is substituted from isoleucine to valine. In some embodiments, position 26 of SEQ ID NO: 97 is substituted from asparagine to glutamine, or from asparagine to serine. In some embodiments, position 62 of SEQ ID NO: 97 is substituted from glycine to serine. In some embodiments, the anti-TM4SF1 binding protein comprises a heavy chain comprising the sequence set forth as SEQ ID NO: 112. In some embodiments, the anti-TM4SF1 binding protein comprises a light chain comprising the sequence set forth as SEQ ID NO: 99 or SEQ ID NO: 101. In some embodiments, the anti-TM4SF 1 binding protein is humanized.

One embodiment provides a process for the production of a TM4SF1 binding protein according to this disclosure, said process comprising culturing a host transformed or transfected with a vector comprising a nucleic acid sequence encoding a TM4SF1 binding protein according to this disclosure under conditions allowing the expression of the TM4SF1 binding protein and recovering and purifying the produced protein from the culture. One embodiment provides, a humanized anti-TM4SF1 binding protein, wherein the protein binds to cynomolgus TM4SF1 with a $K_D$ about $1\times10^{-8}$ M or less in a standard flow cytometry assay using HEK293 overexpressing cells. One embodiment provides a humanized anti-TM4SF1 binding protein, wherein the protein binds to human TM4SF1 with a $K_D$ of about $1\times10^{-9}$ M or less in a standard flow cytometry assay using HUVEC cells. One embodiment provides a humanized anti-TM4SF1 binding protein, wherein the protein binds to human TM4SF1 with a $K_D$ of about $5\times10^{-8}$ M to about $5\times10^{-11}$ M in a standard flow cytometry assay using HUVEC cells. One embodiment provides a humanized anti-TM4SF1 binding protein, wherein the protein binds to human TM4SF1 with a $K_D$ of about $5\times10^{-10}$ M or less in a standard flow cytometry assay using HUVEC cells.

One embodiment provides an anti-TM4SF1 binding protein comprising at least one improved functional characteristics compared to an anti-TM4SF1 antibody produced by a hybridoma mouse cell line 8G4-5-13-13F (PTA-120523), wherein the improved functional characteristics comprises at least one of improved binding affinity, improved specificity, improved antigenicity, increased similarity to human immunoglobulin framework regions, improved manufacturability, improved developability, improved stability, improved solubility, reduced aggregation propensity, improvement in expression, improved production levels.

This disclosure is based, at least in part, on the identification of novel anti-Transmembrane-4 L six family member-1 (TMFSF1) binding proteins, such as anti-TM4SF1 antibodies, and antigen binding fragments thereof, useful, for example, in the treatment of cancer. The disclosure is further based, at least in part, on compositions and methods for inhibiting tumor metastasis. Thus, some embodiments of the disclosure include methods and compositions for blocking tumor metastasis, e.g., to lung and other organs, by preventing tumor cell attachment to and migration through or between vascular endothelial cells.

In one embodiment, the disclosure features humanized antibodies comprising binding regions, e.g., CDR1, CDR2 and CDR3 domains of the heavy and light chain variable regions of the antibodies disclosed herein.

In one embodiment of any of the above aspects or embodiments, the light chain variable region comprising light chain CDRs disclosed herein and a human IgG framework region, and the heavy chain variable region comprises heavy chain CDRs discloses herein and a human IgG framework region.

In another embodiment, the antibody or antigen-binding fragment thereof, comprises an IgG heavy chain constant region comprising an amino acid sequence set forth in SEQ ID NO: 87 or 88.

In another embodiment, the antibody or antigen-binding fragment thereof, comprises a light chain constant region comprising the amino acid sequence set forth in SEQ ID NO: 89.

Provided in one embodiments is an anti-TM4SF1 binding protein comprising a heavy chain variable domain comprising a CDR3 domain comprising an amino acid sequence that has at least 85% identity to SEQ ID NO: 8, 20, 32, 44, 56, 68, or 80; a CDR2 domain comprising an amino acid sequence that has at least 85% identity to SEQ ID NO: 7, 19, 31, 43, 55, 67, or 79; and a CDR1 domain comprising an amino acid sequence that has at least 85% identity to SEQ ID NO: 6, 18, 30, 42, 54, 66, or 78; and a light chain variable domain comprising a CDR3 domain comprising an amino acid sequence that has at least 85% identity to SEQ ID NO: 14, 26, 38, 50, 62, 74, or 86; a CDR2 domain comprising an amino acid sequence that has at least 85% identity to SEQ ID NO: 13, 25, 37, 49, 61, 73, or 85; and a CDR1 comprising an amino acid sequence that has at least 85% identity to SEQ ID NO: 12, 24, 36, 48, 60, 72, or 84. In some embodiments, the anti-TM4SF 1 binding protein comprises a heavy chain variable domain comprising a CDR3 domain comprising an amino acid sequence as set forth in SEQ ID NO: 8, 20, 32, 44, 56, 68, or 80; a CDR2 domain comprising an amino acid sequence as set forth in SEQ ID NO: 7, 19, 31, 43, 55, 67, or 79; and a CDR1 domain comprising an amino acid sequence as set forth in SEQ ID NO: 6, 18, 30, 42, 54, 66, or 78; and a light chain variable domain comprising a CDR3 domain comprising an amino acid sequence as set forth in SEQ ID NO: 14, 26, 38, 50, 62, 74, or 86; a CDR2 domain comprising an amino acid sequence as set forth in SEQ ID NO: 13, 25, 37, 49, 61, 73, or 85; and a CDR1 domain comprising an amino acid sequence as set forth in SEQ ID NO: 12, 24, 36, 48, 60, 72, or 84. In some embodiments, the anti-TM4SF1 binding protein of comprises a heavy chain variable domain comprising an amino acid sequence that has at least 85% identity to SEQ ID NO: 3, 15, 27, 39, 51, 63, or 75, and a variable light chain comprising an amino acid sequence that has at least 85% identity to SEQ ID NO: 9, 21, 33, 45, 57, 69, or 81. In some embodiments, the anti-TM4SF1 binding protein comprises a heavy chain variable domain comprising a sequence as set forth in SEQ ID NO: 3, 15, 27, 39, 51, 63, or 75, and a variable light chain comprising a sequence as set forth in SEQ ID NO: 9, 21, 33, 45, 57, 69, or 81. In some embodiments, the anti-TM4SF1 binding protein binds to an epitope on the ECL2 loop of human TM4SF1 with a $K_D$ of about $5\times10^{-8}$ M or less. In some embodiments, the anti-TM4SF1 binding protein binds to an epitope on the ECL2 loop of human TM4SF1 with a $K_D$ about $5\times10^{-8}$ M or less, and wherein said protein is an IgG antibody. In some embodiments, the anti-TM4SF1 binding protein comprises the IgG antibody, wherein the antibody is humanized. In some embodiments, the anti-TM4SF1 binding protein binds to human TM4SF1 and cross reacts with cynomolgus TM4SF1. In some embodiments, the binding of the anti-TM4SF1 binding protein to human TM4SF1 is not dependent on glycosylation of the ECL2 loop of human TM4SF1. In some embodiments, the anti-TM4SF1 binding protein binds to cynomolgus TM4SF1 with a $K_D$ about $1\times10^{-8}$ M or less in a standard flow cytometry assay using HEK293 overexpressing cells. In some embodiments, the anti-TM4SF1 binding protein binds to human TM4SF1 with a $K_D$ of about $1\times10^{-9}$ M or less in a standard flow cytometry assay using HUVEC cells. In some embodiments, the anti-TM4SF1 binding protein binds to human TM4SF1 with a $K_D$ of about $5\times10^{-8}$ M to about $5\times10^{-11}$ M in a standard flow cytometry assay using HUVEC cells. In some embodiments, the anti-TM4SF1 binding protein binds to human TM4SF1 with a $K_D$ of about $5\times10^{-10}$ M or less in a standard flow cytometry assay using HUVEC cells. In some embodiments, the anti-TM4SF1 binding protein comprises a human IgG1, IgG2, or IgG4 isotype. In some embodiments, the anti-TM4SF1 binding protein is an anti-TM4SF1 antigen binding protein or an antigen binding fragment thereof comprising an Fc region comprising at least one mutation that reduces or ablates ADCC or CDC effector function of the antibody, or antigen-binding fragment thereof. In some embodiments, the anti-TM4SF1 binding protein comprises an Fc region comprising at least one mutation that reduces or ablates ADCC and CDC effector function of the antibody, or antigen-binding fragment thereof. In some embodiments, the anti-TM4SF1 binding protein is an IgG1 isotype and comprises an Fc region comprising one or more mutations selected from the group consisting of: E233P, L234V, L234A, L235A, G236Delta (deletion), G237A, V263L, N297A, N297D, N297G, N297Q, K322A, A327G, P329A, A330S, P331A and P331S. In some embodiments, the anti-TM4SF1 binding protein is an IgG2 isotype and comprises an Fc region comprising one or more mutations selected from the group consisting of: V234A, G237A, P238S, H268A or H268Q, V309L, A330S and P331S. In some embodiments, the anti-TM4SF1 binding protein is an IgG4 isotype and comprises an Fc region comprising a one or more mutations selected from the group consisting of: S228P, E233P, F234A, F234V, L235E, L235A, G236Delta (deletion), N297A, N297D, N297G and N297Q. In some embodiments, the anti-TM4SF1 binding protein comprises an antigen-binding fragment of an anti-TM4SF1 antibody, wherein the antigen-binding fragment comprises a Fab, a Fab', a F(ab')$_2$, an Fv, or an scFv.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 8, a CDR2 domain comprising an amino acid sequence that has at least 85% identity to SEQ ID NO: 7, and a CDR1 domain comprising an amino acid sequence that has at least 85% identity to SEQ ID NO: 6; and a light chain variable domain comprising a CDR3 domain comprising an amino acid sequence that has at least 85% identity to SEQ ID NO: 14, a CDR2 domain comprising an amino acid that has at least 85% identity to SEQ ID NO: 13, and a CDR1 domain comprising an amino acid sequence that has at least 85% identity to SEQ ID NO: 12. In some embodiments, the anti-TM4SF1 antibody, or an antigen-binding fragment thereof comprises a heavy chain variable domain comprising a CDR3 domain comprising an amino acid sequence as set forth in SEQ ID NO: 8, a CDR2 domain comprising an amino acid sequence as set forth in SEQ ID NO: 7, and a CDR1 domain comprising an amino acid sequence as set forth in SEQ ID NO: 6; and a light chain variable domain comprising a CDR3 domain comprising an amino acid sequence as set forth in SEQ ID NO: 14, a CDR2 domain comprising an amino acid sequence as set forth in SEQ ID NO: 13, and a CDR1 domain comprising an amino acid sequence as set forth in SEQ ID NO: 12. In some embodiments, the anti-TM4SF1 antibody, or antigen-binding fragment thereof comprises the heavy chain variable domain comprising an amino acid sequence as set forth in SEQ ID NO: 3, and the light chain variable domain comprising an amino acid sequence as set forth in SEQ ID NO: 9.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 20, a CDR2 domain comprising an amino acid sequence that has at least 85% identity to SEQ ID NO: 19, and a CDR1 domain comprising an amino acid sequence that has at least 85% identity to SEQ ID NO: 18; and a light chain variable domain comprising a CDR3 domain comprising an amino acid sequence that has at least 85% identity to SEQ ID NO: 26, a CDR2 domain comprising an amino acid sequence that has at least 85% identity to SEQ ID NO: 25, and a CDR1 domain comprising an amino acid sequence that has at least 85% identity to SEQ ID NO: 24. In some embodiments, the anti-TM4SF 1 antibody, or an antigen-binding fragment thereof of claim 24, comprising a heavy chain variable domain comprising a CDR3 domain comprising an amino acid sequence as set forth in SEQ ID NO: 20, a CDR2 domain comprising an amino acid sequence as set forth in SEQ ID NO: 19, and a CDR1 domain comprising an amino acid sequence as set forth in SEQ ID NO: 18; and a light chain variable domain comprising a CDR3 domain comprising an amino acid sequence as set forth in SEQ ID NO: 26, a CDR2 domain comprising an amino acid sequence as set forth in SEQ ID NO: 25, and a CDR1 domain comprising an amino acid sequence as set forth in SEQ ID NO: 24. In some embodiments, the anti-TM4SF1 antibody, or antigen-binding fragment thereof comprises the heavy chain variable domain comprising an amino acid sequence as set forth in SEQ ID NO: 15, and the light chain variable domain comprising an amino acid sequence as set forth in SEQ ID NO: 21.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 32, a CDR2 domain comprising an amino acid sequence an amino acid sequence that has at least 85% identity to SEQ ID NO: 31, and a CDR1 domain comprising an amino acid sequence an amino acid sequence that has at least 85% identity to SEQ ID NO: 30; and a light chain variable domain comprising a CDR3 domain comprising an amino acid sequence that has at least 85% identity to SEQ ID NO: 38, a CDR2 domain comprising an amino acid sequence that has at least 85% identity to SEQ ID NO: 37, and a CDR1 domain comprising an amino acid sequence that has at least 85% identity to SEQ ID NO: 36. In some embodiments, the anti-TM4SF1 antibody, or an antigen-binding fragment thereof comprises a heavy chain variable domain comprising a CDR3 domain comprising an amino acid sequence as set forth in SEQ ID NO: 32, a CDR2 domain comprising an amino acid sequence as set forth in SEQ ID NO: 31, and a CDR1 domain comprising an amino acid sequence as set forth in SEQ ID NO: 30; and a light chain variable domain comprising a CDR3 domain comprising an amino acid sequence as set forth in SEQ ID NO: 38, a CDR2 domain comprising an amino acid sequence as set forth in SEQ ID NO: 37, and a CDR1 domain comprising an amino acid sequence as set forth in SEQ ID NO: 36. In some embodiments, the anti-TM4SF1 antibody, or antigen-binding fragment thereof comprises the heavy chain variable domain comprising an amino acid sequence as set forth in SEQ ID NO: 27, and the light chain comprising an amino acid sequence as set forth in SEQ ID NO: 33.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 44, a CDR2 domain comprising an amino acid sequence that has at least 85% identity to SEQ ID NO: 43, and a CDR1 domain comprising an amino acid sequence that has at least 85% identity to SEQ ID NO: 42; and a light chain variable domain comprising a CDR3 domain comprising an amino acid sequence that has at least 85% identity to SEQ ID NO: 50, a CDR2 domain comprising an amino acid sequence that has at least 85% identity to SEQ ID NO: 49, and a CDR1 domain comprising an amino acid sequence that has at least 85% identity to SEQ ID NO: 48. In some embodiments, the anti-TM4SF 1 antibody, or an antigen-binding fragment thereof comprises a heavy chain variable domain comprising a CDR3 domain comprising an amino acid sequence as set forth in SEQ ID NO: 44, a CDR2 domain comprising an amino acid sequence as set forth in SEQ ID NO: 43, and a CDR1 domain comprising an amino acid sequence as set forth in SEQ ID NO: 42; and a light chain variable domain comprising a CDR3 domain comprising an amino acid sequence as set forth in SEQ ID NO: 50, a CDR2 domain comprising an amino acid sequence as set forth in SEQ ID NO: 49, and a CDR1 domain comprising an amino acid sequence as set forth in SEQ ID NO: 48. In some embodiments, the anti-TM4SF1 antibody, or antigen-binding fragment thereof comprises the heavy chain variable domain comprising an amino acid sequence as set forth in SEQ ID NO: 39, and the light chain variable domain comprising an amino acid sequence as set forth in SEQ ID NO: 45.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 56, a CDR2 domain comprising an amino acid sequence that has at least 85% identity to SEQ ID NO: 55, and a CDR1 domain comprising an amino acid sequence that has at least 85% identity to SEQ ID NO: 54; and a light chain variable domain comprising a CDR3 domain comprising an amino acid sequence that has at least 85% identity to SEQ ID NO: 62, a CDR2 domain comprising an amino acid sequence that has at least 85% identity to SEQ ID NO: 61, and a CDR1 domain comprising an amino acid sequence that has at least 85% identity to SEQ ID NO: 60. In some embodiments, the anti-TM4SF 1 antibody, or an antigen-binding fragment thereof of claim 33, comprising a heavy chain variable domain comprising a CDR3 domain comprising an amino acid sequence as set forth in SEQ ID NO: 56, a CDR2 domain comprising an amino acid sequence as set forth in SEQ ID NO: 55, and a CDR1 domain comprising an amino acid sequence as set forth in SEQ ID NO: 54; and a light chain variable domain comprising a CDR3 domain comprising an amino acid sequence as set forth in SEQ ID NO: 62, a CDR2 domain comprising an amino acid sequence as set forth in SEQ ID NO: 61, and a CDR1 domain comprising an amino acid sequence as set forth in SEQ ID NO: 60. In some embodiments, the anti-TM4SF1 antibody, or antigen-binding fragment thereof comprises the heavy chain variable domain comprising an amino acid sequence as set forth in SEQ ID NO: 51, and the light chain variable domain comprising an amino acid sequence as set forth in SEQ ID NO: 57.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 68, a CDR2 domain comprising an amino acid sequence that has at least 85% identity to SEQ ID NO: 67, and a CDR1 domain comprising an amino acid sequence that has at least 85% identity to SEQ ID NO: 66; and a light chain variable domain comprising a CDR3 domain comprising an amino acid sequence that has at least 85% identity to SEQ ID NO: 74, a CDR2 domain comprising an amino acid sequence that has at least 85% identity to SEQ ID NO: 73, and a CDR1 domain comprising an amino acid sequence that has at least 85% identity to SEQ ID NO: 72. In some embodiments, the anti-TM4SF 1 antibody, or an antigen-binding fragment thereof comprising a heavy chain variable domain comprising a CDR3 domain comprising an amino acid sequence as set forth in SEQ ID NO: 68, a CDR2 domain comprising an amino acid sequence as set forth in SEQ ID NO: 67, and a CDR1 domain comprising an amino acid sequence as set forth in SEQ ID NO: 66; and a light chain variable domain comprising a CDR3 domain comprising an amino acid sequence as set forth in SEQ ID NO: 74, a CDR2 domain comprising an amino acid sequence as set forth in SEQ ID NO: 73, and a CDR1 domain comprising an amino acid sequence as set forth in SEQ ID NO: 72. In some embodiments, the anti-TM4SF1 antibody, or antigen-binding fragment thereof comprises the heavy chain variable domain comprising an amino acid sequence as set forth in SEQ ID NO: 63, and the light chain variable domain comprising an amino acid sequence as set forth in SEQ ID NO: 69.

One embodiment provides an anti-TM4SF1 antibody, or an antigen-binding fragment thereof, comprising a heavy chain variable domain comprising a CDR3 domain comprising an amino acid sequence that has at least 85% identity to SEQ ID NO: 80, a CDR2 domain comprising an amino acid sequence that has at least 85% identity to SEQ ID NO: 79, and a CDR1 domain comprising an amino acid sequence that has at least 85% identity to SEQ ID NO: 78; and a light chain variable domain comprising a CDR3 domain comprising an amino acid sequence that has at least 85% identity to SEQ ID NO: 86, a CDR2 domain comprising an amino acid sequence that has at least 85% identity to SEQ ID NO: 85, and a CDR1 domain comprising an amino acid sequence that has at least 85% identity to SEQ ID NO: 84. In some embodiments, the anti-TM4SF 1 antibody, or an antigen-binding fragment thereof comprises a heavy chain variable domain comprising a CDR3 domain comprising an amino acid sequence as set forth in SEQ ID NO: 80, a CDR2 domain comprising an amino acid sequence as set forth in SEQ ID NO: 79, and a CDR1 domain comprising an amino acid sequence as set forth in SEQ ID NO: 78; and a light chain variable domain comprising a CDR3 domain comprising an amino acid sequence as set forth in SEQ ID NO: 86, a CDR2 domain comprising an amino acid sequence as set forth in SEQ ID NO: 85, and a CDR1 domain comprising an amino acid sequence as set forth in SEQ ID NO: 84. In some embodiments, the anti-TM4SF1 antibody, or antigen-binding fragment thereof comprises the heavy chain variable domain comprising an amino acid sequence as set forth in SEQ ID NO: 75, and the light chain variable domain comprising an amino acid sequence as set forth in SEQ ID NO: 81. In some embodiments, the anti-TM4SF1 antibody, or antigen-binding fragment thereof comprises the light chain variable region comprising a human IgG framework region and the heavy chain variable region comprising a human IgG framework region. In some embodiments, the anti-TM4SF1 antibody, or antigen-binding fragment thereof further comprises an IgG backbone comprising an amino acid sequence set forth in SEQ ID NO: 87 or 88. In some embodiments, the anti-TM4SF1 antibody, or antigen-binding fragment thereof, further comprises an IgG backbone comprising an amino acid sequence set forth in SEQ ID NO: 89.

One embodiment provides an anti-TM4SF1 antibody, or antigen-binding fragment thereof, that binds to an epitope on the ECL2 loop of human TM4SF1 with a $K_D$ of about $5 \times 10^{-8}$ M or less, wherein the anti-TM4SF1 antibody, or antigen-binding fragment thereof, comprises a light chain variable region comprising a human IgG framework region and comprises a heavy chain variable region comprising a human IgG framework region.

One embodiment provides an anti-TM4SF1 antibody, or antigen-binding fragment thereof, that binds to an epitope on the ECL2 loop of human TM4SF1 with a $K_D$ about $5 \times 10^{-8}$ M or less, wherein the anti-TM4SF1 antibody, or antigen-binding fragment thereof, is an IgG antibody.

In some embodiments, the anti-TM4SF1 antibody, or antigen-binding fragment thereof is humanized. In some embodiments, the anti-TM4SF1 antibody, or antigen-binding fragment thereof, cross reacts with cynomolgus TM4SF1. In some embodiments, the binding of the anti-TM4SF1 antibody to human TM4SF1 is not dependent on glycosylation of the ECL2 loop of human TM4SF1. In some embodiments, the anti-TM4SF1 antibody, or antigen-binding fragment thereof binds to cynomolgus TM4SF1 with a $K_D$ about $1 \times 10^{-8}$ M or less in a standard flow cytometry assay using HEK293 overexpressing cells. In some embodiments, the anti-TM4SF1 antibody, or antigen-binding fragment thereof binds to human TM4SF1 with a $K_D$ of about $1 \times 10^{-9}$ M or less in a standard flow cytometry assay using HUVEC cells. In some embodiments, the anti-TM4SF 1 antibody, or antigen-binding fragment thereof binds to human TM4SF1 with a $K_D$ of about $5 \times 10^{-8}$ M to about $5 \times 10^{-11}$ M in a standard flow cytometry assay using HUVEC cells. In some embodiments, the anti-TM4SF1 antibody, or antigen-binding fragment thereof binds to human TM4SF1 with a $K_D$ of about $5 \times 10^{-10}$ M or less in a standard flow cytometry assay using HUVEC cells. In some embodiments, the anti-TM4SF1 antibody, or antigen-binding fragment thereof comprises human IgG1, IgG2, or IgG4 isotype. In some embodiments, the anti-TM4SF1 antibody, or antigen-binding fragment thereof comprises an Fc region comprising at least one mutation that reduces or ablates ADCC or CDC effector function of the antibody, or antigen-binding fragment thereof. In some embodiments, the anti-TM4SF1 antibody, or antigen-binding fragment thereof comprises an Fc region comprising at least one mutation that reduces or ablates ADCC and CDC effector function of the antibody, or antigen-binding fragment thereof. In some embodiments, the anti-TM4SF1 antibody, or antigen-binding fragment thereof is an IgG1 isotype and comprises an Fc region comprising one or more mutations selected from the group consisting of: E233P, L234V, L234A, L235A, G236Delta (deletion), G237A, V263L, N297A, N297D, N297G, N297Q, K322A, A327G, P329A, A330S, P331A and P331S. In some embodiments, the anti-TM4SF1 antibody, or antigen-binding fragment thereof is an IgG2 isotype and comprises an Fc region comprising a one or more mutations selected from the group consisting of: V234A, G237A, P238S, H268A or H268Q, V309L, A330S and P331S. In some embodiments, the anti-TM4SF1 antibody, or antigen-binding fragment thereof is an IgG4 isotype and comprises an Fc region comprising a one or more mutations selected from the group consisting of: S228P, E233P, F234A, F234V, L235E, L235A, G236Delta (deletion), N297A, N297D, N297G and N297Q. In some embodiments, the anti-TM4SF1 antibody, or antigen-binding fragment thereof comprises the antigen-binding fragment thereof, wherein the antigen-binding fragment thereof comprises a Fab, a Fab', a F(ab')$_2$, an Fv, or an scFv.

Provided in one embodiment is a method of treating or preventing a disease or disorder in a subject, wherein the disease or disorder is characterized by abnormal endothelial cell (EC)-cell interaction, said method comprising administering the binding protein or the antibody, or antigen-binding fragment thereof according to the present disclosure. In some embodiments EC-cell interaction comprises one or more of EC-mesenchymal stem cell, EC-fibroblast, EC-smooth muscle cell, EC-tumor cell, EC-leukocyte, EC-adipose cell, and EC-neuronal cell interactions. In some embodiments, the disease or disorder comprises an inflammatory disease or a cancer.

One embodiment provides a method of treating or preventing inflammation in a subject, said method comprising administering a binding protein or an anti-TM4SF1 antibody, or antigen-binding fragment thereof according to the present disclosure.

One embodiment provides a method of preventing metastasis in a subject, said method comprising administering a binding protein or an anti-TM4SF1 antibody, or antigen-binding fragment thereof, according to the present disclosure, wherein the subject is in partial or complete remission from a cancer.

One embodiment provides a method of treating a subject having a cancer which is associated with a high risk of metastasis, said method comprising administering a binding protein or an anti-TM4SF1 antibody, or antigen-binding fragment thereof, according to the present disclosure to the subject having the cancer which is associated with the high risk of metastasis.

One embodiment provides a method of treating or preventing metastasis in a subject having a cancer, said method comprising administering a binding protein, or an anti-TM4SF1 antibody, or antigen-binding fragment thereof, according to the present disclosure, to the subject having the cancer. In some embodiments, the subject is undergoing a treatment which may induce metastasis. In some embodiments, the treatment comprises surgery, radiation treatment and chemotherapy. In some embodiments, the subject is a human. In some embodiments, the cancer is a carcinoma or a sarcoma. In some embodiments, the carcinoma comprises breast cancer, lung cancer, colon cancer, or prostate cancer. In some embodiments, the sarcoma comprises an osteosarcoma or a soft tissue sarcoma. In some embodiments, the cancer is a glioblastoma.

One embodiment provides a method of treating or preventing lymphatic or hematogenous metastasis in a human subject comprising administering to the human subject a binding protein, or an anti-TM4SF1 antibody, or antigen-binding fragment thereof, according to the present disclosure.

One embodiment provides a pharmaceutical composition comprising (i) a TM4SF1 binding protein according to the present disclosure and (ii) a pharmaceutically acceptable carrier.

One embodiment provides a pharmaceutical composition comprising (i) an anti-TM4SF1 antibody according to the present disclosure, or an antigen binding fragment thereof and (ii) a pharmaceutically acceptable carrier.

One embodiment provides a process for the production of a TM4SF1 binding protein according to the present disclosure, said process comprising culturing a host transformed or transfected with a vector comprising a nucleic acid sequence encoding a TM4SF1 binding protein according to the present disclosure under conditions allowing the expression of the TM4SF1 binding protein and recovering and purifying the produced protein from the culture.

One embodiment provides a process for the production of an anti-TM4SF1 antibody according to the present disclosure, or an antigen binding fragment thereof, said process comprising culturing a host transformed or transfected with a vector comprising a nucleic acid sequence encoding anti-TM4SF1 antibody according to the present disclosure, or an antigen binding fragment thereof under conditions allowing the expression of the anti-TM4SF1 antibody or antigen binding fragments thereof and recovering and purifying the produced antibody or the antigen binding fragment thereof from the culture.

In one embodiment, the TM4SF1 binding protein or the anti-TM4SF1 antibody, or antigen-binding fragment thereof, binds human TM4SF1 in a manner that is not dependent on glycosylation of the ECL2 loop of human TM4SF1.

In one embodiment, the TM4SF1 binding protein or the anti-TM4SF1 antibody, or antigen-binding fragment thereof, binds to cynomolgus TM4SF1 with a $K_D$ about $5 \times 10^{-8}$ M or less in a standard flow cytometry assay using HEK293 cells. In one embodiment, the HEK293 cells are transfected to express cynomolgus TM4SF1. In a further embodiment, HEK293 cells express cynomolgus TM4SF1 at about 600 mRNA copies per $10^6$ copies 18S rRNA.

In another embodiment, the TM4SF1 binding protein or the anti-TM4SF1 antibody, or antigen-binding fragment thereof, binds to human TM4SF1 with a $K_D$ of about $1 \times 10^{-8}$ M or less in a standard flow cytometry assay using HUVEC cells.

In another embodiment, the TM4SF1 binding protein or the anti-TM4SF1 antibody, or antigen-binding fragment thereof, binds to human TM4SF1 with a $K_D$ of about $5 \times 10^{-8}$ M to about $5 \times 10^{-11}$ M in a standard flow cytometry assay using HUVEC cells.

In a further embodiment, the TM4SF1 binding protein or the anti-TM4SF1 antibody, or antigen-binding fragment thereof, binds to human TM4SF1 with a $K_D$ of about $5 \times 10^{-10}$ M or less in a standard flow cytometry assay using HUVEC cells.

In certain embodiments, the TM4SF1 binding protein or the anti-TM4SF1 antibody, or antigen-binding fragment thereof, is a human IgG1, IgG2, or IgG4 isotype.

In further embodiments, the TM4SF1 binding protein or the anti-TM4SF1 antibody, or antigen-binding fragment thereof, comprises an Fc region comprising at least one mutation that reduces or ablates ADCC and/or CDC effector function of the antibody, or antigen-binding fragment thereof. In further embodiments, the anti-TM4SF1 antibody, or antigen-binding fragment thereof, comprises an Fc region comprising at least two mutations that reduce or ablate ADCC and/or CDC effector function of the antibody, or antigen-binding fragment thereof. In further embodiments, the anti-TM4SF1 antibody, or antigen-binding fragment thereof, comprises an Fc region comprising at least three, at least four, at least five, at least six, at least seven, at least eight, at least nine, at least ten or more mutations that reduce or ablate ADCC and/or CDC effector function of the antibody, or antigen-binding fragment thereof.

In still other embodiments, the TM4SF1 binding protein or the anti-TM4SF1 antibody, or antigen-binding fragment thereof, is an IgG1 isotype and comprises an Fc region comprising one or more mutations selected from the group consisting of E233P, L234V, L234A, L235A, G236Delta (deletion), G237A, V263L, N297A, N297D, N297G, N297Q, K322A, A327G, P329A, A330S, P331A and P331S.

In other embodiments, the anti-TM4SF1 TM4SF1 binding protein or the antibody, or antigen-binding fragment thereof, is an IgG2 isotype and comprises an Fc region comprising one or more mutations selected from the group consisting of V234A, G237A, P238S, H268A or H268Q, V309L, A330S and P331S.

In other embodiments, the TM4SF1 binding protein or the anti-TM4SF1 antibody, or antigen-binding fragment thereof, is an IgG4 isotype and comprises an Fc region comprising one or more mutations selected from the group consisting of S228P, E233P, F234A, F234V, L235E, L235A, G236Delta (deletion), N297A, N297D, N297G and N297Q.

In one aspect, the TM4SF1 binding protein or the anti-TM4SF1 antigen binding fragment thereof, is a Fab, a Fab', a F(ab')$_2$, an Fv, or an scFv.

In one aspect, the disclosure provides a method of treating or preventing a disease or disorder in a subject, wherein the disease or disorder is characterized by undesirable endothelial cell (EC)-cell interactions, said method comprising administering the antibody, or antigen-binding fragment thereof, described herein to the subject.

In one embodiment, the EC-cell interaction is selected from the group consisting of EC-EC, EC-mesenchymal stem cell, EC-fibroblast, EC-smooth muscle cell, EC-tumor cell, EC-leukocyte, EC-adipose cell and EC-neuronal cell interactions.

In another embodiment, the disease or disorder is selected from an inflammatory disease or a cancer.

In another aspect, the disclosure features a method of treating or preventing inflammation in a subject, said method comprising administering the antibody, or antigen-binding fragment thereof, described herein to the subject.

In one aspect, the disclosure provides a method of preventing metastasis in a subject, said method comprising administering an anti-TM4SF1 antibody, or antigen-binding fragment thereof, to the subject, wherein the subject is in partial or complete remission from cancer.

In another aspect, the disclosure provides a method of treating a subject having cancer which is associated with a high risk of metastasis comprising administering an antibody, or antigen-binding fragment thereof, described herein to the subject having cancer which is associated with a high risk of metastasis.

In another aspect, the disclosure provides a method of treating or preventing metastasis in a subject having cancer, said method comprising administering an antibody, or antigen-binding fragment thereof, described herein.

In a further aspect, the disclosure includes a method of treating or preventing hematogenous metastasis in a subject comprising administering to the subject a TM4SF1 binding protein, such as an anti-TM4SF1 antibody, or antigen-binding fragment thereof, described herein.

In a further aspect, the disclosure includes a method of treating or preventing lymphatic metastasis in a subject comprising administering to the subject a TM4SF1 binding protein, such as an anti-TM4SF1 antibody, or antigen-binding fragment thereof, described herein.

In one embodiment, the subject is undergoing treatment which may induce metastasis. In further embodiments, the treatment is selected from the group consisting of surgery, radiation treatment and chemotherapy.

In one embodiment, the subject is human.

The disclosure further provides, in another aspect, a method of treating or preventing metastasis in a human subject comprising administering to the subject an effective amount of an TM4SF1 binding protein, such as an anti-TM4SF1 antibody, or an antigen binding fragment thereof, described herein, wherein the effective amount of the antibody, or antigen binding fragment thereof, comprises 1 to 80 mg/kg of the amount of the antibody, or antigen binding fragment thereof.

In yet another aspect, the disclosure provides a method of treating a subject having cancer which is associated with a high risk of metastasis, said method comprising administering to the subject an effective amount of an TM4SF1 antibody, such as an anti-TM4SF1 antibody, or an antigen binding fragment thereof, described herein, wherein the effective amount of the antibody, or antigen binding fragment thereof, comprises 1 to 80 mg/kg of the amount of the antibody, or antigen binding fragment thereof.

In one embodiment, the TM4SF1 binding protein, such as the anti-TM4SF1 antibody, or antigen binding fragment thereof, is administered in a frequency such that a serum concentration of about 1 μg/ml or more is maintained in the subject throughout the period until the next dose is administered.

In certain embodiments, the effective amount of the TM4SF1 binding protein, such as the anti-TM4SF1 antibody, or an antigen binding fragment thereof, that is administered is an amount sufficient to, at one week, achieve circulating antibody concentrations >1 μg/ml.

In other embodiments, the effective amount of the TM4SF1 binding protein, such as the anti-TM4SF1 antibody, or an antigen binding fragment thereof, that is administered is an amount sufficient to maintain serum concentrations of the antibody at or above 1 μg/ml continuously for about 1 month.

The disclosure also provides, in a further aspect, a method of treating or preventing metastasis in a human subject comprising administering to the subject 1 mg/kg to 80 mg/kg of an TM4SF1 binding protein, such as an anti-TM4SF1 antibody, or an antigen binding fragment thereof, once a week. TM4SF1 binding proteins or anti-TM4SF1 antibodies or fragments thereof described herein are, in some embodiments, used in the method of treating or preventing metastasis according to a maintenance dosing schedule.

In one embodiment, the cancer is a carcinoma (e.g., breast cancer, lung cancer, colon cancer, and prostate cancer) or a sarcoma (e.g., osteosarcoma or a soft tissue sarcoma).

In one embodiment, the cancer is glioblastoma.

In one embodiment, the human subject has a cancer which is associated with a high risk of metastasis.

In another embodiment, the subject is undergoing treatment which may induce metastasis. In further embodiments, the treatment is selected from the group consisting of: surgery, radiation treatment and chemotherapy.

In another embodiment, the human subject was treated for cancer and has a risk of developing metastasis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

As shown in FIG. 3A, TM4SF1 expression levels decrease with confluency. As shown in FIG. 3B, high TM4SF1-expressing B16F10 cells generate more lung metastases than lower TM4SF1 expressors. Exemplary metastases are indicated with an arrow.

FIG. 5 shows the variable heavy chain (VH) sequence (SEQ ID NO: 3), variable light chain (VL) sequence (SEQ ID NO: 9) of antibody AGX-A03. In FIG. 5, the heavy chain CDR1 (SEQ ID NO: 6), CDR2 (SEQ ID NO: 7) and CDR3 (SEQ ID NO: 8) sequences are underlined and the light chain CDR1 (SEQ ID NO: 12), CDR2 (SEQ ID NO: 13) and CDR3 (SEQ ID NO: 14) sequences are underlined.

FIG. 6 shows the variable heavy chain (VH) sequence (SEQ ID NO: 15), variable light chain (VL) sequence (SEQ ID NO: 21) of antibody AGX-A04. In FIG. 6, the heavy chain CDR1 (SEQ ID NO: 18), CDR2 (SEQ ID NO: 19) and CDR3 (SEQ ID NO: 20) sequences are underlined and the light chain CDR1 (SEQ ID NO: 24), CDR2 (SEQ ID NO: 25) and CDR3 (SEQ ID NO: 26) sequences are underlined.

FIG. 7 shows the variable heavy chain (VH) sequence (SEQ ID NO: 27), variable light chain (VL) sequence (SEQ ID NO: 33) of antibody AGX-A05. In FIG. 7, the heavy chain CDR1 (SEQ ID NO: 30), CDR2 (SEQ ID NO: 31) and CDR3 (SEQ ID NO: 32) sequences are underlined and the light chain CDR1 (SEQ ID NO: 36), CDR2 (SEQ ID NO: 37) and CDR3 (SEQ ID NO: 38) sequences are underlined.

FIG. 8 shows the variable heavy chain (VH) sequence (SEQ ID NO: 39), variable light chain (VL) sequence (SEQ ID NO: 45) of antibody AGX-A07. In FIG. 8, the heavy chain CDR1 (SEQ ID NO: 42), CDR2 (SEQ ID NO: 43) and CDR3 (SEQ ID NO: 44) sequences are underlined and the light chain CDR1 (SEQ ID NO: 48), CDR2 (SEQ ID NO: 49) and CDR3 (SEQ ID NO: 50) sequences are underlined.

FIG. 9 shows the variable heavy chain (VH) sequence (SEQ ID NO: 51), variable light chain (VL) sequence (SEQ ID NO: 57) of antibody AGX-A08. In FIG. 9, the heavy chain CDR1 (SEQ ID NO: 54), CDR2 (SEQ ID NO: 55) and CDR3 (SEQ ID NO: 56) sequences are underlined and the light chain CDR1 (SEQ ID NO: 60), CDR2 (SEQ ID NO: 61) and CDR3 (SEQ ID NO: 62) sequences are underlined.

FIG. 10 shows the variable heavy chain (VH) sequence (SEQ ID NO: 63), variable light chain (VL) sequence (SEQ ID NO: 69) of antibody AGX-A09. In FIG. 10, the heavy chain CDR1 (SEQ ID NO: 66), CDR2 (SEQ ID NO: 67) and CDR3 (SEQ ID NO: 68) sequences are underlined and the light chain CDR1 (SEQ ID NO: 72), CDR2 (SEQ ID NO: 73) and CDR3 (SEQ ID NO: 74) sequences are underlined.

FIG. 11 shows the variable heavy chain (VH) sequence (SEQ ID NO: 75), variable light chain (VL) sequence (SEQ ID NO: 81) of antibody AGX-A11. In FIG. 11, the heavy chain CDR1 (SEQ ID NO: 78), CDR2 (SEQ ID NO: 79) and CDR3 (SEQ ID NO: 80) sequences are underlined and the light chain CDR1 (SEQ ID NO: 84), CDR2 (SEQ ID NO: 85) and CDR3 (SEQ ID NO: 86) sequences are underlined.

FIG. 13(A) shows HUVEC pre-labeled with AGX-A01 (at a concentration of 1 µg/ml) at 4° C. FIG. 13(B) shows uptake of AGX-A01 by HUVEC pre-labeled with AGX-A01 (at a concentration of 1 µg/ml) at 4° C. and returned to culture at 37° C. FIG. 13(C) shows uptake of AGX-A01 by HUVEC pre-labeled with AGX-A01 (at a concentration of 1 µg/ml) at 4° C. and returned to culture at 37° C. in the presence of a clathrin inhibitor, 20 NM pitstop-2. FIG. 13(D) shows uptake of AGX-A01 by HUVEC pre-labeled with AGX-A01 (at a concentration of 1 µg/ml) at 4° C. and returned to culture at 37° C. in the presence of a clathrin and caveolin mediated endocytosis inhibitor, 10 NM chloropromazine. FIG. 13(E) shows uptake of AGX-A01 by HUVEC pre-labeled with AGX-A01 (at a concentration of 1 µg/ml) at 4° C. and returned to culture at 37° C. in the presence of an autophagy inhibitor, 0.4 µM bifilomycin A. FIG. 13(F) shows uptake of AGX-A01 by HUVEC pre-labeled with AGX-A01 (at a concentration of 1 µg/ml) at 4° C. and returned to culture at 37° C. in the presence of a dynamin inhibitor, 20 µM dynasore.

DETAILED DESCRIPTION OF THE INVENTION

Figure 1:
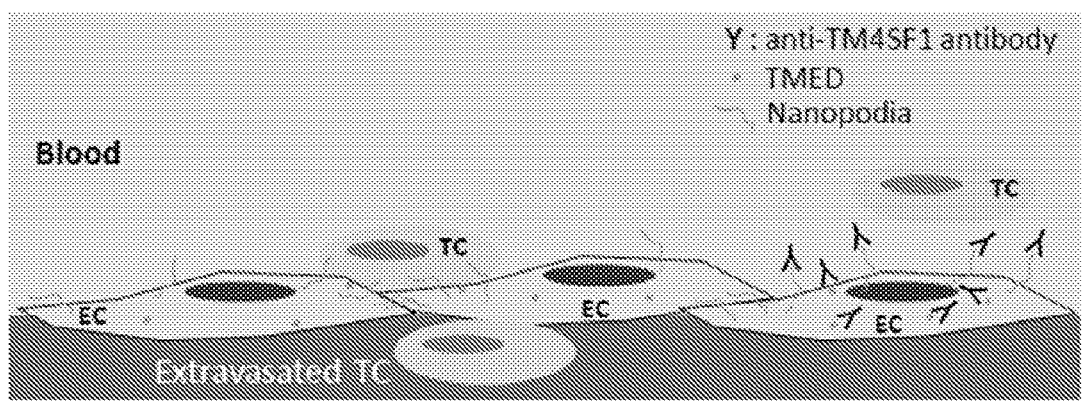
FIG. 1 is a schematic that shows the role of TM4SF1 in tumor cell (TC) and endothelial cell (EC) interactions for extravasation.

Transmembrane-4 L six family member-1 (TM4SF1) is a small membrane glycoprotein with tetraspanin topology that is highly expressed on many human epithelial tumor cells.

In one embodiment, the disclosure provides novel TM4SF1 binding proteins, such as anti-TM4SF1 antibodies, and antigen-binding fragments thereof. The disclosure includes, in some examples, methods of using TM4SF1 binding proteins, such as anti-TM4SF1 antibodies or antigen binding fragments thereof, for treating or preventing cancer. The disclosure includes, but is not limited to, compositions and methods for inhibiting blood-borne tumor metastasis. Accordingly, the disclosure provides, at least in part, antibodies against human TM4SF1 that block tumor metastasis to lung and other organs by preventing tumor cell (TC) attachment to and migration across vascular endothelial cells (ECs).

I. Definitions

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the present disclosure may be more readily understood, select terms are defined below. The terms "transmembrane-4 L six family member-1" or "TM4SF1", as used herein refer to a polypeptide of the transmembrane 4 superfamily/tetraspanin family, which is highly expressed on tumor vasculature endothelial cells (ECs), tumor cells (TCs), ECs of developing retinal vasculature, and angiogenic blood vessels. TM4SF1 has two extracellular loops (ECL1 and ECL2) that are separated by four transmembrane domains (M1, M2, M3, and M4), the N- and C-termini, and the intracellular loop (ICL). ECL2 contains two N-glycosylation sites. The amino acid sequence of human TM4SF1 (hTM4SF1) is described in SEQ ID NO: 90 (see also NCBI Ref Seq No. NP_055035.1).

The term "antibody", as used herein, means any antigen-binding molecule comprising at least one complementarity determining region (CDR) that specifically binds to or interacts with a particular antigen (e.g., TM4SF1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-TMS4F1 antibody (or antigen-binding portion thereof) may be identical to the human germline sequences, or may be naturally or artificially modified. An amino acid consensus sequence may be defined based on a side-by-side analysis of two or more CDRs.

The term "intact antibody" refers to an antibody comprising four polypeptide chains, two heavy (H) chains and two light (L) chains inter-connected by disulfide bonds. In one embodiment, the anti-TM4SF1 antibody is an intact antibody. In one embodiment, the intact antibody is an intact human IgG1, IgG2 or IgG4 isotype. In certain embodiments, the anti-TM4SF1 antibody, or antigen-binding fragment thereof, is a human IgG1, IgG2, or IgG4 isotype.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from intact antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide.

The term "variable region" or "variable domain" of an antibody, or fragment thereof, as used herein refers to the portions of the light and heavy chains of antibody molecules that include amino acid sequences of complementarity determining regions (CDRs; i.e., CDR-1, CDR-2, and CDR-3), and framework regions (FRs). VH refers to the variable domain of the heavy chain. VL refers to the variable domain of the light chain. According to the methods used in this disclosure, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

The term "complementarity determining regions" or "CDRs" as used herein refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

The term "framework regions" (hereinafter FR) as used herein refers to those variable domain residues other than the CDR residues. Each variable domain typically has four FRs identified as FR1, FR2, FR3 and FR4. Common structural features among the variable regions of antibodies, or functional fragments thereof, are well known in the art. The DNA sequence encoding a particular antibody can generally be found following well known methods such as those described in Kabat, et al. 1987 Sequence of Proteins of Immunological Interest, U.S. Department of Health and Human Services, Bethesda Md., which is incorporated herein as a reference. In addition, a general method for cloning functional variable regions from antibodies can be found in Chaudhary, V. K., et al., 1990 Proc. Natl. Acad. Sci. USA 87:1066, which is incorporated herein as a reference.

The term "Fc region" herein is used to define a C-terminal region of an antibody heavy chain, including, for example, native sequence Fc regions, recombinant Fc regions, and variant Fc regions. Although the boundaries of the Fc region of an antibody heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

The term "humanized antibody" as used herein refers to an antibody or a variant, derivative, analog or fragment thereof, which immunospecifically binds to an antigen of interest (e.g., human TM4SF1), and which comprises a framework (FR) region having substantially the amino acid sequence of a human antibody and a complementary determining region (CDR) having substantially the amino acid sequence of a non-human antibody. Humanized forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and U.S. Pat. No. 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The term "monoclonal antibody" as used herein refers to an antibody obtained from a population of substantially homogeneous antibodies, i.e., the individual antibodies comprising the population are identical except for possible mutations, e.g., naturally occurring mutations that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal-antibody preparation is directed against a single epitope on an antigen.

The term "chimeric antibody" as used herein refers to antibodies (immunoglobulins) that have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "epitope" as used herein refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

"Binding affinity" generally refers to the strength of the sum total of noncovalent interactions between a single binding site of a molecule (e.g., a binding protein such as an antibody) and its binding partner (e.g., an antigen). The affinity of a binding molecule X (e.g., anti-TM4SF1 antibody) for its binding partner Y (e.g., human TM4SF1) can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ may also be measured by using FACS or surface plasmon resonance assays by BIACORE, using, for example, a BIACORE 2000 or a BIACORE 3000, or by biolayer interferometry using, for example, the OCTET QK384 system. In certain embodiments, the $K_D$ of an anti-TM4SF1 antibody is determined using a standard flow cytometry assay with HUVEC cells. An "on-rate" or "rate of association" or "association rate" or "$k_{on}$" and an "off-rate" or "rate of dissociation" or "dissociation rate" or "$k_{off}$" may also be determined with the same surface plasmon resonance or biolayer interferometry techniques described above using, for example, a BIACORE 2000 or a BIACORE 3000, or the OCTET QK384 system.

The term "$k_{on}$", as used herein, is intended to refer to the on rate constant for association of an antibody to the antigen to form the antibody/antigen complex, as is known in the art.

The term "$k_{off}$", as used herein, is intended to refer to the off rate constant for dissociation of an antibody from the antibody/antigen complex, as is known in the art.

The term "inhibition" or "inhibit," when used herein, refers to partial (such as, 1%, 2%, 5%, 10%, 20%, 25%, 50%, 75%, 90%, 95%, 99%) or complete (i.e., 100%) inhibition.

The term "cancer" as used herein, refers to or describes the physiological condition in mammals that is typically characterized by unregulated cell growth.

The term "cancer which is associated with a high risk of metastasis", as used herein, refers to a cancer that is associated with at least one factor known to increase the risk that a subject having the cancer will develop metastatic cancer. Examples of factors associated with increased risk for metastasis include, but are not limited to, the number of cancerous lymph nodes a subject has at the initial diagnosis of cancer, the size of the tumor, histological grading, and the stage of the cancer at initial diagnosis.

The term "hematogenous metastasis" as used herein refers to the ability of cancer cells to penetrate the walls of blood vessels, after which they are able to circulate through the bloodstream (circulating tumor cells) to other sites and tissues in the body.

The term "lymphatic metastasis" as used herein refers to the ability of cancer cells to penetrate lymph vessels and drain into blood vessels.

In the context of the disclosure, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth and/or proliferation of cancer cells. In one embodiment, the compositions and methods described herein are used to treat metastasis in a subject having metastatic cancer.

The term "preventing cancer" or "prevention of cancer" refers to delaying, inhibiting, or preventing the onset of a cancer in a mammal in which the onset of oncogenesis or tumorigenesis is not evidenced but a predisposition for cancer is identified whether determined by genetic screening, for example, or otherwise. The term also encompasses treating a mammal having premalignant conditions to stop the progression of, or cause regression of, the premalignant conditions towards malignancy. Examples of premalignant conditions include hyperplasia, dysplasia, and metaplasia. In some embodiments, preventing cancer is used in reference to a subject who is in remission from cancer.

A variety of cancers, including malignant or benign and/or primary or secondary, may be treated or prevented with a method according to the disclosure. Examples of such cancers are known to those skilled in the art and listed in standard textbooks such as the Merck Manual of Diagnosis and Therapy (published by Merck).

The term "subject" as used herein, refers to a mammal (e.g., a human).

The term "administering" as used herein refers to a method of giving a dosage of an antibody or fragment thereof, or a composition (e.g., a pharmaceutical composition) to a subject. The method of administration can vary depending on various factors (e.g., the binding protein or the pharmaceutical composition being administered and the severity of the condition, disease, or disorder being treated).

The term "effective amount" as used herein refers to the amount of an antibody or pharmaceutical composition provided herein which is sufficient to result in the desired outcome.

The terms "about" and "approximately" mean within 20%, within 15%, within 10%, within 9%, within 8%, within 7%, within 6%, within 5%, within 4%, within 3%, within 2%, within 1%, or less of a given value or range.

The term "identity," or "homology" as used interchangeable herein, may be to calculations of "identity," "homology," or "percent homology" between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions ×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In some embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search may determine homology between two sequences.

The two sequences can be genes, nucleotides sequences, protein sequences, peptide sequences, amino acid sequences, or fragments thereof. The actual comparison of the two sequences can be accomplished by well-known methods, for example, using a mathematical algorithm. A non-limiting example of such a mathematical algorithm may be described in Karlin, S. and Altschul, S., Proc. Natl. Acad. Sci. USA, 90-5873-5877 (1993). Such an algorithm may be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another embodiment, the percent identity between two amino acid sequences can be accomplished using, for example, the GAP program in the GCG software package (Accelrys, Cambridge, UK).

The term "manufacturability," as used herein, refers to the stability of a particular protein during recombinant expression and purification of that protein. Manufacturability is believed to be due to the intrinsic properties of the molecule under conditions of expression and purification. Examples of improved manufacturability characteristics include uniform glycosylation of a protein, increased cell titer, growth and protein expression during recombinant production of the protein, improved purification properties, less propensity of aggregation or non-aggregation, and improved stability, including, but not limited to, thermal stability and stability at low pH. In some embodiments are provided TM4SF1 binding proteins that demonstrate the manufacturability, along with retention of in vitro and in vivo activity, compared with other TM4SF1 antibodies. In some embodiments, humanization of a parent TM4SF1 binding protein, by making amino acid substitutions in the CDR or framework regions, can confer additional manufacturability benefits.

In some embodiments are provided TM4SF1 binding proteins that demonstrate improved developability characteristics, including, but not limited to improved purification yield, for example, after protein A purification or size exclusion chromatography, improved homogeneity after purification, improved thermal stability. In some cases, the improvement is with respect to an anti-TM4SF1 antibody produced by a hybridoma mouse cell line 8G4-5-13-13F (PTA-120523), as determined by HLA molecule binding.

In some examples, binding affinity is determined by Scatchard analysis, which comprises generating a Scatchard plot, which is a plot of the ratio of concentrations of bound ligand to unbound ligand versus the bound ligand concentration.

II. TM4SF1 Binding Proteins

One embodiment of the disclosure provides TM4SF1 binding proteins. In some embodiments, the TM4SF1 binding proteins are antibodies and antigen binding fragments thereof, that can be used, e.g., to treat or prevent cancer. In certain embodiments, the anti-TM4SF1 antibodies and antigen binding fragments of the disclosure can be used to prevent tumor cells from metastasizing. The anti-TM4SF1 antibodies and antigen binding fragments thereof, of this disclosure, in some examples, prevent tumor cell metastasis by interfering with the interaction between tumor cells and blood vessel endothelial cells.

TM4SF1 is a small plasma membrane glycoprotein (NCBI Ref Seq No. N P_055035.1) with tetraspanin topology but not homology (Wright et al. Protein Sci. 9: 1594-1600, 2000). It forms TM4SF1-enriched domains (TMED) on plasma membranes, where, like genuine tetraspanins, it serves as a molecular facilitator that recruits functionally related membrane and cytosolic molecules (Shih et al. Cancer Res. 69: 3272-3277, 2009; Zukauskas et al., Angiogenesis. 14: 345-354, 2011), and plays important roles in cancer cell growth (Hellstrom et al. Cancer Res. 46: 391 7-3923, 1986), motility (Chang et al. Int J Cancer. 1 16: 243-252, 2005), and metastasis (Richman et al. Cancer Res. 5916s-5920s, 1995). The amino acid sequence of human TM4SF1 protein (NCBI RefSeq No. NP_055035.1) is shown below as SEQ ID NO: 134.

MCYGKCARCI GHSLVGLALL CIAANILLYF PNGETKYASE

NHLSRFVWFF SGIVGGGLLM LLPAFVFIGL EQDDCCGCCG

HENCGKRCAM LSSVLAALIG IAGSGYCVIV

AALGLAEGPLCLDSLGQWNYTFASTEGQYLLDTSTWSECTEPKHIVEWNVS

LFSILLALGGIEFILCLIQVINGVLGGIC GFCCSHQQQY DC

The anti-TM4SF1 antibodies and antigen binding fragments thereof, of the disclosure are specific to the ECL2 domain of TM4SF1. The amino acid sequence of human TM4SF1 ECL2 domain is EGPLCLDSLGQWNYTFASTEGQYLLDTSTWSECTEPKHIVEWNVSLFS (SEQ ID NO: 135).

As described in Table 2 below, included in the disclosure are novel antibodies that are specific to TM4SF1. The antibodies described in Table 2 are monoclonal murine antibodies AGX-A03, AGX-A04, AGX-A05, AGX-A07, AGX-A08, AGX-A09, and AGX-A11, each of which were identified in the screen described in the Examples and bind the ECL2 region of TM4SF1. Further provided in Table 2 below are humanized antibodies h AGX-A07 and h AGX-A01.

In some embodiments, the antibodies or antigen-binding fragments thereof, comprise an IgG heavy chain constant region comprising an amino acid sequence set forth in SEQ ID NO: 87 or 88, or a sequence that is at least about 60%, at least about 65%, at least about 70%, at least about 75%, at least about, at least about 80%, at least about 85%, at least about 90%, at least about 95%, at least about 96%, at least about 97%, at least about 98%, at least about 99%, or 100% identical to SEQ ID NO: 73 or 74.

In another embodiment, the antibody or antigen-binding fragment thereof, comprises a light chain constant region comprising the amino acid sequence set forth in SEQ ID NO: 89, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 89.

In another embodiment, the antibody or antigen-binding fragment thereof, comprises a heavy chain variable domain comprising the amino acid sequence set forth in SEQ ID NO: 3, 15, 27, 39, 51, 63, or 75, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 3, 15, 27, 39, 51, 63, or 75.

In another embodiment, the antibody or antigen-binding fragment thereof is humanized and, comprises a heavy chain variable domain comprising the amino acid sequence set forth in SEQ ID NO: 90 or 92 or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 90 or 92.

In another embodiment, the antibody or antigen-binding fragment thereof is humanized and, comprises a heavy chain variable domain comprising the amino acid sequence set forth in SEQ ID NO: 112 or 114, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 112 or 114.

In another embodiment, the antibody or antigen-binding fragment thereof, comprises a light chain variable domain comprising the amino acid sequence set forth in SEQ ID NO: 9, 21, 33, 45, 57, 69, or 81, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 9, 21, 33, 45, 57, 69, or 81.

In another embodiment, the antibody or antigen-binding fragment thereof is humanized and, comprises a light chain variable domain comprising the amino acid sequence set forth in SEQ ID NO: 97, 99, 101, 103, or 105 or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 97, 99, 101, 103 or 105. In another embodiment, the antibody or antigen-binding fragment thereof is humanized and, comprises a light chain variable domain comprising the amino acid sequence set forth in SEQ ID NO: 97, 99, or 101 or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 97, 99, or 101.

In another embodiment, the antibody or antigen-binding fragment thereof is humanized and, comprises a light chain variable domain comprising the amino acid sequence set forth in SEQ ID NO: 122, or a sequence that is at least about 60%, at least about 65%, at least about 70%, at least about 75%, at least about 80%, at least about 85%, at least about 90%, at least about 95%, at least about 96%, at least about 97%, at least about 98%, at least about 99% identical, or 100% identical to SEQ ID NO: 122.

In some embodiments, the anti-TM4SF1 antibody or antigen binding fragment thereof comprises a heavy chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 6, 18, 30, 42, 54, 66, or 78. In some embodiments, the anti-TM4SF1 antibody or antigen binding fragment thereof comprises a heavy chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 7, 19, 31, 43, 55, 67, or 79. In some embodiments, the anti-TM4SF1 antibody or antigen binding fragment thereof comprises a heavy chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 8, 20, 32, 44, 56, 68, or 80.

In some embodiments, the anti-TM4SF1 antibody or antigen binding fragment thereof comprises a light chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 12, 24, 36, 48, 60, 72, or 84. In some embodiments, the anti-TM4SF1 antibody or antigen binding fragment thereof comprises a light chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 13, 25, 37, 49, 61, 73, or 85. In some embodiments, the anti-TM4SF1 antibody or antigen binding fragment thereof comprises a light chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 14, 26, 38, 50, 62, 74, or 86.

In some embodiments, the anti-TM4SF1 antibody or antigen binding fragment thereof is humanized and comprises a heavy chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 94 or SEQ ID NO: 115. In some embodiments, the anti-TM4SF1 antibody or antigen binding fragment thereof is humanized and comprises a heavy chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 95, SEQ ID NO: 116, or SEQ ID NO: 117. In some embodiments, the anti-TM4SF1 antibody or antigen binding fragment thereof is humanized and comprises a heavy chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 96, SEQ ID NO: 118, SEQ ID NO: 119, SEQ ID NO: 120, or SEQ ID NO: 121.

In some embodiments, the anti-TM4SF1 antibody or antigen binding fragment thereof is humanized and comprises a light chain CDR1 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 107, SEQ ID NO: 108, SEQ ID NO: 124, SEQ ID NO: 125, SEQ ID NO: 126, or SEQ ID NO: 127. In some embodiments, the anti-TM4SF1 antibody or antigen binding fragment thereof is humanized comprises a light chain CDR2 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 109 or SEQ ID NO: 128. In some embodiments, the anti-TM4SF1 antibody or antigen binding fragment thereof is humanized and comprises a light chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 110, SEQ ID NO: 111, or SEQ ID NO: 129. In some embodiments, the anti-TM4SF1 antibody or antigen binding fragment thereof is humanized and comprises a light chain CDR3 comprising an amino acid sequence that is from at least about 80% to at least about 85%, from at least about 85% to at least about 90%, from at least about 90% to at least about 91%, from at least about 91% to at least about 92%, from at least about 92% to at least about 93%, from at least about 93% to at least about 94%, from at least about 94% to at least about 95%, from at least about 95% to at least about 96%, from at least about 96% to at least about 97%, from at least about 97% to at least about 98%, from at least about 98% to at least about 99%, or from at least about 99% to 100% identical to SEQ ID NO: 110, or SEQ ID NO: 129.

The amino acid sequences of murine monoclonal antibody AGX-A03 are described in Table 2. Specifically, the heavy chain CDR sequences are set forth in SEQ ID Nos: 6, 7, and 8 (CDR1, CDR2, and CDR3), and the light chain CDR amino acid sequences are set forth in SEQ ID Nos: 12, 13, and 14 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 6, 7, and 8 and/or a light chain variable region comprising CDRs as set forth in the amino acid sequences of SEQ ID Nos: 12, 13, and 14. Included in the disclosure are humanized antibodies or antigen binding fragments comprising the CDRs of AGX-A03. Further, the heavy chain variable amino acid sequences and the light chain variable amino acid sequences of AGX-A03 are described in SEQ ID NOS: 3 and 9, respectively.

The amino acid sequences of murine monoclonal antibody AGX-A04 are described in Table 2. Specifically, the heavy chain CDR sequences are set forth in SEQ ID Nos: 18, 19, and 20 (CDR1, CDR2, and CDR3), and the light chain CDR amino acid sequences are set forth in SEQ ID Nos: 24, 25, and 26 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 18, 19, and 20 and/or a light chain variable region comprising CDRs as set forth in the amino acid sequences of SEQ ID Nos: 24, 25, and 26. Included in the disclosure are humanized antibodies or antigen binding fragments comprising the CDRs of AGX-A04. Further, the heavy chain variable amino acid sequences and the light chain variable amino acid sequences of AGX-A04 are described in SEQ ID NOS: 15 and 21, respectively.

The amino acid sequences of murine monoclonal antibody AGX-A05 are described in Table 2. Specifically, the heavy chain CDR sequences are set forth in SEQ ID Nos: 30, 31, and 32 (CDR1, CDR2, and CDR3), and the light chain CDR amino acid sequences are set forth in SEQ ID Nos: 36, 37, and 38 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 30, 31, and 32 and/or a light chain variable region comprising CDRs as set forth in the amino acid sequences of SEQ ID Nos: 36, 37, and 38. Included in the disclosure are humanized antibodies or antigen binding fragments comprising the CDRs of AGX-A05. Further, the heavy chain variable amino acid sequences and the light chain variable amino acid sequences of AGX-A05 are described in SEQ ID NOS: 27 and 33, respectively.

The amino acid sequences of murine monoclonal antibody AGX-A07 are described in Table 2. Specifically, the heavy chain CDR sequences are set forth in SEQ ID Nos: 42, 43, and 44 (CDR1, CDR2, and CDR3), and the light chain CDR amino acid sequences are set forth in SEQ ID Nos: 48, 49, and 50 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 42, 43, and 44 and/or a light chain variable region comprising CDRs as set forth in the amino acid sequences of SEQ ID Nos: 48, 49, and 50. Included in the disclosure are humanized antibodies or antigen binding fragments comprising the CDRs of AGX-A07. Further, the heavy chain variable amino acid sequences and the light chain variable amino acid sequences of AGX-A07 are described in SEQ ID NOs: 39 and 45, respectively.

In one embodiment, a humanized AGX-A07 (h AGX-A07) antibody or antigen binding fragments thereof is provided, comprising a heavy chain sequence as forth in the amino acid sequence of SEQ ID NO: 90. In some embodiments, the humanized AGX-A07 antibody or antigen binding fragments thereof is a humanized mutated AGX-A07 (hm AGX-A07) antibody or antigen binding fragments thereof, comprising a heavy chain sequence comprising one or more substitutions in the sequence as set forth in the amino acid sequence of SEQ ID NO: 90. As shown in Table 2, the heavy chain sequence set forth in SEQ ID NO: 90 is also referred to herein as AGX-A07 H2. In some embodiments, the humanized AGX-A07 antibody or antigen binding fragments thereof is a humanized mutated AGX-A07 antibody or antigen binding fragments thereof, comprising a heavy chain sequence comprising one or more substitutions in the sequence as set forth in the amino acid sequence of SEQ ID NO: 90, wherein the one or more substitutions are in amino acid positions 1, 44, and 80 of SEQ ID NO: 90. In some cases, the humanized mutated AGX-A07 antibody or antigen binding fragments thereof comprises an E1Q (glutamic acid to glutamine substitution at position 1 of the heavy chain, SEQ ID NO: 90). In some cases, the humanized mutated AGX-A07 antibody or antigen binding fragments thereof comprises a D44G (aspartate to glycine substitution at position 44 of the heavy chain, SEQ ID NO: 90). In some cases, the humanized mutated AGX-A07 antibody or antigen binding fragments thereof comprises a F80Y (phenylalanine to tyrosine substitution at position 80 of the heavy chain, SEQ ID NO: 90). In some embodiments, a humanized mutated AGX-A07 antibody or antigen binding fragments is provided, comprising a heavy chain sequence as forth in the amino acid sequence of SEQ ID NO: 92. As shown in Table 2, the heavy chain sequence set forth in SEQ ID NO: 92 is also referred to herein as AGX-A07 H2v1. In some embodiments, humanized AGX-A07 antibodies or antigen binding fragments are provided, comprising a light chain sequence as forth in the amino acid sequence of SEQ ID NO: 97. As shown in Table 2, the light chain sequence set forth in SEQ ID NO: 97 is also referred to herein as AGX-A07 L5. In some embodiments, the humanized AGX-A07 antibody or antigen binding fragments thereof is a humanized mutated AGX-A07 antibody or antigen binding fragments thereof, comprising a light chain sequence comprising one or more substitutions in the sequence as set forth in the amino acid sequence of SEQ ID NO: 97. In some embodiments, the humanized AGX-A07 antibodies or antigen binding fragments thereof is a humanized mutated AGX-A07 antibody or antigen binding fragments thereof, comprising a light chain sequence comprising one or more substitutions in the sequence as set forth in the amino acid sequence of SEQ ID NO: 97, wherein the one or more substitutions are in amino acid positions 3, 26, 62, and 90 of SEQ ID NO: 97. In some cases, the humanized mutated AGX-A07 antibody or antigen binding fragments thereof comprises an I3V (isoluecine to valine substitution at position 3 of the light chain, SEQ ID NO: 97). In some cases, the humanized mutated AGX-A07 antibody or antigen binding fragments thereof comprises a N26Q (asparagine to glutamine substitution at position 26 of the light chain, SEQ ID NO: 97). In some cases, the humanized mutated AGX-A07 antibody or antigen binding fragments thereof comprises a N26S (asparagine to serine substitution at position 26 of the light chain, SEQ ID NO: 97). In some cases, the humanized mutated AGX-A07 antibody or antigen binding fragments thereof comprises a G62S (glycine to serine substitution at position 62 of the light chain, SEQ ID NO: 97). In some cases, the humanized mutated AGX-A07 antibody or antigen binding fragments thereof comprises a W90Y (tryptophan to tyrosine substitution at position 90 of the light chain, SEQ ID NO: 97). In some embodiments, humanized mutated AGX-A07 antibodies or antigen binding fragments are provided, comprising a light chain sequence as forth in an amino acid sequence selected from the group consisting of SEQ ID NO: 99, SEQ ID NO: 101, SEQ ID NO: 103, and SEQ ID NO: 105. As shown in Table 2, the light chain sequence set forth in SEQ ID NO: 99 is also referred to herein as AGX-A07 L5v1, the light chain sequence set forth in SEQ ID NO: 101 is also referred to herein as AGX-A07 L5v2, the light chain sequence set forth in SEQ ID NO: 103 is also referred to herein as AGX-A07 L5v3, and the light chain sequence set forth in SEQ ID NO: 105 is also referred to herein as AGX-A07 L5v4. Exemplary coding sequence for the heavy chain of a humanized AGX-A07 antibody or antigen binding fragment thereof is provided in SEQ ID NO: 91. Exemplary coding sequence for the heavy chain of a humanized mutated AGX-A07 antibody or antigen binding fragment thereof is provided in SEQ ID NO: 93. Exemplary coding sequence for the light chain of a humanized AGX-A07 antibody or antigen binding fragment thereof is provided in SEQ ID NO: 98 (AGX-A07 L5). Exemplary coding sequences for the light chain of a humanized mutated AGX-A07 antibody or antigen binding fragment thereof are provided in SEQ ID NO: 100 (AGX-A07 L5v1), SEQ ID NO: 102 (AGX-A07 L5v2), SEQ ID NO: 104 (AGX-A07 L5v3), and SEQ ID NO: 106 (AGX-A07 L5v4).

In some cases, the humanized AGX-A07 antibodies or antigen binding fragments thereof comprise heavy chain CDR sequences as set forth in SEQ ID Nos: 94, 95, and 96 (CDR1, CDR2, and CDR3), or CDR sequences comprising one or more substitutions in the sequences as set forth in SEQ ID Nos: 94, 95, and 96 (CDR1, CDR2, and CDR3). In some cases, the humanized mutated AGX-A07 antibodies or antigen binding fragments thereof comprises heavy chain CDR sequences as set forth in SEQ ID Nos: 94, 95, and 96 (CDR1, CDR2, and CDR3), or CDR sequences comprising one or more substitutions in the sequences as set forth in SEQ ID Nos: 94, 95, and 96 (CDR1, CDR2, and CDR3).

In some cases, the humanized mutated AGX-A07 antibodies or antigen binding fragments thereof comprise heavy chain CDR1 sequence as set forth in SEQ ID NO: 94, or a heavy chain CDR1 sequence comprising one or more substitutions in the sequences as set forth in SEQ ID NO: 94. In some cases, the humanized mutated AGX-A07 antibodies or antigen binding fragments thereof comprise a heavy chain CDR2 sequence as set forth in SEQ ID NO: 95, or a heavy chain CDR2 sequence comprising one or more substitutions in the sequences as set forth in SEQ ID NO: 95. In some cases, the humanized mutated AGX-A07 antibodies or antigen binding fragments thereof comprise a heavy chain CDR3 sequence as set forth in SEQ ID NO: 96, or a heavy chain CDR3 sequence comprising one or more substitutions in the sequences as set forth in SEQ ID NO: 96.

In some cases, the humanized AGX-A07 antibodies or antigen binding fragments thereof comprise light chain CDR sequences as set forth in SEQ ID Nos: 107, 109, and 110 (CDR1, CDR2, and CDR3), or CDR sequences comprising one or more substitutions in the sequences as set forth in SEQ ID Nos: 107, 109, and 110 (CDR1, CDR2, and CDR3). In some cases, the humanized AGX-A07 antibodies or antigen binding fragments thereof comprise light chain CDR sequences as set forth in SEQ ID Nos: 107, 109, and 111 (CDR1, CDR2, and CDR3), or CDR sequences comprising one or more substitutions in the sequences as set forth in SEQ ID Nos: 107, 109, and 111 (CDR1, CDR2, and CDR3). In some cases, the humanized AGX-A07 antibodies or antigen binding fragments thereof comprise light chain CDR sequences as set forth in SEQ ID Nos: 108, 109, and 110 (CDR1, CDR2, and CDR3), or CDR sequences comprising one or more substitutions in the sequences as set forth in SEQ ID Nos: 108, 109, and 110 (CDR1, CDR2, and CDR3). In some cases, the humanized AGX-A07 antibodies or antigen binding fragments thereof comprise light chain CDR sequences as set forth in SEQ ID Nos: 108, 109, and 111 (CDR1, CDR2, and CDR3), or CDR sequences comprising one or more substitutions in the sequences as set forth in SEQ ID Nos: 108, 109, and 111 (CDR1, CDR2, and CDR3).

In some cases, the humanized mutated AGX-A07 antibodies or antigen binding fragments thereof comprise light chain CDR1 sequence as set forth in SEQ ID Nos: 107 or 108, or light chain CDR1 sequence comprising one or more substitutions in the sequences as set forth in SEQ ID Nos: 107 or 108. In some cases, the humanized mutated AGX-A07 antibodies or antigen binding fragments thereof comprise light chain CDR2 sequence as set forth in SEQ ID NO: 109, or light chain CDR2 sequence comprising one or more substitutions in the sequences as set forth in SEQ ID NO: 109. In some cases, the humanized mutated AGX-A07 antibodies or antigen binding fragments thereof comprise light chain CDR3 sequence as set forth in SEQ ID Nos: 110 or 111, or light chain CDR1 sequence comprising one or more substitutions in the sequences as set forth in SEQ ID Nos: 110 or 111. In some cases, the humanized mutated AGX-A07 antibodies or antigen binding fragments thereof comprise light chain CDR3 sequence as set forth in SEQ ID NO: 110, or light chain CDR1 sequence comprising one or more substitutions in the sequences as set forth in SEQ ID Nos: 110.

In some embodiments, the humanized mutated AGX-A07 comprises a heavy chain variable region comprising the following amino acid substitutions: Q1E, D44G, F80Y in SEQ ID NO: 132 (also referred to herein as AGX-A07 H2), and a light chain variable region comprising the following amino acid substitutions: I3V, N26Q, G62S in SEQ ID NO: 133 (also referred to herein as AGX-A07 L5). In some embodiments, the humanized mutated AGX-A07 comprises a heavy chain variable region comprising the following amino acid substitutions: Q1E, D44G, F80Y in SEQ ID NO: 132, and a light chain variable region comprising the following amino acid substitutions: I3V, N26Q, G62S in SEQ ID NO: 133, wherein the heavy chain comprises CDR1 (SEQ ID NO: 94), CDR2 (SEQ ID NO: 95), and CDR3 (SEQ ID NO: 96), and the light chain comprises CDR1 (SEQ ID NO: 108), CDR2 (SEQ ID NO: 109), and CDR3 (SEQ ID NO: 110). In some embodiments, the humanized mutated AGX-A07 is AGX-A07 H2v1L5v2 and comprises a heavy chain comprising the amino acid sequence as set forth in SEQ ID NO: 130 (also referred to herein as AGX-A07 H2v1), and a light chain comprising the amino acid sequence as set forth in SEQ ID NO: 131 (also referred to herein as AGX-A07 L5v2). In some embodiments, the humanized mutated AGX-A07 comprises a heavy chain comprising the amino acid sequence as set forth in SEQ ID NO: 92, and a light chain comprising the amino acid sequence as set forth in SEQ ID NO: 101.

The amino acid sequences of murine monoclonal antibody AGX-A08 are described in Table 2. Specifically, the heavy chain CDR sequences are set forth in SEQ ID Nos: 54, 55, and 56 (CDR1, CDR2, and CDR3), and the light chain CDR amino acid sequences are set forth in SEQ ID Nos: 60, 61, and 62 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 54, 55, and 56 and/or a light chain variable region comprising CDRs as set forth in the amino acid sequences of SEQ ID Nos: 60, 61, and 62. Included in the disclosure are humanized antibodies or antigen binding fragments comprising the CDRs of AGX-A08. Further, the heavy chain variable amino acid sequences and the light chain variable amino acid sequences of AGX-A08 are described in SEQ ID NOs: 51 and 57, respectively.

The amino acid sequences of murine monoclonal antibody AGX-A09 are described in Table 2. Specifically, the heavy chain CDR sequences are set forth in SEQ ID Nos: 66, 67, and 68 (CDR1, CDR2, and CDR3), and the light chain CDR amino acid sequences are set forth in SEQ ID Nos: 72, 73, and 74 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 66, 67, and 68 and/or a light chain variable region comprising CDRs as set forth in the amino acid sequences of SEQ ID Nos: 72, 73, and 74. Included in the disclosure are humanized antibodies or antigen binding fragments comprising the CDRs of AGX-A09. Further, the heavy chain variable amino acid sequences and the light chain variable amino acid sequences of AGX-A09 are described in SEQ ID NOs: 63 and 69, respectively.

The amino acid sequences of murine monoclonal antibody AGX-A11 are described in Table 2. Specifically, the heavy chain CDR sequences are set forth in SEQ ID Nos: 78, 79, and 80 (CDR1, CDR2, and CDR3), and the light chain CDR amino acid sequences are set forth in SEQ ID Nos: 84, 85, and 86 (CDR1, CDR2, and CDR3). Included in the disclosure are anti-TM4SF1 antibodies, or antigen binding fragments comprising a heavy chain variable region comprising CDRs as set forth in the amino acid sequences of SEQ ID Nos: 78, 79, and 80 and/or a light chain variable region comprising CDRs as set forth in the amino acid sequences of SEQ ID Nos: 84, 85, and 862. Included in the disclosure are humanized antibodies or antigen binding fragments comprising the CDRs of AGX-A11. Further, the heavy chain variable amino acid sequences and the light chain variable amino acid sequences of AGX-A11 are described in SEQ ID NOS: 75 and 81, respectively.

The amino acid sequences of a humanized antibody AGX-A01 (h AGX-A01) are described in Table 2. As shown in Table 2, the heavy chain sequence set forth is SEQ ID NO: 112 is also referred to herein as AGX-A01 H1. Specifically, the heavy chain CDR sequences are set forth in SEQ ID Nos: 115, 116, and 118 (CDR1, CDR2, and CDR3) and the light chain CDR amino acid sequences are set forth in SEQ ID Nos: 124, 128, and 129 (CDR1, CDR2, and CDR3). Further, exemplary heavy chain amino acid sequence and the light chain amino acid sequence of the humanized AGX-A01 are described in SEQ ID Nos: 112 and 122, respectively. Exemplary coding sequences for the heavy chain and the light chain of the humanized AGX-A01 are described in SEQ ID Nos: 113 and 123, respectively In some embodiments, the humanized AGX-A01 antibody or antigen binding fragments thereof is a humanized mutated AGX-A01 (hm AGX-A01) antibody or antigen binding fragments thereof, comprising a heavy chain sequence comprising one or more substitutions in the sequence as set forth in the amino acid sequence of SEQ ID NO: 112. In some embodiments, the humanized AGX-A01 antibody or antigen binding fragments thereof is a humanized mutated AGX-A01 antibody or antigen binding fragments thereof, comprising a heavy chain sequence comprising one or more substitutions in the sequence as set forth in the amino acid sequence of SEQ ID NO: 112, wherein the one or more substitutions are in amino acid positions 63 and 106 of SEQ ID NO: 112. In some cases, the humanized mutated AGX-A01 antibody or antigen binding fragments thereof comprises a G63S (glycine to serine substitution at position 63 of the heavy chain, SEQ ID NO: 112). In some cases, the humanized mutated AGX-A01 antibody or antigen binding fragments thereof comprises a D106E (aspartate to glutamic acid substitution at position 106 of the heavy chain, SEQ ID NO: 112). In some cases, the humanized mutated AGX-A01 antibody or antigen binding fragments thereof comprises a D106S (aspartate to serine substitution at position 106 of the heavy chain, SEQ ID NO: 112). In some embodiments, a humanized mutated AGX-A01 antibody or antigen binding fragments is provided, comprising a heavy chain sequence as forth in the amino acid sequence of SEQ ID NO: 114. As shown in Table 2, the heavy chain sequence set forth is SEQ ID NO: 114 is also referred to herein as AGX-A01 H1v1.

In some embodiments, humanized AGX-A01 antibodies or antigen binding fragments are provided, comprising a light chain sequence as forth in the amino acid sequence of SEQ ID NO: 122. As shown in Table 2, the light chain sequence set forth is SEQ ID NO: 122 is also referred to herein as AGX-A01 L10. In some embodiments, the humanized AGX-A01 antibody or antigen binding fragments thereof is a humanized mutated AGX-A01 antibody or antigen binding fragments thereof, comprising a light chain sequence comprising one or more substitutions in the sequence as set forth in the amino acid sequence of SEQ ID NO: 122. In some embodiments, the humanized mutated AGX-A01 antibody or antigen binding fragments thereof is a humanized mutated AGX-A01 antibody or antigen binding fragments thereof, comprising a light chain sequence comprising one or more substitutions in the sequence as set forth in the amino acid sequence of SEQ ID NO: 122, wherein the one or more substitutions are in one or more amino acid positions selected from amino acid positions 1, 33, 42, 51, 86, and 90 of SEQ ID NO: 122. In some embodiments, the humanized mutated AGX-A01 antibody or antigen binding fragments thereof is a humanized mutated AGX-A01 antibody or antigen binding fragments thereof, comprising a light chain sequence comprising one or more substitutions in the sequence as set forth in the amino acid sequence of SEQ ID NO: 122, wherein the one or more substitutions are in one or more amino acid positions selected from amino acid positions 1, 33, 42, 51, and 86 of SEQ ID NO: 122. In some cases, the humanized mutated AGX-A01 antibody or antigen binding fragments thereof comprises an A1E (alanine to glutamic acid substitution at position 1 of the light chain, SEQ ID NO: 122). In some cases, the humanized mutated AGX-A01 antibody or antigen binding fragments thereof comprises a N33 S (asparagine to serine substitution at position 33 of the light chain, SEQ ID NO: 122). In some cases, the humanized mutated AGX-A01 antibody or antigen binding fragments thereof comprises a M42Q (methionine to glutamine substitution at position 42 of the light chain, SEQ ID NO: 122). In some cases, the humanized mutated AGX-A01 antibody or antigen binding fragments thereof comprises a V51L (valine to leucine substitution at position 51 of the light chain, SEQ ID NO: 122). In some cases, the humanized mutated AGX-A01 antibody or antigen binding fragments thereof comprises a D86E (aspartate to glutamic acid substitution at position 86 of the light chain, SEQ ID NO: 122). In some cases, the humanized mutated AGX-A01 antibody or antigen binding fragments thereof comprises an I90V (isoleucine to valine substitution at position 90 of the light chain, SEQ ID NO: 122).

In some cases, the humanized AGX-A01 antibodies or antigen binding fragments thereof comprise heavy chain CDR sequences as set forth in SEQ ID Nos: 115 (CDR1); 116 (CDR2); and 118 (CDR3), or CDR sequences comprising one or more substitutions in the sequences as set forth in SEQ ID Nos: 115 (CDR1); 116 (CDR2); and 118 (CDR3). In some cases, the humanized mutated AGX-A01 antibodies or antigen binding fragments thereof comprise heavy chain CDR sequences as set forth in SEQ ID Nos: 115 (CDR1); 116 or 117 (CDR2); and 118, 119, 120, or 121 (CDR3), or CDR sequences comprising one or more substitutions in the sequences as set forth in SEQ ID Nos: 115 (CDR1); 116 or 117 (CDR2); and 118, 119, 120, or 121 (CDR3).

In some cases, the humanized mutated AGX-A01 antibodies or antigen binding fragments thereof comprise heavy chain CDR1 sequence as set forth in SEQ ID NO: 115, or a heavy chain CDR1 sequence comprising one or more substitutions in the sequences as set forth in SEQ ID NO: 115. In some cases, the humanized mutated AGX-A01 antibodies or antigen binding fragments thereof comprise a heavy chain CDR2 sequence as set forth in SEQ ID NO: 116, or a heavy chain CDR2 sequence comprising one or more substitutions in the sequences as set forth in SEQ ID NO: 116. In some cases, the humanized mutated AGX-A01 antibodies or antigen binding fragments thereof comprise a heavy chain CDR2 sequence as set forth in SEQ ID NO: 117, or a heavy chain CDR2 sequence comprising one or more substitutions in the sequences as set forth in SEQ ID NO: 117. In some cases, the humanized mutated AGX-A01 antibodies or antigen binding fragments thereof comprise a heavy chain CDR3 sequence as set forth in a sequence selected from SEQ ID Nos: 118, 119, 120 and 121, or a heavy chain CDR3 sequence comprising one or more substitutions in a sequence selected from SEQ ID Nos: 118, 119, 120, and 121.

In some cases, the humanized AGX-A01 antibodies or antigen binding fragments thereof comprise light chain CDR sequences as set forth in SEQ ID Nos: 124 (CDR1); 128 (CDR2); and 129 (CDR3), or CDR sequences comprising one or more substitutions in the sequences as set forth in SEQ ID Nos: 124 (CDR1); 128 (CDR2); and 129 (CDR3). In some cases, the humanized mutated AGX-A01 antibodies or antigen binding fragments thereof comprise light chain CDR sequences as set forth in SEQ ID Nos: 124, 125, 126, or 127 (CDR1); 128 (CDR2); and 129 (CDR3), or CDR sequences comprising one or more substitutions in the sequences as set forth in SEQ ID Nos: 124, 125, 126, or 127 (CDR1); 128 (CDR2); and 129 (CDR3).

In some cases, the humanized mutated AGX-A01 antibodies or antigen binding fragments thereof comprise light chain CDR1 sequence as set forth in SEQ ID Nos: 125, 126, 127, or 128, or light chain CDR1 sequence comprising one or more substitutions in the sequences as set forth in SEQ ID Nos: 125, 126, 127, or 128. In some cases, the humanized mutated AGX-A01 antibodies or antigen binding fragments thereof comprise light chain CDR2 sequence as set forth in SEQ ID NO: 129, or light chain CDR2 sequence comprising one or more substitutions in the sequences as set forth in SEQ ID NO: 129. In some cases, the humanized mutated AGX-A01 antibodies or antigen binding fragments thereof comprise light chain CDR3 sequence as set forth in SEQ ID Nos: 130, or light chain CDR1 sequence comprising one or more substitutions in the sequences as set forth in SEQ ID Nos: 130.

In one embodiment, the disclosure provides an anti-TM4SF1 antibody, or antigen-binding fragment thereof, that comprises a heavy chain variable domain encoded by a nucleic acid sequence as set forth in SEQ ID NO: 3, and a light chain variable domain encoded by a nucleic acid sequence as set forth in SEQ ID NO: 9. In one embodiment, the disclosure provides an anti-TM4SF1 antibody, or antigen-binding fragment thereof, that comprises a heavy chain variable domain encoded by a nucleic acid sequence as set forth in SEQ ID NO: 15, and a light chain variable domain encoded by a nucleic acid sequence as set forth in SEQ ID NO: 21 In one embodiment, the disclosure provides an anti-TM4SF1 antibody, or antigen-binding fragment thereof, that comprises a heavy chain variable domain encoded by a nucleic acid sequence as set forth in SEQ ID NO: 27, and a light chain variable domain encoded by a nucleic acid sequence as set forth in SEQ ID NO: 33. In one embodiment, the disclosure provides an anti-TM4SF1 antibody, or antigen-binding fragment thereof, that comprises a heavy chain variable domain encoded by a nucleic acid sequence as set forth in SEQ ID NO: 39, and a light chain variable domain encoded by a nucleic acid sequence as set forth in SEQ ID NO: 45. In one embodiment, the disclosure provides an anti-TM4SF1 antibody, or antigen-binding fragment thereof, that comprises a heavy chain variable domain encoded by a nucleic acid sequence as set forth in SEQ ID NO: 51, and a light chain variable domain encoded by a nucleic acid sequence as set forth in SEQ ID NO: 57. In one embodiment, the disclosure provides an anti-TM4SF1 antibody, or antigen-binding fragment thereof, that comprises a heavy chain variable domain encoded by a nucleic acid sequence as set forth in SEQ ID NO: 63, and a light chain variable domain encoded by a nucleic acid sequence as set forth in SEQ ID NO: 69. In one embodiment, the disclosure provides an anti-TM4SF1 antibody, or antigen-binding fragment thereof, that comprises a heavy chain variable domain encoded by a nucleic acid sequence as set forth in SEQ ID NO: 75, and a light chain variable domain encoded by a nucleic acid sequence as set forth in SEQ ID NO: 81. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 97. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 99. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 101. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 103. In one embodiment, the disclosure provides an anti-TM4SF1 antibody, or antigen-binding fragment thereof, that comprises a heavy chain variable domain encoded by a nucleic acid sequence as set forth in SEQ ID NO: 90, and a light chain variable domain encoded by a nucleic acid sequence as set forth in SEQ ID NO: 105. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 97. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 99. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 101. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 103. In one embodiment, the disclosure provides an anti-TM4SF1 antibody, or antigen-binding fragment thereof, that comprises a heavy chain variable domain encoded by a nucleic acid sequence as set forth in SEQ ID NO: 92, and a light chain variable domain encoded by a nucleic acid sequence as set forth in SEQ ID NO: 105.

In one embodiment, the present disclosure provides an anti-TM4SF1 antibody, or antigen-binding fragment thereof, that has a heavy chain variable domain sequence that is at least 95% identical, at least 96% identical, at least 97% identical, at least 98% identical, at least 99% identical, or 100% identical to an amino acid sequence selected from SEQ ID NO: 3, SEQ ID NO: 15, SEQ ID NO: 27, SEQ ID NO: 39, SEQ ID NO: 51, SEQ ID NO: 63, SEQ ID NO: 75, SEQ ID NO: 90, SEQ ID NO: 92, SEQ ID NO: 112, or SEQ ID NO: 114; and that has a light chain variable domain sequence that is at least 95% identical, at least 96% identical, at least 97% identical, at least 98% identical, at least 99% identical, or 100% identical to an amino acid sequence selected from SEQ ID NO: 9, SEQ ID NO: 21, SEQ ID NO: 33, SEQ ID NO: 45, SEQ ID NO: 57, SEQ ID NO: 69, SEQ ID NO: 81, SEQ ID NO: 97, SEQ ID NO: 99, SEQ ID NO: 101, SEQ ID NO: 103, SEQ ID NO: 105, or SEQ ID NO: 122. In one embodiment, the present disclosure provides an anti-TM4SF1 antibody, or antigen-binding fragment thereof, that has a heavy chain variable domain sequence that is at least 95% identical, at least 96% identical, at least 97% identical, at least 98% identical, at least 99% identical, or 100% identical to an amino acid sequence selected from SEQ ID NO: 3, SEQ ID NO: 15, SEQ ID NO: 27, SEQ ID NO: 39, SEQ ID NO: 51, SEQ ID NO: 63, SEQ ID NO: 75, SEQ ID NO: 90, SEQ ID NO: 92, SEQ ID NO: 112, or SEQ ID NO: 114; and that has a light chain variable domain sequence that is at least 95% identical, at least 96% identical, at least 97% identical, at least 98% identical, at least 99% identical, or 100% identical to an amino acid sequence selected from SEQ ID NO: 9, SEQ ID NO: 21, SEQ ID NO: 33, SEQ ID NO: 45, SEQ ID NO: 57, SEQ ID NO: 69, SEQ ID NO: 81, SEQ ID NO: 97, SEQ ID NO: 99, SEQ ID NO: 101, or SEQ ID NO: 122.

In one embodiment, the disclosure includes an anti-TM4SF1 antibody which is an IgG and comprises four polypeptide chains including two heavy chains each comprising a heavy chain variable domain and heavy chain constant regions CH1, CH2 and CH3, and two light chains each comprising a light chain variable domain and a light chain constant region (CL). In certain embodiments, the antibody is a human IgG1, IgG2, or an IgG4. In certain embodiments, the antibody is a human IgG1. In other embodiments, the antibody is an IgG2. The heavy and light chain variable domain sequences may contain CDRs as set forth in Table 2.

Complementarity determining regions (CDRs) are known as hypervariable regions both in the light chain and the heavy chain variable domains. The more highly conserved portions of variable domains are called the framework (FR). CDRs and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences, including the identification of CDRs, that is applicable to any antibody.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest. The CDR3, in particular, is known to play an important role in antigen binding of an antibody or antibody fragment.

In one embodiment, the disclosure provides an anti-TM4SF1 antibody, or an antigen-binding fragment thereof, comprising a heavy chain comprising a CDR3 domain as set forth in any one of SEQ ID NO: 8, SEQ ID NO: 20, SEQ ID NO: 32, SEQ ID NO: 44, SEQ ID NO: 56, SEQ ID NO: 68, or SEQ ID NO: 80 and comprising a variable domain comprising an amino acid sequence that has at least about 60%, at least about 65%, at least about 70%, at least about 75%, at least about 80%, at least about 85%, at least about 90%, at least about 95%, at least about 96%, at least about 97%, at least about 98%, at least about 99%, or 100% identical to a sequence as set forth in any one of SEQ ID NO: 3, SEQ ID NO: 15, SEQ ID NO: 27, SEQ ID NO: 39, SEQ ID NO: 51, SEQ ID NO: 63, or SEQ ID NO: 75. In one embodiment, the disclosure provides an anti-TM4SF1 antibody, or an antigen-binding fragment thereof, comprising a light chain comprising a CDR3 domain as set forth in any one of SEQ ID NO: 14, SEQ ID NO: 26, SEQ ID NO: 38, SEQ ID NO: 50, SEQ ID NO: 62, SEQ ID NO: 74, or SEQ ID NO: 86, and having a light chain variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 9, SEQ ID NO: 21, SEQ ID NO: 33, SEQ ID NO: 45, SEQ ID NO: 57, SEQ ID NO: 69, or SEQ ID NO: 81. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to TM4SF1 and retains the functional characteristics, e.g., binding affinity, of the parent, or has improved functional characteristic, e.g., binding affinity, compared to the parent. In one embodiment, the disclosure provides an anti-TM4SF1 antibody, or an antigen-binding fragment thereof, comprising a heavy chain comprising a CDR2 domain as set forth in any one of SEQ ID NO: 7, SEQ ID NO: 19, SEQ ID NO: 31, SEQ ID NO: 43, SEQ ID NO: 55, SEQ ID NO: 67, or SEQ ID NO: 79 and comprising a variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 3, SEQ ID NO: 15, SEQ ID NO: 27, SEQ ID NO: 39, SEQ ID NO: 51, SEQ ID NO: 63, or SEQ ID NO: 75. In one embodiment, the disclosure provides an anti-TM4SF1 antibody, or an antigen-binding fragment thereof, comprising a light chain comprising a CDR2 domain as set forth in any one of SEQ ID NO: 13, SEQ ID NO: 25, SEQ ID NO: 37, SEQ ID NO: 49, SEQ ID NO: 61, SEQ ID NO: 73, or SEQ ID NO: 85, and having a light chain variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 9, SEQ ID NO: 21, SEQ ID NO: 33, SEQ ID NO: 45, SEQ ID NO: 57, SEQ ID NO: 69, or SEQ ID NO: 81. Thus, in certain embodiments, the CDR2 domain is held constant, while variability may be introduced into the remaining CDRs and/or framework regions of the heavy and/or light chains, while the antibody, or antigen binding fragment thereof, retains the ability to bind to TM4SF1 and retains the functional characteristics, e.g., binding affinity, of the parent, or has improved functional characteristic, e.g., binding affinity, compared to the parent.

In one embodiment, the disclosure provides an anti-TM4SF1 antibody, or an antigen-binding fragment thereof, comprising a heavy chain comprising a CDR1 domain as set forth in any one of SEQ ID NO: 6, SEQ ID NO: 18, SEQ ID NO: 30, SEQ ID NO: 42, SEQ ID NO: 54, SEQ ID NO: 66, or SEQ ID NO: 78 and comprising a variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence as set forth in any one of SEQ ID NO: 3, SEQ ID NO: 15, SEQ ID NO: 27, SEQ ID NO: 39, SEQ ID NO: 45, SEQ ID NO: 69, or SEQ ID NO: 81. In one embodiment, the disclosure provides an anti-TM4SF1 antibody, or an antigen-binding fragment thereof, comprising a light chain comprising a CDR1 domain as set forth in any one of SEQ ID NO: 12, SEQ ID NO: 24, SEQ ID NO: 36, SEQ ID NO: 48, SEQ ID NO: 60, SEQ ID NO: 72, or SEQ ID NO: 84, and having a light chain variable domain comprising an amino acid sequence that has at least at least about 60%, at least about 65%, at least about 70%, at least about 75%, at least about 80%, at least about 85%, at least about 90%, at least about 95%, at least about 96%, at least about 97%, at least about 98%, or at least about 99%, or 100% identical to a sequence a set forth in any one of SEQ ID NO: 9, SEQ ID NO: 21, SEQ ID NO: 33, SEQ ID NO: 45, SEQ ID NO: 57, SEQ ID NO: 69, or SEQ ID NO: 81. Thus, in certain embodiments, the CDR1 domain is held constant, while variability may be introduced into the remaining CDRs and/or framework regions of the heavy and/or light chains, while the antibody, or antigen binding fragment thereof, retains the ability to bind to TM4SF1 and retains the functional characteristics, e.g., binding affinity, of the parent.

The anti-TM4SF1 antibodies and fragments described in Table 2 may also be humanized. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332:323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the six CDRs of the parent non-human antibody (e.g., rodent) are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (see, e.g., Kashmiri et al., 2005, Methods 36:25-34).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al., 1993, J. Immunol. 151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human subclasses, VL6 subgroup I (VL6 I) and VH subgroup III (VHIII). In another method, human germline genes are used as the source of the framework regions.

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human framework regions that may be used for humanization include but are not limited to: framework regions selected using the "best-fit" method (see, e.g., Sims, et al., J. Immunol. 151 (1993) 2296); framework regions derived from the consensus sequence of human antibodies of a particular subgroup of light or heavy chain variable regions (see, e.g., Carter, et al., Proc. Natl. Acad. Sci. USA, 89 (1992) 4285; and Presta, et al., J. Immunol., 151 (1993) 2623); human mature (somatically mutated) framework regions or human germline framework regions (see, e.g., Almagro, and Fransson, Front. Biosci. 13 (2008) 1619-1633); and framework regions derived from screening FR libraries (see, e.g., Baca, et al., J. Biol. Chem. 272 (1997) 10678-10684 and Rosok, et al., J. Biol. Chem. 271 (1996) 22611-22618).

Humanized antibodies and methods of making them are reviewed, e.g., in Almagro, and Fransson, Front. Biosci. 13 (2008) 1619-1633, and are further described, e.g., in Riechmann, et al., Nature 332 (1988) 323-329; Queen, et al., Proc. Nat'l Acad. Sci. USA 86 (1989) 10029-10033; U.S. Pat. Nos. 5,821,337, 7,527,791, 6,982,321, and 7,087,409; Kashmiri, et al., Methods 36 (2005) 25-34 (describing SDR (a-CDR) grafting); Padlan, Mol. Immunol. 28 (1991) 489-498 (describing "resurfacing"); Dall'Acqua, et al., Methods 36 (2005) 43-60 (describing "FR shuffling"); and Osbourn, et al., Methods 36 (2005)61-68 and Klimka, et al., Br. J. Cancer, 83 (2000) 252-260 (describing the "guided selection" approach to FR shuffling).

In some embodiments, the TM4SF1 binding protein, such as an anti-TM4SF1 antibody or an antigen binding fragment thereof is naked, unconjugated, and/or unmodified. In some embodiments, the binding protein further includes an agent. In some embodiments, the agent is a therapeutic agent or a diagnostic agent. In some embodiments, the therapeutic agent is a biologically active moiety. In some embodiments, the biologically active moiety comprises a cytotoxic agent, a chemotherapeutic agent, a protein, a peptide, an antibody, a growth inhibitory agent, and an anti-hormonal agent. In some embodiments, the cytotoxic agent comprises a ribosome inactivating protein, a histone deacetylase (HDAC) inhibitor, a tubulin inhibitor, an alkylating agent, an antibiotic, an antineoplastic agent, an antiproliferative agent, an antimetabolite, a topoisomerase I or II inhibitor, a hormonal agonist or antagonist, an immunomodulator, a DNA minor groove binder, and a radioactive agent. In certain embodiments, the ribosome inactivating protein is saporin. In some embodiments, the diagnostic agent is a label. In some embodiments, the label is a fluorescent label, a chromogenic label, or a radiolabel. In some embodiments, the agent is directly conjugated to the TM4SF1 binding protein. In other embodiments, the agent is indirectly conjugated to the TM4SF1 binding protein, optionally by a linker.

In some embodiments, a TM4SF1 binding protein of the disclosure is a conjugate (i.e., a conjugated binding protein), which further includes one or more agents (e.g., 1, 2, 3, or 4 or more agents), such as therapeutic agents, that act additively or synergistically with the TM4SF1 binding protein, for example, to kill or inhibit tumor cells (TCs) and/or tumor vasculature endothelial cells (ECs) in the treatment of a disorder associated with pathological angiogenesis, such as cancer. The therapeutic agent, for example, can be a biologically active moiety, such as a cytotoxic agent, a chemotherapeutic agent, a protein, a peptide, an antibody, a growth inhibitory agent, and/or an anti-hormonal agent.

Examples of tubulin inhibitors that can be conjugated, either directly or indirectly, to a the TM4SF1 binding protein of the disclosure include, without limitation, polymerization inhibitors (e.g., vinblastine, vincristine, vinorelbine, vinflunine, cryptophycin 52, hallchondrins, dolastatins, hemiasterlins that can bind to the vinca domain of tubulin; colchine, combretastatins, 2-methoxy-estradiol, E7010 that can bind to the cholchicine domain of tubulin; depolymerization inhibitors, such as paclitaxel, docetaxel, epothilon, discodermolide that can bind to the taxane site).

Exemplary chemotherapeutic agents include, but are not limited to, methotrexate, adriamicin, vinca alkaloids (vincristine, vinblastine, etoposide), doxorubicin, melphalan, mitomycin C, chlorambucil, daunorubicin or other intercalating agents; enzymes and fragments thereof such as nucleolytic enzymes, antibiotics, and toxins such as small molecule toxins or enzymatically active toxins of bacterial, fungal, plant or animal origin, including fragments and/or variants thereof. Enzymatically active toxins and fragments thereof that can be used include diphtheria A chain, non-binding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes.

In addition, a variety of radionuclides can be used for conjugation to the TM4SF1 binding proteins of the disclosure. Examples include $At^{211}$, $I^{131}$, $I^{25}$, $Y^{90}$, $Re^{186}$, $Sm^{153}$, $Bi^{212}$, $P^{32}$, and radioactive isotopes of Lu. Alternatively, the TM4SF1 binding proteins of the disclosure can be conjugated to one or smaller molecule toxins, such as a calicheamicin, maytansinoids, dolastatins, aurostatins, a trichothecene, and CC1065, and the derivatives of these toxins that have toxin activity, are also contemplated herein. Other therapeutic agents that can be conjugated to TM4SF1 binding protein of the disclosure include, in various example, BCNU, streptozoicin, vincristine and 5-fluorouracil etc.

The diagnostic agent for conjugation, in some embodiments, is a label, such as a fluorescent label, a chromogenic label, or a radiolabel. Accordingly, the label may be used for detection purposes, and may be a fluorescent compound, an enzyme, a prosthetic group, a luminescent material, a bioluminescent material, or a radioactive material. The radiolabel, for example, may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The one or more agents (e.g., therapeutic agents and/or diagnostic agents) may be directly conjugated to a TM4SF1 binding protein of the disclosure (e.g., by way of a direct covalent or non-covalent interaction), such that the agent is immediately conjugated to the protein. An agent may be directly conjugated to a binding protein of the disclosure, for example, by a direct peptide bond. In other instances, the direct conjugation is by way of a direct non-covalent interaction, such as an interaction between the TM4SF1 binding protein of the disclosure and an agent that specifically binds to the TM4SF1 binding protein (e.g., an antibody agent).

The one or more agents (e.g., therapeutic agents and/or diagnostic agents) may be indirectly conjugated to a TM4SF1 binding protein of the disclosure (e.g., by way of a linker with direct covalent or non-covalent interactions). Linkers can be chemical linking agents, such as homobifunctional and heterobifunctional cross-linkers, which are available from many commercial sources. Regions available for cross-linking may be found on the binding protein (e.g., anti-TM4SF1 antibodies) of the disclosure. The linker may comprise a flexible arm, e.g., 2, 3, 4, 5, 6, 7, 8, 9, 10, 11, 12, 13, 14, or 15 carbon atoms. Exemplary linkers include BS3 ([Bis(sulfosuccinimidyl)suberate]; BS3 is a homobifunctional N-hydroxysuccinimideester that targets accessible primary amines), NHS/EDC (N-hydroxysuccinimide and N-ethyl-(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups). To form covalent bonds, a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA). Primary amines are the principal targets for NHS esters. Accessible a-amino groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the disclosure, the functional group on the protein will be a thiol group and the chemically reactive group will be a maleimido-containing group such as gamma-maleimide-butrylamide (GMBA or MPA). Such maleimide containing groups are referred to herein as maleido groups. The maleimide group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide can be used. In some cases, the linker can be a single amino acid (e.g., any amino acid, such as Gly or Cys). Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a NE-acylated lysine residue.

In one embodiment, an anti-TM4SF1 antibody, or antigen-binding fragment thereof, of the disclosure binds to cynomolgus TM4SF1 with a $K_D$ about $1 \times 10^{-6}$ M or less.

An anti-TM4SF1 antibody, or antigen-binding fragment thereof, of the disclosure, in certain embodiments, binds to an epitope on the ECL2 loop of human TM4SF1 with a $K_D$ about $5 \times 10^{-8}$ M or less as determined in a standard flow cytometry assay using HUVEC cells.

An anti-TM4SF1 antibody, or antigen-binding fragment thereof, of the disclosure, in certain embodiments, binds to human TM4SF1 with a $K_D$ of about $1 \times 10^{-8}$ M or less in a standard flow cytometry assay using HUVEC cells.

An anti-TM4SF1 antibody, or antigen-binding fragment thereof, of the disclosure, in certain embodiments, binds to human TM4SF1 with a $K_D$ of about $1 \times 10^{-3}$ M to about $1 \times 10^{-4}$ M, about $1 \times 10^{-4}$ M to about $1 \times 10^{-5}$ M, about $1 \times 10^{-5}$ M to about $1 \times 10^{-5}6$ M, about $1 \times 10^{-6}$ to about $1 \times 10^{-7}$ M, about $1 \times 10^{-7}$ to about $1 \times 10^{-8}$ M, about $1 \times 10^{-8}$ M to about $1 \times 10^{-9}$ M, about $1 \times 10^{-9}$ M to about $1 \times 10^{-10}$ M, about $1 \times 10^{-10}$ M to about $1 \times 10^{-11}$ M, about $1 \times 10^{-11}$ M to about $1 \times 10^{-12}$ M, about $2 \times 10^{-3}$ M to about $2 \times 10^{-4}$ M, about $2 \times 10^{-4}$ M to about $2 \times 10^{-5}$ M, about $2 \times 10^{-5}$ M to about $2 \times 10^{-6}$ M, about $2 \times 10^{-6}$ to about $2 \times 10^{-7}$ M, about $2 \times 10^{-7}$ to about $2 \times 10^{-8}$ M, about $2 \times 10^{-8}$ M to about $2 \times 10^{-9}$ M, about $2 \times 10^{-9}$ M to about $2 \times 10^{-10}$ M, about $2 \times 10^{-10}$ M to about $2 \times 10^{-11}$ M, about $2 \times 10^{-11}$ M to about $2 \times 10^{-12}$ M, about $3 \times 10^{-3}$ M to about $3 \times 10^{-4}$ M, about $3 \times 10^{-4}$ M to about $3 \times 10^{-5}$ M, about $3 \times 10^{-5}$ M to about $3 \times 10^{-6}$ M, about $3 \times 10^{-6}$ to about $3 \times 10^{-7}$ M, about $3 \times 10^{-7}$ to about $3 \times 10^{-8}$ M, about $3 \times 10^{-8}$ M to about $3 \times 10^{-9}$ M, about $3 \times 10^{-9}$ M to about $3 \times 10^{-10}$ M, about $3 \times 10^{-10}$ M to about $3 \times 10^{-11}$ M, about $3 \times 10^{-11}$ M to about $3 \times 10^{-12}$ M, about $4 \times 10^{-3}$ M to about $4 \times 10^{-4}$ M, about $4 \times 10^{-4}$ M to about $4 \times 10^{-5}$ M, about $4 \times 10^{-5}$ M to about $4 \times 10^{-6}$ M, about $4 \times 10^{-6}$ to about $4 \times 10^{-7}$ M, about $4 \times 10^{-7}$ to about $4 \times 10^{-8}$ M, about $4 \times 10^{-8}$ M to about $4 \times 10^{-9}$ M, about $4 \times 10^{-9}$ M to about $4 \times 10^{-10}$ M, about $4 \times 10^{-10}$ M to about $4 \times 10^{-11}$ M, about $4 \times 10^{-11}$ M to about $4 \times 10^{-12}$ M, about $5 \times 10^{-3}$ M to about $5 \times 10^{-4}$ M, about $5 \times 10^{-4}$ M to about $5 \times 10^{-5}$ M, about $5 \times 10^{-5}$ M to about $5 \times 10^{-6}$ M, about $5 \times 10^{-6}$ to about $5 \times 10^{-7}$ M, about $5 \times 10^{-7}$ to about $5 \times 10^{-8}$ M, about $5 \times 10^{-8}$ M to about $5 \times 10^{-9}$ M, about $5 \times 10^{-9}$ M to about $5 \times 10^{-10}$ M, about $5 \times 10^{-10}$M to about $5 \times 10^{-11}$ M, about $5 \times 10^{-11}$ M to about $5 \times 10^{-12}$ M, about $5 \times 10^{-7}$ M to about $5 \times 10^{-11}$ M, about $5 \times 10^{-7}$ M, about $1 \times 10^{-7}$ M, about $5 \times 10^{-8}$ M, about $1 \times 10^{-8}$ M, about $5 \times 10^{-9}$ M, about $1 \times 10^{-9}$ M, about $5 \times 10^{-10}$ M, about $1 \times 10^{-10}$M, about $5 \times 10^{-11}$ M or about $1 \times 10^{-11}$ M. In some embodiments, the $K_D$ is determined in a standard flow cytometry assay using HUVEC cells.

An anti-TM4SF1 antibody, or antigen-binding fragment thereof, of the disclosure, in certain embodiments, binds to human TM4SF1 with a $K_D$ of about $5 \times 10^{-10}$ M or less in a standard flow cytometry assay using HUVEC cells.

An anti-TM4SF1 antibody, or antigen-binding fragment thereof, of the disclosure, in certain embodiments, binds to cynomolgus TM4SF1 with a $K_D$ about $1 \times 10^{-6}$ M or less in a standard flow cytometry assay using HEK293 overexpressing cells. In one embodiment, the HEK293 cells are transfected to express cynomolgus TM4SF1. In a further embodiment, HEK293 cells express cynomolgus TM4SF1 at about 600 mRNA copies per $10^6$ copies 18S rRNA.

Methods of determining the $K_D$ of an antibody or antibody fragment are known in the art. For example, surface plasmon resonance may be used to determine the $K_D$ of the antibody to the antigen (e.g., using a BIACORE 2000 or a BIACORE 3000 (BIAcore, Inc., Piscataway, N.J.) at 25° C. with immobilized antigen or Fc receptor CM5 chips at about 10 response units (RU)). In certain embodiments FACS or flow cytometry is used to determine the $K_D$, whereby cells, such as HEK293 cells or HUVEC cells, that express TM4SF1 are used to bind the antibody or fragment and measure the $K_D$ according to standard methods. Affinity determination of antibodies using flow cytometry is described, for example, in Geuijen et al (2005) *J Immunol Methods*. 302(1-2):68-77. In certain embodiments, FACS is used to determine affinity of antibodies.

In one embodiment, the disclosure features an anti-TM4SF1 antibody or antigen binding fragment thereof, having CDR amino acid sequences described herein with conservative amino acid substitutions, such that the anti-TM4SF1 antibody or antigen binding fragment thereof comprises an amino acid sequence of a CDR that is at least 95% identical (or at least 96% identical, or at least 97% identical, or at least 98% identical, or at least 99% identical) to a CDR amino acid sequence set forth in Table 2. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

The disclosure further features in one aspect an anti-TM4SF1 antibody, or antigen-binding fragment thereof, that binds to an epitope on the ECL2 loop of human TM4SF1 with a $K_D$ of about $5 \times 10^{-8}$ M or less as determined in a standard flow cytometry assay using HUVEC cells, wherein the anti-TM4SF1 antibody, or antigen-binding fragment thereof, comprises a light chain variable region comprising a human IgG framework region and comprises a heavy chain variable region comprising a human IgG framework region. In one embodiment, the anti-TM4SF1 antibody, or antigen-binding fragment thereof, is humanized. In one embodiment, the anti-TM4SF1 antibody, or antigen-binding fragment thereof, cross reacts with cynomolgus TM4SF1.

In another aspect of the disclosure, the anti-TM4SF1 antibody, or antigen-binding fragment thereof, is a humanized anti-TM4SF1 antibody, or antigen-binding fragment thereof, that binds to an epitope on the ECL2 loop of human TM4SF1 with a $K_D$ about $5 \times 10^{-8}$ M or less as determined in a standard flow cytometry assay using HUVEC cells. In one embodiment, the anti-TM4SF1 antibody, or antigen-binding fragment thereof, binds to cynomolgus TM4SF1 with a $K_D$ about $1 \times 10^{-6}$ M or less in a standard flow cytometry assay using HEK293 overexpressing cells. In one embodiment, the anti-TM4SF1 antibody, or antigen-binding fragment thereof, binds to human TM4SF1 with a $K_D$ of about $1 \times 10^{-8}$ M or less in a standard flow cytometry assay using HUVEC cells. In one embodiment, the anti-TM4SF1 antibody, or antigen-binding fragment thereof, binds to human TM4SF1 with a $K_D$ of $1 \times 10^{-3}$ M to about $1 \times 10^{-4}$ M, about $1 \times 10^{-4}$ M to about $1 \times 10^{-5}$ M, about $1 \times 10^{-5}$ M to about $1 \times 10^{-6}$ M, about $1 \times 10^{-6}$ to about $1 \times 10^{-7}$M, about $1 \times 10^{-7}$ to about $1 \times 10^{-8}$ M, about $1 \times 10^{-8}$ M to about $1 \times 10^{-9}$ M, about $1 \times 10^{-9}$ M to about $1 \times 10^{-10}$ M, about $1 \times 10^{-10}$M to about $1 \times 10^{-11}$ M, about $1 \times 10^{-11}$ M to about $1 \times 10^{-12}$ M, about $2 \times 10^{-3}$ M to about $2 \times 10^{-4}$ M, about $2 \times 10^{-4}$ M to about $2 \times 10^{-5}$ M, about $2 \times 10^{-5}$ M to about $2 \times 10^{-6}$ M, about $2 \times 10^{-6}$ to about $2 \times 10^{-7}$ M, about $2 \times 10^{-7}$ to about $2 \times 10^{-8}$ M, about $2 \times 10^{-8}$ M to about $2 \times 10^{-9}$ M, about $2 \times 10^{-9}$ M to about $2 \times 10^{-10}$ M, about $2 \times 10^{-10}$M to about $2 \times 10^{-11}$ M, about $2 \times 10^{-11}$ M to about $2 \times 10^{-12}$ M, about $3 \times 10^{-3}$ M to about $3 \times 10^{-4}$ M, about $3 \times 10^{-4}$ M to about $3 \times 10^{-5}$ M, about $3 \times 10^{-5}$ M to about $3 \times 10^{-6}$ M, about $3 \times 10^{-6}$ M to about $3 \times 10^{-7}$M, about $3 \times 10^{-7}$ to about $3 \times 10^{-8}$ M, about $3 \times 10^{-8}$ M to about $3 \times 10^{-9}$ M, about $3 \times 10^{-9}$ M to about $3 \times 10^{-10}$ M, about $3 \times 10^{-10}$M to about $3 \times 10^{-11}$ M, about $3 \times 10^{-11}$ M to about $3 \times 10^{-12}$ M, about $4 \times 10^{-3}$ M to about $4 \times 10^{-4}$ M, about $4 \times 10^{-4}$ M to about $4 \times 10^{-5}$ M, about $4 \times 10^{-5}$ M to about $4 \times 10^{-6}$ M, about $4 \times 10^{-6}$ to about $4 \times 10^{-7}$ M, about $4 \times 10^{-7}$ to about $4 \times 10^{-8}$ M, about $4 \times 10^{-8}$ M to about $4 \times 10^{-9}$ M, about $4 \times 10^{-9}$ M to about $4 \times 10^{-10}$ M, about $4 \times 10^{-10}$ M to about $4 \times 10^{-11}$ M, about $4 \times 10^{-11}$ M to about $4 \times 10^{-12}$ M, about $5 \times 10^{-3}$ M to about $5 \times 10^{-4}$ M, about $5 \times 10^{-4}$ M to about $5 \times 10^{-5}$ M, about $5 \times 10^{-5}$ M to about $5 \times 10^{-6}$ M, about $5 \times 10^{-6}$ to about $5 \times 10^{-7}$ M, about $5 \times 10^{-7}$ to about $5 \times 10^{-8}$ M, about $5 \times 10^{-8}$ M to about $5 \times 10^{-9}$ M, about $5 \times 10^{-9}$ M to about $5 \times 10^{-10}$ M, about $5 \times 10^{-10}$M to about $5 \times 10^{-11}$ M, about $5 \times 10^{-11}$ M to about $5 \times 10^{-12}$ M, about $5 \times 10^{-7}$ M to about $5 \times 10^{-11}$ M, about $5 \times 10^{-7}$ M, about $1 \times 10^{-7}$ M, about $5 \times 10^{-8}$ M, about $1 \times 10^{-8}$ M, about $5 \times 10^{-9}$ M, about $1 \times 10^{-9}$ M, about $5 \times 10^{-10}$ M, about $1 \times 10^{-10}$ M, about $5 \times 10^{-11}$ M or about $1 \times 10^{-11}$ M. In some embodiments, the $K_D$ is determined in a standard flow cytometry assay using HUVEC cells. In one embodiment, the anti-TM4SF1 antibody, or antigen-binding fragment thereof, binds to human TM4SF1 with a $K_D$ of about $5 \times 10^{-10}$ M or less in a standard flow cytometry assay using TM4SF1 expressing HUVEC cells.

In one embodiment, binding of an anti-TM4SF1 antibody, or antigen binding fragment, of the disclosure to human TM4SF1 is not dependent on glycosylation of the ECL2 loop of human TM4SF1, i.e., binding of the antibody is independent of glycosylation of TM4SF1 within the ECL2 loop (SEQ ID NO: 77).

The anti-TM4SF1 antibodies, or antigen-binding fragments thereof, of the disclosure may be any of any isotype (for example, but not limited to IgG, IgM, and IgE). In certain embodiments, antibodies, or antigen-binding fragments thereof, of the disclosure are IgG isotypes. In a specific embodiment, antibodies, or antigen-binding fragments thereof, of the disclosure are of the IgG1, IgG2 or IgG4 isotype. In certain embodiments, the anti-TM4SF1 antibody, or antigen-binding fragment thereof, are human IgG1, human IgG2, or human IgG4 isotype.

IgG2 is naturally the lowest in ADCC and/or CDC activity (An et al., MAbs. 2009 November-December; 1(6): 572-579). Accordingly, in certain embodiments it IgG2 is advantageously used. However, IgG2 has two extra cysteines (leading to 4 inter-hinge disulfide bonds) which make it prone to aggregation via formation of inter-antibody disulfide bonds. In a related embodiment, mutations to the IgG2 cysteines are made to decrease aggregation.

The present disclosure provides antibody fragments that bind to TM4SF1. In certain circumstances there are advantages of using antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from E. coli or yeast cells, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., 1992, Bio/Technology 10:163-67). According to another approach, F(ab')2 fragments can be isolated directly from recombinant host cell culture. Fab and F(ab')2 fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific.

In certain embodiments, the antigen binding fragment is selected from the group consisting of a Fab, a Fab', a F(ab')2, an Fv, and an scFv.

Anti-TM4SF1 antibodies (and fragments) that, for example, have a high affinity for human TM4SF1, can be identified using screening techniques known in the art. For example, monoclonal antibodies may be made using the hybridoma method first described by Kohler et al., 1975, Nature 256:495-97, or may be made by recombinant DNA methods (see, e.g., U.S. Pat. No. 4,816,567).

In the hybridoma method, a mouse or other appropriate host animal, such as a hamster, is immunized using, for example, the ECL2 loop of human TM4SF1 or cells expressing TM4SF1 (whereby the ECL2 loop is expressed on the cell surface), to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice 59-103 (1986)).

The hybridoma cells thus prepared are seeded and grown in a suitable culture medium which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, Va.), and those derived from MOPC-21 and MPC-11 mouse tumors available from the Salk Institute Cell Distribution Center (San Diego, Calif.). Human myeloma and mouse-human heteromyeloma cell lines also have been described for the production of human monoclonal antibodies (Kozbor, 1984, Immunol. 133:3001-05; and Brodeur et al., Monoclonal Antibody Production Techniques and Applications 51-63 (1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al., 1980, Anal. Biochem. 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol. 5:256-62 and Pluckthun, 1992, Immunol. Revs. 130:151-88.

In a further embodiment, monoclonal antibodies or antibody fragments can be isolated from antibody phage libraries generated using the techniques described in, for example, Antibody Phage Display: Methods and Protocols (O'Brien and Aitken eds., 2002). In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self-antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, TM4SF1 (e.g., a soluble form of the ECL2 loop or cells expressing said loop) can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Anti-TM4SF1 antibodies can be obtained by designing a suitable antigen screening procedure to select for the phage clone of interest followed by construction of a full length anti-TM4SF1 antibody clone using VH and/or VL sequences (e.g., the Fv sequences), or various CDR sequences from VH and VL sequences, from the phage clone of interest and suitable constant region (e.g., Fc) sequences described in Kabat et al., supra.

Screening of anti-TM4SF1 antibodies can be performed using binding assays known in the art and described herein for determining whether the antibody has a therapeutic affinity for the ECL2 loop of TM4SF1. The ability of the antibody to inhibit or decrease metastatic cell activity can be measured using standard assays in the art, as well as those described herein. Preclinical assays require use of an animal model of metastasis, commonly of one of three types: (i) injection of metastatic mouse tumor cells such as B16F10 melanoma TCs into mice, commonly via tail vein injection to generate lung metastases, via portal vein or intrasplenic injection to generate liver metastases, or via left ventricular cardiac injection to generate bone and other metastases; (ii) orthotopic transplantation of metastatic tumor cells or intact tumor fragments into mice, which methods often require later surgical resection of the primary tumor to prevent morbidity associated with primary tumor growth; and (iii) genetically engineered mouse models of spontaneous metastasis, of which the most common is the MMTV-Pyt (mouse mammary tumor virus-polyomavirus middle T Antigen) mouse mammary carcinoma model which provides a highly realistic mouse model of human cancer metastasis; greater than 85% of hemizygous MMTV-PyMT females spontaneously develop palpable mammary tumors which metastasize to the lung at age to 8-16 weeks. Quantifying the metastatic burden in the lung, either by live animal imaging or direct counting of metastatic nodules in the lungs of sacrificed animals, as a function of the degree of TM4SF1 immunoblockade and achieving a therapeutic level, e.g., at least a 50% reduction in lung metastasis, would be indicative, for example, of a therapeutic antibody that could be used in the methods of the disclosure. Further, cross-species reactivity assays are known in the art. Examples of assays that can be used are described, for example, in Khanna and Hunter (Carcinogenesis. 2005 March; 26(3):513-23) and Saxena and Christofori (Mol Oncol. 2013 April; 7(2):283-96), incorporated by reference in their entireties herein.

In one embodiment of the disclosure, the anti-TM4SF1 antibody, or antigen-binding fragment thereof, contains a mutation(s) that reduces or ablates the ADCC and/or CDC effector function of the antibody or fragment.

The term "antibody-dependent cell-mediated cytotoxicity (ADCC)" as used herein refers to the killing of an antibody-coated target cell by a cytotoxic effector cell through a nonphagocytic process, characterized by the release of the content of cytotoxic granules or by the expression of cell death-inducing molecules. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, monocytes, macrophages, neutrophils, eosinophils and dendritic cells. ADCC is a rapid effector mechanism whose efficacy is dependent on a number of parameters (density and stability of the antigen on the surface of the target cell; antibody affinity and FcR-binding affinity). PBMC-based ADCC assays and natural kill cell-based ADCC assays can be used to detect ADCC. The readout in these assays is endpoint-driven (target cell lysis).

Complement dependent cytotoxicity" or "CDC" refers to the lysis of a target cell in the presence of complement. Activation of the classical complement pathway is initiated by the binding of the first component of the complement system (C1 q) to antibodies (of the appropriate subclass) which are bound to their cognate antigen. To assess complement activation, a CDC assay (see, e.g., Gazzano-Santoro et al., 1996, J. Immunol. Methods 202:163) may be performed. Polypeptide variants with altered Fc region amino acid sequences (polypeptides with a variant Fc region) and increased or decreased C1q binding capability have been described (see, e.g., U.S. Pat. No. 6,194,551; WO 1999/51642; Idusogie et al., 2000, J. Immunol. 164: 4178-84). Antibodies (or fragments) with little or no CDC activity may be selected for use.

The term "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Examples of antibody effector functions include: C1q binding and complement dependent cytotoxicity (CDC); Fc receptor binding; antibody-dependent cell-mediated cytotoxicity (ADCC); phagocytosis (ADCP); down regulation of cell surface receptors (e.g. B cell receptor); and B cell activation.

The term "reduce" or "ablate" as used herein refers to the ability to cause an overall decrease preferably of 20% or greater, more preferably of 50% or greater, and most preferably of 75%, 85%, 90%, 95%, or greater. Reduce or ablate can refer to the symptoms of the disorder (e.g., cancer) being treated, the presence or size of metastases or the size of the primary tumor.

The term "reduced ADCC/CDC function" as used herein refers to a reduction of a specific effector function, e.g. ADCC and/or CDC, in comparison to a control (for example an antibody with a Fc region not including the mutation(s)), by at least about 5%, at least about 10%, at least about 15%, at least about 20%, at least about 30%, at least about 40%, at least about 50%, at least about 60%, at least about 70%, at least about 80% at least, at least about 90% or more.

Accordingly, in certain embodiments the mutated antibodies of the disclosure have reduced or ablated affinity for an Fc ligand responsible for facilitating effector function compared to an antibody having the same amino acid sequence as the antibody of the disclosure but not comprising the addition, substitution, or deletion of at least one amino acid residue to the Fc region (also referred to herein as an "unmodified antibody").

In one embodiment, the anti-TM4SF1 antibody, or antigen-binding fragment thereof, comprises an Fc region comprising at least two mutations that reduce or ablate ADCC and/or CDC effector function of the antibody, or antigen-binding fragment thereof. In further embodiments, the anti-TM4SF1 antibody, or antigen-binding fragment thereof, comprises an Fc region comprising at least three, at least four, at least five, at least six, at least seven, at least eight, at least nine, at least ten or more mutations that reduce or ablate ADCC and/or CDC effector function of the antibody, or antigen-binding fragment thereof.

In certain embodiments, the anti-TM4SF1 antibody, or antigen-binding fragment thereof, is an IgG1 isotype and comprises an Fc region comprising one or more mutations selected from the group consisting of E233P, L234V, L234A, L235A, G236Delta (deletion), G237A, V263L, N297A, N297D, N297G, N297Q, K322A, A327G, P329A, P329G, P329R, A330S, P331A and P331S.

In one embodiment, the anti-TM4SF1 antibody, or antigen-binding fragment thereof, is an IgG1 isotype and comprises an Fc region comprising an L234A/L235A mutation, with or without a G237A mutation. In one embodiment, the anti-TM4SF1 antibody, or antigen-binding fragment thereof, is an IgG1 isotype and comprises an Fc region comprising L234A, L235A, and G237A mutations.

In one embodiment, the anti-TM4SF1 antibody, or antigen-binding fragment thereof, is an IgG1 isotype and comprises an Fc region comprising an A327G/A330S/P331S mutation.

In one embodiment, the anti-TM4SF1 antibody, or antigen-binding fragment thereof, is an IgG1 isotype and comprises an Fc region comprising an E233P/L234V/L235A/delta G236 (deletion) mutation, which provides reduced binding to FcγRI, FcγRIIA, FcγRIIIA and reduced ADCC and CDC effector function, as described, for example, in An Z et al. Mabs 2009 November-Ec; 1(6):572-9, incorporated by reference in its entirety herein.

In one embodiment, the anti-TM4SF1 antibody, or antigen-binding fragment thereof, is an IgG1 isotype and comprises an Fc region comprising an N297x mutation, where x=A, D, G, Q.

In one embodiment, the anti-TM4SF1 antibody, or antigen-binding fragment thereof, is an IgG1 isotype and comprises an Fc region comprising an A327G/A330S/P331S mutation.

In one embodiment, the anti-TM4SF1 antibody, or antigen-binding fragment thereof, is an IgG1 isotype and comprises an Fc region comprising a mutation in one or more of K322A, P329A, and P331A, which provides reduced binding to C1q, as described, for example, in Canfield &Morrison. J Exp Med (1991) 173(6):1483-91.10.1084, incorporated by reference in its entirety herein.

In one embodiment, the anti-TM4SF1 antibody, or antigen-binding fragment thereof, is an IgG1 isotype and comprises an Fc region comprising a V263L mutation, which provides enhanced binding to FcγRIIB and enhanced ADCC, as described in, for example, Hezareh et al. J Virol. 2001 December; 75(24):12161-8, incorporated by reference in its entirety herein.

In other embodiments, the anti-TM4SF1 antibody, or antigen-binding fragment thereof, is an IgG1 isotype and comprises an Fc region comprising a L234A/L235A, G237A or L235E mutation.

In other embodiments, the anti-TM4SF1 antibody, or antigen-binding fragment thereof, is an IgG1 isotype and comprises an Fc region comprising a L234F, L235E or P331S mutation.

In certain embodiments, the anti-TM4SF1 antibody, or antigen-binding fragment thereof, is an IgG2 isotype and comprises an Fc region comprising a one or more mutations selected from the group consisting of V234A, G237A, P238S, H268A or H268Q, V309L, A330S and P331S.

In one embodiment, the anti-TM4SF1 antibody, or antigen-binding fragment thereof, is an IgG2 isotype and comprises an Fc region comprising an A330S/P331S mutation.

In one embodiment, the anti-TM4SF1 antibody, or antigen-binding fragment thereof, is an IgG2 isotype and comprises an Fc region comprising an A330S/P331S, V234A/

G237A/P238S/H268A/V309L/A330S/P331S or H268Q/V309L/A330S/P331S mutation.

In other embodiments, the anti-TM4SF1 antibody, or antigen-binding fragment thereof, is an IgG4 isotype and comprises an Fc region comprising a one or more mutations selected from the group consisting of S228P, E233P, F234A, F234V, L235E, L235A, G236Delta (deletion), N297A, N297D, N297G, N297Q, P329G, P329R.

In certain embodiments, the anti-TM4SF1 antibody, or antigen-binding fragment thereof, is an IgG4 isotype and comprises an Fc region comprising an S228P mutation, which provides reduced Fab-arm exchange and reduced aggregation, as described for example in Chappel et al. Proc Natl Acad Sci USA (1991) 88(20):9036-40, incorporated by reference in its entirety herein.

In one embodiment, the anti-TM4SF1 antibody, or antigen-binding fragment thereof, is an IgG4 isotype and comprises an Fc region comprising an S228P/L235E mutation.

In one embodiment, the anti-TM4SF1 antibody, or antigen-binding fragment thereof, is an IgG4 isotype and comprises an Fc region comprising an S228P/E233P/F234V/L235A/delta G236 (deletion) mutation.

In one embodiment, the anti-TM4SF1 antibody, or antigen-binding fragment thereof, is an IgG4 isotype and comprises an Fc region comprising an N297x mutation, where x=A, D, G, Q.

In one embodiment, the anti-TM4SF1 antibody, or antigen-binding fragment thereof, is an IgG4 isotype and comprises an Fc region comprising an S228P/F234A/L235A mutation.

In one embodiment, the anti-TM4SF1 antibody, or antigen-binding fragment thereof, is an IgG4 isotype and comprises an Fc region comprising a L235E mutation, which provides reduced binding to FcγRI, FcγRIIA, FcγRIIIA and reduced ADCC and CDC effector activity, as described in, for example, Saxena et al. Front Immunol. 2016 Dec. 12; 7:580, incorporated by reference in its entirety herein.

In other embodiments, the anti-TM4SF1 antibody, or antigen-binding fragment thereof, is an IgG4 isotype and comprises an Fc region comprising a S228P/F234A/L235A or E233P/L235A/G236Delta mutation.

In one embodiment, the anti-TM4SF1 antibody, or antigen-binding fragment thereof, is an IgG4 isotype and comprises an Fc region comprising at least a S228P mutation. Angal et al. (Mol Immunol. 1993 January; 30(1):105-8) describe an analysis of the hinge sequences of human IgG4 heavy chains to determine that the presence of serine at residue 241 (according to EU numbering system, and now corresponding to residue 228 in Kabat numbering) as the cause of heterogeneity of the inter-heavy chain disulphide bridges in the hinge region in a proportion of secreted human IgG4. Silva et al. (J Biol Chem. 2015 Feb. 27; 290(9):5462-9) describe the S228P mutation in human IgG4 that prevents in vivo and in vitro IgG4 Fab-arm exchange.

In other embodiments, the anti-TM4SF1 antibody, or antigen-binding fragment thereof, is an IgG4 isotype and comprises an Fc region comprising a L235E or S228P mutation.

In other embodiments, the anti-TM4SF1 antibody, or antigen-binding fragment thereof, is an IgG4 or IgG1 isotype and comprises an Fc region comprising a N297A, N297D or N297G mutation.

In other embodiments, the anti-TM4SF1 antibody, or antigen-binding fragment thereof, is an IgG4 or IgG1 isotype and comprises an Fc region comprising a P329G, P329R mutation.

In one exemplary embodiment, the mutated Fc region of any IgG isotype comprises one or more mutations at positions 234, 235, 236, 237, 297, 318, 320, 322 (as described in WO1988007089, incorporated by reference in its entirety herein). Other possible mutations in the Fc region, including substitutions, deletions and additions are also described in, for example, US20140170140, WO2009100309, US20090136494 and U.S. Pat. No. 8,969,526, incorporated by reference in their entireties herein.

In vitro and/or in vivo cytotoxicity assays can be conducted to confirm the reduction or ablation of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, RII and RIII. Non-limiting examples of in vitro assays to assess ADCC activity of a molecule of interest is described in U.S. Pat. No. 5,500,362 (see, e.g. Hellstrom, I., et al., Proc. Nat'l Acad. Sci. USA 83 (1986) 7059-7063) and Hellstrom, I., et al., Proc. Nat'l Acad. Sci. USA 82 (1985) 1499-1502; U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, et al., Proc. Nat'l Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, et al., J. Immunol. Methods 202 (1996) 163; Cragg, M. S., et al., Blood 101 (2003) 1045-1052; and Cragg, M. S., and Glennie, M. J., Blood 103 (2004) 2738-2743). FcRn binding and in vivo clearance/half-life determinations can also be performed using methods known in the art (see, e.g., Petkova, S. B., et al., Int'l. Immunol. 18(12) (2006) 1759-1769).

In one embodiment, antibodies, or antigen-binding fragments thereof, of the disclosure exhibit reduced or ablated ADCC effector function as compared to unmodified antibodies. In another embodiment, antibodies, or antigen-binding fragments thereof, of the disclosure exhibit reduced ADCC effector function that is at least 2 fold, or at least 3 fold, or at least 5 fold or at least 10 fold or at least 50 fold or at least 100 fold less than that of an unmodified antibody. In still another embodiment, antibodies of the disclosure exhibit ADCC effector function that is reduced by at least 10%, or at least 20%, or by at least 30%, or by at least 40%, or by at least 50%, or by at least 60%, or by at least 70%, or by at least 80%, or by at least 90%, or by at least 100%, relative to an unmodified antibody. In a further aspect of the disclosure the reduction or down-modulation of ADCC effector function induced by the antibodies, or antigen-binding fragments thereof, of the present disclosure, is a reduction to 0, 2.5, 5, 10, 20, 50 or 75% of the value observed for induction of ADCC by unmodified antibodies. In certain embodiments, the reduction and/or ablation of ADCC activity may be attributed to the reduced affinity of the antibodies, or antigen-binding fragments thereof, of the disclosure for Fc ligands and/or receptors.

III. Polynucleotides

Also provided, in some embodiments, are polynucleotides encoding a TM4SF1 binding protein as described herein, such as an anti-TM4SF1 antibody or an antigen binding fragment thereof. In some embodiments, the polynucleotide molecules are provided as a DNA construct. In other embodiments, the polynucleotide molecules are provided as a messenger RNA transcript.

In some examples, an anti-TM4SF1 antibody of the present disclosure comprises a heavy chain variable domain encoded by a nucleic acid sequence as set forth in any one of SEQ ID NOs: 4, 16, 28, 40, 52, 64, or 76. In some examples, an anti-TM4SF1 antibody of the present disclosure comprises a light chain variable domain encoded by a nucleic acid sequence as set forth in any one of SEQ ID NOs: 10, 22, 34, 46, 58, 70, or 82.

In some embodiments are provided nucleic acid sequences that are codon optimized for expression in a host cell, e.g., a bacterium, such as E. coli, or a eukaryotic cell, such as a CHO cell. In some examples, the nucleic acid sequences are codon optimized for expression in CHO cells. In some examples, an anti-TM4SF1 antibody of the present disclosure comprises a heavy chain variable domain encoded by a codon optimized nucleic acid sequence as set forth in any one of SEQ ID NOs: 5, 17, 29, 41, 53, 65, or 77. In some examples, an anti-TM4SF1 antibody of the present disclosure comprises a light chain variable domain encoded by a codon optimized nucleic acid sequence as set forth in any one of SEQ ID NOs: 11, 23, 35, 47, 59, 71, or 83. In certain instances, the nucleic acid sequence of any one of SEQ ID NOs: 5, 17, 29, 41, 53, 65, or 77 is a nucleic acid sequence codon optimized for expression in CHO cell. In certain instances, the nucleic acid sequence of any one of SEQ ID NOs: 11, 23, 35, 47, 59, 71, or 83 is a nucleic acid sequence codon optimized for expression in CHO cell.

The polynucleotide molecules are constructed by known methods such as by incorporating the genes encoding the binding proteins into a genetic construct linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, a polynucleotide as described herein is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described TM4SF1 binding protein. Examples of expression vectors for expression in E. coli are pSKK (Le Gall et al., J Immunol Methods. (2004) 285(1): 111-27) or pcDNAS (Invitrogen) for expression in mammalian cells.

Thus, the TM4SF1 binding proteins as described herein, in some embodiments, are produced by introducing a vector encoding the protein as described above into a host cell and culturing said host cell under conditions whereby the protein domains are expressed, may be isolated and, optionally, further purified.

IV. Methods of Treatment

The disclosure further provides a method for inhibiting cell-cell interactions that are endothelial cell (EC) specific, for example, but not limited to EC-EC, EC-mesenchymal stem cell, EC-fibroblast, EC-smooth muscle cell, EC-tumor cell, EC-leukocyte, EC-adipose cell and EC-neuronal cell interactions. In certain embodiments, the anti-TM4SF1 antibodies and fragments of the present disclosure, can be used to treat any human disease or disorder with a pathology that is characterized by abnormal EC-cell interactions. In certain embodiments, the EC-cell interaction is an EC-leukocyte interaction, where inhibition of the EC-leukocyte interaction is used to prevent inflammation.

In other embodiments, the disclosure features a method of treating or preventing a disease or disorder in a subject, wherein the disease or disorder is characterized by abnormal endothelial cell (EC)-cell interactions, said method comprising administering the antibody, or antigen-binding fragment thereof, as described herein. In certain embodiments, the EC-cell interactions include one or more of EC-mesenchymal stem cell, EC-fibroblast, EC-smooth muscle cell, EC-tumor cell, EC-leukocyte, EC-adipose cell and EC-neuronal cell interactions. In exemplary embodiments, the disease is an inflammatory disease or disorder, and the antibodies and fragments of the disclosure are used to inhibit EC-leukocyte interactions. In another exemplary embodiment, the disease or disorder is selected from an inflammatory disease or cancer. The adhesion of leukocytes to vascular endothelium is a hallmark of the inflammatory process. Accordingly, in one embodiment, an anti-TM4SF1 antibody, or an antigen binding fragment thereof, of the present disclosure is used to treat an inflammatory disease in which inhibiting leukocyte attachment to endothelial cells, or leukocyte transmigration across the endothelium is helpful for treatment (see, e.g. Rychly et al., Curr Pharm Des. 2006; 12(29):3799-806, incorporated by reference in its entirety herein). Examples include, but are not limited to, sepsis, inflammatory bowel disease, psoriasis or multiple sclerosis.

Each year approximately half a million patients die from cancer in the United States alone. Tumor metastasis is responsible for ~90% of these deaths. No therapy that blocks metastasis is known. The present disclosure provides antibodies, and antigen-binding fragments thereof, that can treat cancer and inhibit metastatic cells based on immunoblockade of tumor cell (TC)—endothelial cell (EC) interactions mediated by a novel target, TM4SF1.

As described above, TM4SF1 is a small, tetraspanin-like, cell surface glycoprotein originally discovered as a TC antigen with roles in TC invasion and metastasis. TM4SF1 is selectively expressed by TCs and ECs. TM4SF1 is expressed at low levels on the vascular ECs supplying normal tissues in both mice and humans. It has been shown that TM4SF1 is expressed at ~10-20 fold higher levels on the vascular ECs lining the blood vessels supplying many human cancers, and at equivalent high levels on cultured ECs. FIG. 1 provides a schematic that illustrates the putative role of TM4SF1 in TC and EC interactions for extravasation. TM4SF1-enriched microdomains (TMED) recruit cell surface proteins like integrins to assist the formation of nanopodia, thin membrane channels that extend from the cell surface and mediate cell-cell interactions. Thus, in certain instances, anti-TM4SF1 antibodies and fragments described herein interfere with nanopodia-mediated interactions and inhibit TC interactions with EC that are necessary for TC extravasation.

Any one of the TM4SF1 binding proteins or pharmaceutical compositions described herein may be formulated for treating a subject (e.g., a human) having a disorder associated with pathological angiogenesis (e.g., cancer, such as breast cancer, ovarian cancer, renal cancer, colorectal cancer, liver cancer, gastric cancer, and lung cancer; obesity; macular degeneration; diabetic retinopathy; psoriasis; rheumatoid arthritis; cellular immunity; and rosacea.

TM4SF1 is highly expressed on the surface of most epithelial TCs, and, is also highly expressed on the EC lining tumor blood vessels and on cultured EC. It is expressed at ~10-20 fold lower levels on the surface of normal vascular ECs. In mouse models, tumor metastasis to lungs is related to TM4SF1 expression on both ECs and TCs. Metastasis requires initial attachment of TC to vascular EC and their subsequent migration across ECs to enter the lung or other metastatic sites. The examples below show that, in some instances, the anti-TM4SF1 antibodies of the present disclosure interfere with TC-EC interactions in culture and can also inhibit tumor metastasis in vivo.

Thus, the antibodies and fragments of the present disclosure can be used to block one or both of the earliest steps in metastasis (see FIG. 1), namely, TC attachment to vascular ECs and/or transmigration of TCs across ECs, and thereby prevent or substantially reduce the number of metastases in at risk cancer patients.

The present disclosure further provides a method for preventing metastasis. Human tumors typically shed TCs into the blood and lymphatics at early stages of growth; hence, early treatment of primary tumors provides no guarantee that metastasis has not already taken place. Thus, immunoblockade of TM4SF1 can be used to treat or prevent hematogenous metastases or to treat or prevent lymphatic metastases.

The methods of this disclosure are, in some embodiments, directed to inhibiting metastatic cells in a subject. In one embodiment, the subject has a cancer, e.g., a cancer that is associated with metastasis or a cancer that has already metastasized. In other embodiments, the subject was already treated for cancer and is in remission or partial remission, wherein the benefits of administering the anti-TM4SF1 antibodies or fragments described herein are that they work to prevent metastasis and maintain remission or partial remission.

In certain embodiments, the disclosure provides a method of treating a person having a greater risk of developing metastasis, wherein administration of the anti-TM4SF1 antibodies and fragments described herein can be used to inhibit or delay onset of metastasis.

Included in the disclosure is a method of blocking tumor metastasis, particularly metastasis to the lung, by administering an anti-TM4SF1 antibody to a subject in need thereof. In some examples, the anti-TM4SF1 antibody is a human anti-TM4SF1 antibody, also referred to herein as anti-hTM4SF1. In certain embodiments, the methods include administration of an effective amount of an anti-hTM4SF1 antibody to a subject in need thereof, wherein the effective amount of the antibody prevents tumor cell (TC) attachment to and migration across vascular endothelial cells (ECs).

In certain embodiments, an anti-TM4SF1 antibody is administered to a subject having cancer or at risk of having metastasis such that the dose amount and frequency maintains long term TM4SF1 immunoblockade. The dosing regimen will maximally inhibit TM4SF1-mediated metastasis by administering an anti-TM4SF1 antibody to a subject in an amount sufficient to saturate TM4SF1 expressed on normal vascular ECs of the subject.

In certain embodiments, the effective amount of an anti-TM4SF1 antibody, or an antigen binding fragment thereof, that is administered is an amount sufficient to, at one week, achieve circulating antibody concentrations >1 µg/ml.

In certain embodiments, the effective amount of an anti-TM4SF1 antibody, or an antigen binding fragment thereof that is administered is an amount sufficient to maintain serum concentrations of the antibody at or above 1 µg/ml continuously for about 1 month.

In one embodiment, the disclosure provides a method of treating or preventing metastasis in a human subject comprising administering to the subject an effective amount of an anti-TM4SF1 antibody, or an antigen binding fragment thereof, wherein the effective amount of the antibody, or antigen binding fragment thereof, comprises 1 to 80 mg/kg of the amount of the antibody, or antigen binding fragment thereof.

The mode of administration for therapeutic use of the antibodies of the disclosure may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

In some embodiments, the antibodies of the disclosure may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hours. The dose given to a subject in some embodiments is about 0.005 mg to about 100 mg/kg, e.g., about 0.05 mg to about 30 mg/kg or about 5 mg to about 25 mg/kg, or about 4 mg/kg, about 8 mg/kg, about 16 mg/kg or about 24 mg/kg, or for example about 0.1, 0.2, 0.3, 0.4, 0.5, 0.6, 0.7, 0.8, 0.9, 1, 2, 3, 4, 5, 6, 7, 8, 9 or 10 mg/kg. In certain embodiments, the dose given to a subject is, for example about 15, 16, 17, 18, 19, 20, 21, 22, 23, 24, 25, 30, 40, 50, 60, 70, 80, 90 or 100 mg/kg. In some instances, the dose of the antibodies of the disclosure given to a subject may be about 0.1 mg/kg to 10 mg/kg via intravenous administration. In some instances, the dose of the antibodies of the disclosure given to a subject is about 0.1 mg/kg to 10 mg/kg via subcutaneous administration. In some instances, the dose of the antibodies of the disclosure given to a subject is about 0.1 mg/kg via intravenous administration. In some instances, the dose of the antibodies of the disclosure given to a subject is about 0.1 mg/kg via subcutaneous administration. In some embodiments, the dose of the antibodies of the disclosure given to a subject is about 0.3 mg/kg via intravenous administration. In some examples, the dose of the antibodies of the disclosure given to a subject is about 0.3 mg/kg via subcutaneous administration. In some examples, the dose of the antibodies of the disclosure given to a subject is about 1.0 mg/kg via intravenous administration. In some examples, the dose of the antibodies of the disclosure given to a subject is about 1.0 mg/kg via subcutaneous administration. In some examples, the dose of the antibodies of the disclosure given to a subject is about 3.0 mg/kg via intravenous administration. In some examples, the dose of the antibodies of the disclosure given to a subject is about 3.0 mg/kg via subcutaneous administration. In some examples, the dose of the antibodies of the disclosure given to a subject may be about 10.0 mg/kg via intravenous administration. In some examples, the dose of the antibodies of the disclosure given to a subject is about 10.0 mg/kg via subcutaneous administration.

In certain embodiments, a fixed unit dose of the antibodies of the disclosure is given, for example, 50, 100, 200, 500 or 1000 mg, or the dose may be based on the patient's surface area, e.g., 500, 400, 300, 250, 200, or 100 mg/m$^2$. In some instances, between 1 and 8 doses, (e.g., 1, 2, 3, 4, 5, 6, 7 or 8) is administered to treat the patient, but 9, 10, 11, 12, 13, 14, 15, 16, 17, 18, 19, 20 or more doses are given.

The administration of the antibodies of the disclosure described herein, in some embodiments, is repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration is at the same dose or at a different dose. In some examples, the antibodies of the disclosure described herein is administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion. Alternatively, in some embodiments, the antibodies of the disclosure described herein are administered at between 0.1 mg/kg to about 10 mg/kg at weekly interval for 17 weeks. For example, in some cases the antibodies of the disclosure are provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof. In some embodiments, the antibodies of the disclosure described herein is administered prophylactically in order to reduce the risk of developing an inflammatory disease such as RA, psoriatic arthritis or psoriasis, delay the onset of the occurrence of an event in progression of the inflammatory disease such as RA, psoriatic arthritis or psoriasis. In some examples, the antibodies of the disclosure is lyophilized for storage and reconstituted in a suitable carrier prior to use. In some cases, the antibodies of the disclosure are supplied as a sterile, frozen liquid in a glass vial with stopper and aluminum seal with flip-off cap. In some examples, each vial contains 3.3 mL of a 50 mg/mL solution of the antibody (including a 10% overfill) in a formulation of 10 mM histidine, 8.5% (w/v) sucrose, and 0.04% (w/v) Polysorbate 80 at pH 5.8. In some examples, the vials contain no preservatives and are for single use. Vials may be stored frozen and protected from light. To prepare the antibody for IV administration, the antibody formulations, in some examples, are filtered with a 0.22 micron filter before being diluted in sterile diluent. In some examples, diluted antibodies at volumes up to approximately 100 mL is administered by IV infusion over a period of at least 30 minutes using an in-line 0.22 micron filter. Alternatively, in some embodiments, the antibody is administered as 1 or 2 subcutaneous injections of 50 mg/mL antibody in about 3.3 mL. The subcutaneous injection site may be, for example, within the abdominal area.

V. Pharmaceutical Compositions

Any one of the TM4SF1 binding proteins of the disclosure (e.g., anti-TM4SF1 antibodies, or antigen-binding fragments thereof) or polynucleotides encoding the TM4SF1 binding proteins of the disclosure, can be included in compositions (e.g., pharmaceutical compositions). The pharmaceutical compositions of the disclosure may further include a pharmaceutically acceptable carrier, excipient, or diluent.

The term "pharmaceutical composition" as used herein refers to a composition containing a TM4SF1 binding protein described herein formulated with a pharmaceutically acceptable carrier, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The term "pharmaceutically acceptable carrier" as used herein refers to a carrier which is physiologically acceptable to a treated mammal (e.g., a human) while retaining the therapeutic properties of the protein with which it is administered. One exemplary pharmaceutically acceptable carrier is physiological saline. Other physiologically acceptable carriers and their formulations are known to one skilled in the art and described, for example, in Remington's Pharmaceutical Sciences (18th edition, A. Gennaro, 1990, Mack Publishing Company, Easton, Pa.), incorporated herein by reference.

Pharmaceutical compositions containing a TM4SF1 binding protein as described above, are, in some embodiments, prepared as solutions, dispersions in glycerol, liquid polyethylene glycols, and any combinations thereof in oils, in solid dosage forms, as inhalable dosage forms, as intranasal dosage forms, as liposomal formulations, dosage forms comprising nanoparticles, dosage forms comprising microparticles, polymeric dosage forms, or any combinations thereof.

A pharmaceutically acceptable excipient is, in some examples, an excipient described in the Handbook of Pharmaceutical Excipients, American Pharmaceutical Association (1986). Non-limiting examples of suitable excipients include a buffering agent, a preservative, a stabilizer, a binder, a compaction agent, a lubricant, a chelator, a dispersion enhancer, a disintegration agent, a flavoring agent, a sweetener, a coloring agent.

In some embodiments an excipient is a buffering agent. Non-limiting examples of suitable buffering agents include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof is used, in some embodiments, in a pharmaceutical composition of the present disclosure.

In some embodiments an excipient comprises a preservative. Non-limiting examples of suitable preservatives include antioxidants, such as alpha-tocopherol and ascorbate, and antimicrobials, such as parabens, chlorobutanol, and phenol. In some examples, antioxidants further include but are not limited to EDTA, citric acid, ascorbic acid, butylated hydroxytoluene (BHT), butylated hydroxy anisole (BHA), sodium sulfite, p-amino benzoic acid, glutathione, propyl gallate, cysteine, methionine, ethanol and N-acetyl cysteine. In some instances preservatives include validamycin A, TL-3, sodium ortho vanadate, sodium fluoride, N-a-tosyl-Phe-chloromethylketone, N-a-tosyl-Lys-chloromethylketone, aprotinin, phenylmethylsulfonyl fluoride, diisopropylfluorophosphate, kinase inhibitor, phosphatase inhibitor, caspase inhibitor, granzyme inhibitor, cell adhesion inhibitor, cell division inhibitor, cell cycle inhibitor, lipid signaling inhibitor, protease inhibitor, reducing agent, alkylating agent, antimicrobial agent, oxidase inhibitor, or other inhibitor.

In some embodiments a pharmaceutical composition as described herein comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof. The binders used in a pharmaceutical formulation are, in some examples, selected from starches such as potato starch, corn starch, wheat starch; sugars such as sucrose, glucose, dextrose, lactose, maltodextrin; natural and synthetic gums; gelatine; cellulose derivatives such as microcrystalline cellulose, hydroxypropyl cellulose, hydroxyethyl cellulose, hydroxypropyl methyl cellulose, carboxymethyl cellulose, methyl cellulose, ethyl cellulose; polyvinylpyrrolidone (povidone); polyethylene glycol (PEG); waxes; calcium carbonate; calcium phosphate; alcohols such as sorbitol, xylitol, mannitol and water or any combinations thereof.

In some embodiments a pharmaceutical composition as described herein comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricants that are used in a pharmaceutical formulation, in some embodiments, are be selected from metallic stearates (such as magnesium stearate, calcium stearate, aluminium stearate), fatty acid esters (such as sodium stearyl fumarate), fatty acids (such as stearic acid), fatty alcohols, glyceryl behenate, mineral oil, paraffins, hydrogenated vegetable oils, leucine, polyethylene glycols (PEG), metallic lauryl sulphates (such as sodium lauryl sulphate, magnesium lauryl sulphate), sodium chloride, sodium benzoate, sodium acetate and talc or a combination thereof.

In some embodiments a pharmaceutical formulation comprises a dispersion enhancer as an excipient. Non-limiting examples of suitable dispersants include, in some examples, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments a pharmaceutical composition as described herein comprises a disintegrant as an excipient. In some embodiments a disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments a disintegrant is an effervescent disintegrant. Non-limiting examples of suitable effervescent disintegrants include sodium bicarbonate in combination with citric acid, and sodium bicarbonate in combination with tartaric acid.

In some embodiments an excipient comprises a flavoring agent. Flavoring agents incorporated into an outer layer are, in some examples, chosen from synthetic flavor oils and flavoring aromatics; natural oils; extracts from plants, leaves, flowers, and fruits; and combinations thereof. In some embodiments a flavoring agent can be selected from the group consisting of cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments an excipient comprises a sweetener. Non-limiting examples of suitable sweeteners include glucose (corn syrup), dextrose, invert sugar, fructose, and mixtures thereof (when not used as a carrier); saccharin and its various salts such as a sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, sylitol, and the like.

In some instances, a pharmaceutical composition as described herein comprises a coloring agent. Non-limiting examples of suitable color agents include food, drug and cosmetic colors (FD&C), drug and cosmetic colors (D&C), and external drug and cosmetic colors (Ext. D&C). A coloring agents can be used as dyes or their corresponding lakes.

In some instances, a pharmaceutical composition as described herein comprises a chelator. In some cases, a chelator is a fungicidal chelator. Examples include, but are not limited to: ethylenediamine-N,N,N',N'-tetraacetic acid (EDTA); a disodium, trisodium, tetrasodium, dipotassium, tripotassium, dilithium and diammonium salt of EDTA; a barium, calcium, cobalt, copper, dysprosium, europium, iron, indium, lanthanum, magnesium, manganese, nickel, samarium, strontium, or zinc chelate of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid;

ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis(methylenephosponic acid); 0,0'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11] pentatriacontane hexahydrobromide; or triethylenetetramine-N,N,N',N'',N''',N'''-hexaacetic acid.

Also contemplated are combination products that include an anti-TM4SF1 antibody as disclosed herein and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that a peptide can be combined with topical antifungal agents such as ciclopirox olamine, haloprogin, tolnaftate, undecylenate, topical nysatin, amorolfine, butenafine, naftifine, terbinafine, and other topical agents. In some instances, a pharmaceutical composition comprises an additional agent. In some cases, an additional agent is present in a therapeutically effective amount in a pharmaceutical composition.

Under ordinary conditions of storage and use, the pharmaceutical compositions as described herein comprise a preservative to prevent the growth of microorganisms. In certain examples, the pharmaceutical compositions as described herein do not comprise a preservative. The pharmaceutical forms suitable for injectable use include sterile aqueous solutions or dispersions and sterile powders for the extemporaneous preparation of sterile injectable solutions or dispersions. The pharmaceutical compositions comprise a carrier which is a solvent or a dispersion medium containing, for example, water, ethanol, polyol (e.g., glycerol, propylene glycol, and liquid polyethylene glycol, and the like), and/or vegetable oils, or any combinations thereof. Proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, isotonic agents are included, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the liquid dosage form is suitably buffered if necessary and the liquid diluent rendered isotonic with sufficient saline or glucose. The liquid dosage forms are especially suitable for intravenous, intramuscular, subcutaneous, intratumoral, and intraperitoneal administration. In this connection, sterile aqueous media that can be employed will be known to those of skill in the art in light of the present disclosure. For example, one dosage is dissolved, in certain cases, in 1 mL to 20 mL of isotonic NaCl solution and either added to 100 mL to 1000 mL of a fluid, e.g., sodium-bicarbonate buffered saline, or injected at the proposed site of infusion.

In certain embodiments, sterile injectable solutions is prepared by incorporating a immunotherapy agent, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. The compositions disclosed herein are, in some instances, formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups are, in some cases, derived from inorganic bases such as, for example, sodium, potassium, ammonium, calcium, or ferric hydroxides, and such organic bases as isopropylamine, trimethylamine, histidine, procaine and the like. Upon formulation, the pharmaceutical compositions are administered, in some embodiments, in a manner compatible with the dosage formulation and in such amount as is therapeutically effective.

In certain embodiments, a pharmaceutical composition of this disclosure comprises an effective amount of an anti-TM4SF1 antibody, as disclosed herein, combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the immunotherapeutic agents or any other suitable vehicle, delivery or dispensing means or material. Such carriers are formulated, for example, by conventional methods and administered to the subject at an effective amount.

VI. Combination Therapies

In certain embodiments, the methods of this disclosure comprise administering an anti-TM4SF1 antibody as disclosed herein, followed by, preceded by or in combination with one or more further therapy. Examples of the further therapy can include, but are not limited to, chemotherapy, radiation, an anti-cancer agent, or any combinations thereof. The further therapy can be administered concurrently or sequentially with respect to administration of the immunotherapy. In certain embodiments, the methods of this disclosure comprise administering an immunotherapy as disclosed herein, followed by, preceded by, or in combination with one or more anti-cancer agents or cancer therapies. Anti-cancer agents include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies include chemotherapy, biological therapy, radiotherapy, immunotherapy, hormone therapy, anti-vascular therapy, cryotherapy, toxin therapy and/or surgery or combinations thereof. In certain embodiments, the methods of this disclosure include administering an immunotherapy, as disclosed herein, followed by, preceded by or in combination with one or more further immunomodulatory agents. An immunomodulatory agent includes, in some examples, any compound, molecule or substance capable of suppressing antiviral immunity associated with a tumor or cancer. Non-limiting examples of the further immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFN3 and IFNγ, and chemokines, such as MIP-1, MCP-1 and IL-8.

In certain examples, where the further therapy is radiation exemplary doses are 5,000 Rads (50 Gy) to 100,000 Rads (1000 Gy), or 50,000 Rads (500 Gy), or other appropriate doses within the recited ranges. Alternatively, the radiation dose are about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®, chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1 S)-2-[(2R)-2-methyl-2-oxiranyl]-2-oxo-1-(phenylmethyl)ethyl]-L-serinamide (ONX-0912).

"In combination with," as used herein, means that the anti-TM4SF1 antibody and the further therapy are administered to a subject as part of a treatment regimen or plan. In certain embodiments, being used in combination does not require that the anti-TM4SF1 antibody and the further therapy are physically combined prior to administration or that they be administered over the same time frame. For example, and not by way of limitation, the anti-TM4SF1 antibody and the one or more agents are administered concurrently to the subject being treated, or are administered at the same time or sequentially in any order or at different points in time.

VII. Kits

The disclosure provides kits that include a composition (e.g., a pharmaceutical composition) of the disclosure (e.g., a composition including an anti-TM4SF1 antibody of the disclosure). The kits include instructions to allow a clinician (e.g., a physician or nurse) to administer the composition contained therein to a subject to treat a disorder associated with pathological angiogenesis (e.g., cancer).

In certain embodiments, the kits include a package of a single-dose pharmaceutical composition(s) containing an effective amount of an antibody of the disclosure. Optionally, instruments or devices necessary for administering the pharmaceutical composition(s) may be included in the kits. For instance, a kit of this disclosure may provide one or more pre-filled syringes containing an effective amount of a vaccine, vector, stabilized trimer, or optimized viral polypeptide of the disclosure. Furthermore, the kits may also include additional components such as instructions regarding administration schedules for a subject having a disorder associated with pathological angiogenesis (e.g., cancer) to use the pharmaceutical composition(s) containing a TM4SF1 binding protein or polynucleotide of the disclosure.

It will be apparent to those skilled in the art that various modifications and variations can be made in the compositions, methods, and kits of the present disclosure without departing from the spirit or scope of the disclosure. Thus, it is intended that the present disclosure cover the modifications and variations of this disclosure provided they come within the scope of the appended claims and their equivalents.

EXAMPLES

The following examples are provided to illustrate, but not to limit the presently claimed disclosure.

Example 1. Tumor Cell (TC)-Endothelial Cell (EC) Interactions are Mediated by TM4SF1

Figure 2:
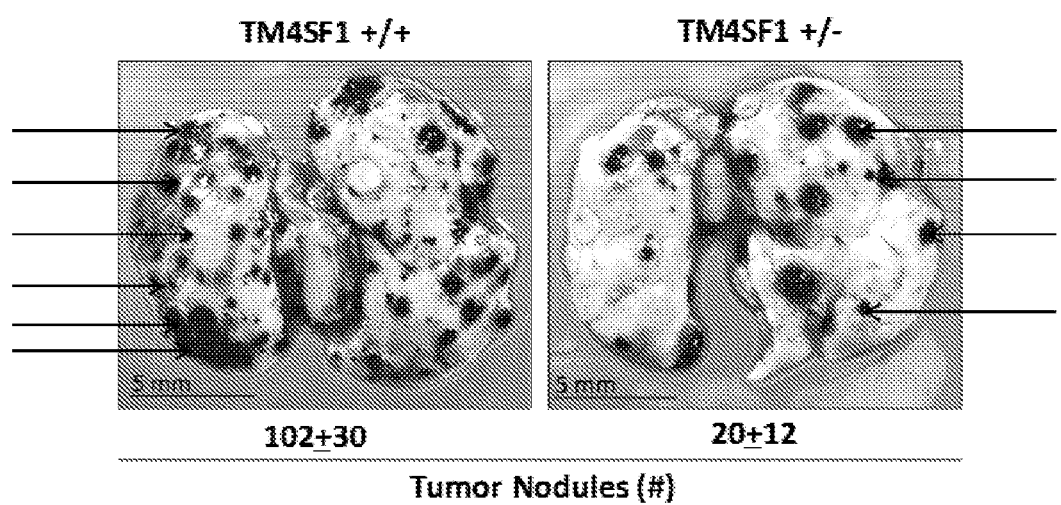
FIG. 2 shows the frequency of TC metastasis to lung in TM4SF1-heterozygous (+/−) mice expressing ~½ the normal level of wild type (+/+) TM4SF1. Number of metastases is shown as tumor nodules (#). Exemplary metastases are indicated with an arrow.

The aim of this study was to determine the expression of TM4SF1 in TC correlation between expression of TM4SF1 and TC metastasis, and effect of an exemplary anti-TM4SF1 antibody, according to the present disclosure, on EC-TC interaction. Levels of TM4SF1 were correlated in vivo with metastasis using TM4SF1-heterozygous (+/−) mice in comparison to wild type mice (TM4SF1+/+). The frequency of TC metastasis to the lung varied with EC TM4SF1 expression. As shown in FIG. 2, lung metastases following tail vein injection of B16F10 TC were nearly 5-fold less in TM4SF1-heterozygous (+/−) mice expressing ~½ the normal level of wild type (+/+) TM4SF1.

Figure 3:
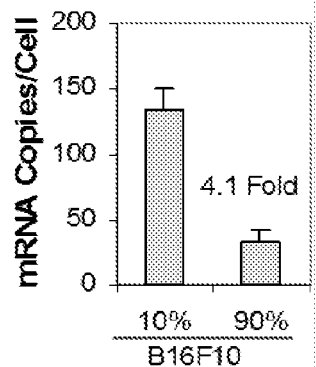
FIG. 3A is a graph that shows TM4SF1 expression in B16F10 cells grown in 10% or 90% confluency.
FIG. 3B shows the number of metastases in 10% (high TM4SF1) or 90% (low TM4SF1)-expressing B16F10 cells.
Figure 3:
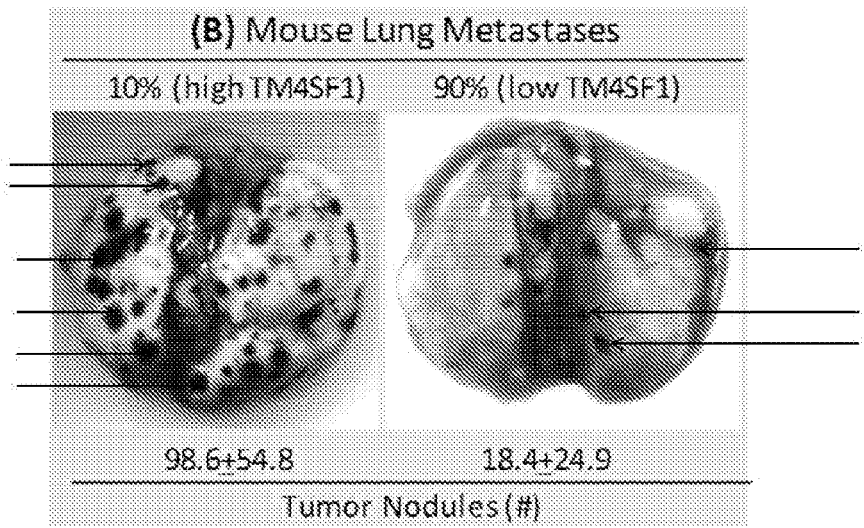

TM4SF1 expression was also studied in B16F10 cells. The results shown in FIG. 3A and FIG. 3B show that metastatic potential of B16F10 TC varies with TM4SF1 expression. As shown in FIG. 3A, TM4SF1 expression levels decreased with confluency. As shown in FIG. 3B, high TM4SF1-expressing B16F10 cells generated more lung metastases than lower TM4SF1 expressors.

Figure 4:
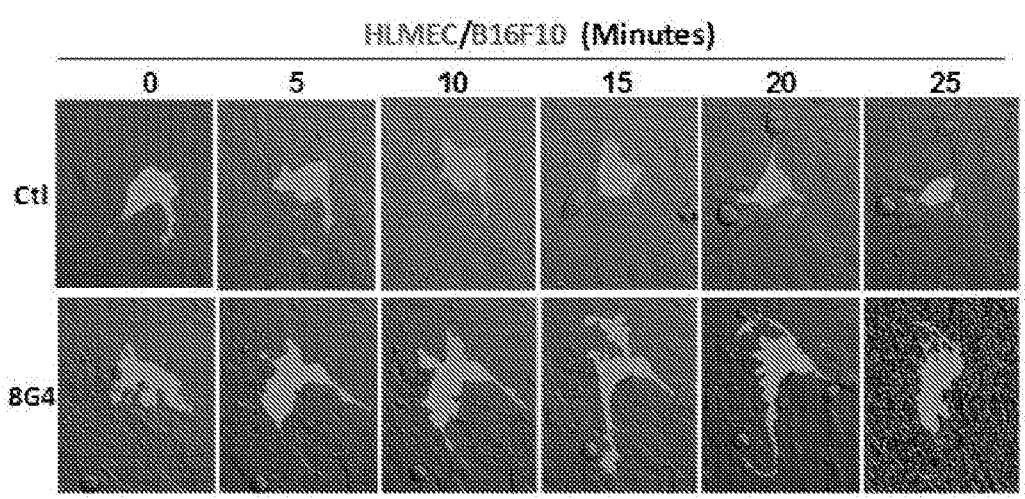
FIG. 4 shows fluorescent live imaging results. GFP-labeled B16F10 cells were layered on a lawn of RFP-labeled HLMEC. Sequential images from a representative live cell imaging show that, in contrast to control (Ctl) antibody, the anti-hTM4SF1 antibody AGX-01 (10 μg/ml) interfered with TC interaction for migration, causing extensive, irregular cell protrusions that resulted in cell detachment.

Further experiments showed that B16F10 cells attach poorly to, migrate abnormally on, and detach frequently from a monolayer of human lung microvascular EC (HLMEC) treated with the anti-TM4SF1 antibody AGX-A01 (FIG. 4; AGX-A01 is referred to as antibody 8G4 in PCT/US2014/059761, variable heavy and light chain of AGX-A01 comprises the amino acid sequences set forth as SEQ ID NO: 1, and SEQ ID NO: 2, respectively). GFP-labeled B16F10 cells were layered on a lawn of RFP-labeled HLMEC. Sequential images from a representative live cell imaging, shown in FIG. 4, demonstrate that, in contrast to control (Ctl) antibody, the anti-TM4SF1 antibody (10 µg/ml) interfered with TC interaction for migration, causing extensive, irregular cell protrusions that resulted in cell detachment.

Example 2. Anti-Human TM4SF1 Antibodies can Inhibit TC-EC Interactions and Block TC Migration A number of exemplary monoclonal antibodies (AGX-A03, AGX-A04, AGX-A05, AGX-A07, AGX-A08, AGX-A09, and AGX-A11) were raised against human TM4SF1 (hTM4SF1). In order to determine their therapeutic value, each of the exemplary anti-hTM4SF1 antibodies are tested to determine which antibodies are able to inhibit tumor cell (TC) attachment to and/or migration across cultured human lung microvascular endothelial cell (EC).

All seven (AGX-A03, AGX-A04, AGX-A05, AGX-A07, AGX-A08, AGX-A09, and AGX-A11) of the exemplary anti-hTM4SF1 antibodies cross react with human and cynomolgous monkey TM4SF1.

In contrast, antibody AGX-A01 (referred to as antibody 8G4 in PCT/US2014/059761) reacted with sub-nanomolar affinity to human, but not cynomolgous monkey TM4SF1. Chimeric antibodies comprising the variable regions of each of the seven antibodies are made and are of isotype human IgG1 with ablated ADCC and CDC effector functions. They react with different epitopes on TM4SF1's ECL-2 loop.

Isotype matched antibodies serve as a control below and throughout the experiments described herein, unless otherwise specified.

Two human breast adenocarcinoma cell lines, MDA-MB-468 and MCF-7, that respectively express high (109±17 mRNA copies/cell) and low (1.5±2.6 mRNA copies/cell) levels of TM4SF1, are selected for these studies. Human lung microvascular endothelial cells (HLMEC) that express TM4SF1 at 120±17 mRNA copies/cell are derived from human lung microvasculature (Lonza Biologics Inc). 10 µg/ml AGX-A01 has been shown to saturate cell surface TM4SF1 binding in flow cytometry in both MDA-MB-468 and HLMEC and was the dose that blocked B16F10 TC-EC interaction shown in FIG. 4. Toxicity to HLMEC in vitro at doses as high as 1 mg/ml AGX-A01 over a 2-day cell culture was not observed.

Determination of Antibody Concentrations that Inhibit EC-TC Interactions (TC Attachment to ECs and or Trans-EC Migration)

Studies are performed to determine antibody concentrations that inhibit EC-TC interactions (TC attachment to ECs and/or trans-EC migration). HLMEC are grown to form monolayers in 4-well slide chambers. Antibodies (each of the 7 anti-hTM4SF1 test antibodies or isotype-matched control antibodies) at serial dilutions of 100, 10, 1, and 0 µg/ml, are added to each well to allow equilibration with HLMEC for 0.5 h before addition of $10^3$ GFP-transfected TCs. One hour and 4 hours later, culture medium is removed after gentle rinsing to eliminate loosely bound or detached TCs, and the chambers are washed once with warm culture medium and then fixed with 37° C. pre-warmed paraformaldehyde. EVOS FL Auto Cell Imaging System (ThermoFisher) are employed to scan entire wells with the Z-stack function from top of the monolayer to the matrix bottom. Individual images are then automatically stitched and Z-stacked together through EVOS and fluorescence signals counted to obtain the number of attached and transmigrated TCs. Live cell imaging is also conducted using the EVOS imaging system to observe EC-TC interactions as they take place.

It is observed that each one the seven exemplary anti-hTM4SF1 test antibodies inhibit TC attachment to HLMEC monolayer. It is further observed that each one the eight exemplary anti-hTM4SF1 antibodies inhibit migration across a HLMEC monolayer.

Example 3. Anti-TM4SF1 Antibody Dosing Regimen

The following experiments are performed to determine a dosing regimen, for an exemplary anti-TM4SF1 antibody of the present disclosure that establishes and maintains long term TM4SF1 immunoblockade in C57Bl/6 mice. The dosing regimen will maximally inhibit TM4SF1-mediated metastasis by injecting an amount of an exemplary anti-TM4SF1 antibody sufficient to saturate TM4SF1 expressed on normal vascular ECs of C57Bl/6 mice.

The "saturating dose," as defined here in Example 3, is the dose at which the number of injected exemplary anti-TM4SF1 antibody is equal to the number of available binding sites in mice in vivo. Pharmacokinetic (PK) assays at various doses of the exemplary anti-TM4SF1 antibodies will identify the saturating dose because the serum anti-TM4SF1 antibody concentration rises rapidly as soon as the injected dose exceeds the saturating dose. Table 1, shown below, summarizes the anticipated relationship between injected dose, serum concentration, and level of immunoblockade for an exemplary anti-TM4SF1 antibody having an affinity Kd of about 0.5 nM.

TABLE 1

Exemplary relationship between injected dose, serum concentration and immunoblockade % for an exemplary anti-TM4SF1 antibody

| Injected dose (as % of saturating dose) | Equilibrium serum concentration (μg/ml) | Immunoblockade (%) |
|---|---|---|
| 20 | 0.018 | 20% |
| 40 | 0.05 | 40% |
| 60 | 0.1 | 60% |
| 80 | 0.3 | 80% |
| 100 | 4.8 | 98.50% |
| 120 | 63.7 | 99.90% |
| 140 | 126.8 | 99.90% |

In certain instances it is observed that administration of an exemplary anti-TM4SF1 test antibody at 3 mg/kg reaches a serum concentration of around 0.07 μg/ml in 12 hours, slightly above the expected equilibrium serum concentration. In contrast, the anti-hTM4SF1 antibody (AGX-A01), which does not interact with any mouse proteins, maintains a serum level of >5 μg/ml for more than twelve days with the same dose and without inducing an antibody response.

3.1 Determination of Initial Dose of an Exemplary Anti-TM4SF1 Test Antibody Needed to Achieve High Level Immunoblockade at 1 Week A study is performed whereby an exemplary anti-TM4SF1 test antibody is administered as a single dose at 30 mg/kg to a mouse. Twenty-four hours following intraperitoneal administration of the anti-TM4SF1 antibody, B16F10 metastatic TCs are injected into the mice. It is observed that mice receiving the anti-mTM4SF1 antibody show reduced lung metastases, for example by about 83%, versus control mice who are injected with tumor cells but are not treated with the exemplary anti-TM4SF1 test antibody.

In a further experiment, the saturating dose of an exemplary anti-TM4SF1 test antibody is identified through a series of PK assays consisting of a single higher (40 mg/kg) dose, as well as two lower (20 and 10 mg/kg) doses of the exemplary anti-mTM4SF1 test antibody to groups of five eight week old female C57Bl/6 mice.

Level of the exemplary anti-TM4SF1 test antibody present in serum is assayed by flow cytometry. Briefly, blood (~30 μl) is collected, and sera is diluted as necessary in PBS for incubation with MS1 mouse ECs which express high levels of mouse TM4SF1 (215±27 TM4SF1 mRNA copies/cell) for 30 min at 4° C. Cells are then washed in PBS to remove unbound antibody and incubated with AlexaFlour-488 labeled anti-human $2^{nd}$ antibody for 30 min at 4° C. Amounts of the exemplary anti-TM4SF1 test antibodies present is determined from a standard curve generated using 10-fold serially diluted concentrations of anti-TM4SF1 antibodies. This assay typically has a sensitivity of 0.001 μg/ml. It is found, in certain cases, that the immunoblockade is about 93% with serum levels of 1 μg/ml and 98.5% with serum levels of about 5 μg/ml.

The goal of these experiments is to identify an initial dose that, at one week, achieves circulating antibody concentrations >1 μg/ml, e.g., at ~5 μg/ml.

3.2 Determination of the Size of Weekly Maintenance Dose Needed to Maintain Long Term, High Level Immunoblockade The goal of this experiment is to identify a weekly maintenance dose for an exemplary anti-TM4SF1 test antibody that maintains high level immunoblockade of vascular TM4SF1, indicated by a level of anti-mTM4SF1 antibody in the circulation consistently above 1 μg/ml.

The desired weekly maintenance dose maintains the serum concentration of the exemplary anti-TM4SF1 test antibody above 1 μg/ml, and ideally close to 5 μg/ml, for at least seven days until the next maintenance dose injection. To determine the maintenance dose, the initial dose determined above in 3.1 is used as the starting dose, and then at about day 7, maintenance doses equal to 100%, 50%, 25% and 0% of the initial dose are tested. Depending on day-14 serum concentrations of the exemplary anti-TM4SF1 test antibodies, day-14 maintenance doses are adjusted in each group of mice to bring the serum concentration 7 days post-injection into the desired 1-5 μg/ml range. This cycle is repeated until all groups converge to the same maintenance dose. With control antibody groups, these experiments use 120 eight week old female C57Bl/6 mice (2 antibodies×4 groups×5 mice/group x repeat 3 times).

3.3. Monitoring for Toxicity and Anti-mTM4SF1 Immunogenicity

Experiments are performed to determine toxicity in mice which are administered a weekly maintenance dose of an exemplary anti-TM4SF1 test antibody. The weekly maintenance dose determined in Example 3.2 is continued for a period of at least 3 months and the mice are monitored for signs of toxicity and anti-TM4SF1 test antibody immunogenicity.

To assure maintenance of the immunoblockade and to examine whether mice have developed antibodies against anti-mTM4SF antibodies, blood is drawn weekly and the following is assessed: (a) serum concentration of anti-TM4SF1 test antibodies; and (b) possible presence of any anti-TM4SF1 test antibodies that have developed by an ELISA assay using a plate coated with the anti-TM4SF1 test antibody being assayed and anti-mouse IgG $2^{nd}$ antibody. These experiments include 30 mice (2 antibodies x 5 mice/group x repeat 3 times).

Example 4. Anti-Metastatic Potential of Exemplary Anti-TM4SF1 Test Antibodies in Two Mouse Models of Lung Metastasis The efficacy of three levels of immunoblockade is tested in B10F10 melanoma tumor cells and in MMTV Pyt (mouse mammary tumor polyomavirus middle T Antigen). The dosing is such that 100%, 50%, and 25% of the dosing schedule identified in Example 3, above, and the resulting metastatic burden in the lung is quantified.

In both models, the number of metastases as a function of the level of immunoblockade is quantified, with a goal of achieving at least a 50% reduction of lung metastases.

4.1. Quantification of Lung Metastases Following iv (Tail Vein) Injection of B16F10 TC TCs ($2 \times 10^5$ cells in 100 µl PBS) injected via tail vein are cleared from the circulation by the lungs after first passage; visible lung metastases develop by 14 days. Metastases is evaluated by standard methods (e.g., as described in Overwijk W W, Restifo N P. B16 as a mouse model for human melanoma. Curr Protoc Immunol 2001; Chapter 20: Unit 20 1; Brown L M, Welch D R, Rannels S R. B16F10 melanoma cell colonization of mouse lung is enhanced by partial pneumonectomy. Clin Exp Metastasis 2002; 19:369-76.35; Khanna C, Hunter K. Modeling metastasis in vivo. Carcinogenesis 2005; 26:513-23), counting the total number of visible tumor nodules and numbers of large (>1 mm diameter) vs small tumor nodules (<1 mm diameter).

4.1.1. Treatment of Mice with Exemplary Anti-TM4SF1 Test Antibodies.

Studies are performed to determine whether, and to what extent, the metastatic burden in the lung is a function of the degree of TM4SF1 immunoblockade. Three levels of anti-TM4SF1 test antibody immunoblockade are tested based on the results of Example 3.1: a single injection of the exemplary anti-TM4SF1 test antibody dose that achieves 100% blockade (e.g., 1-5 µg/ml the anti-TM4SF1 test antibody in serum), and doses representing 50% and 25% of that dose. B16F10 cell injection are performed on day-4 after antibody injection, which is typically about the time when the immunoblockade begins approaching 100% immunoblockade. Mice are sacrificed 14 days after B16F10 cell injection, i.e., 18 days after the initial injection. Blood samples are taken on days-0, −4 (prior to cell injection), +7 (post cell injection), +14, and +18 to assess the serum concentrations of the anti-TM4SF1 test antibodies. Including control antibody groups, 90 eight-week old female C57Bl/6 mice (2 antibodies x 3 doses/antibody×5 mice/group×repeat 3 times) are used in the study.

4.1.2. Treatment of TCs with Anti-mTM4SF1 Antibodies Prior to Injection into Mice B16F10 cells express high levels of TM4SF1 (~130 TM4SF1 mRNA copies/cell after overnight culture at 10% confluency; as shown in FIG. 3A). The effect of selective immunoblockade of TC TM4SF1 on lung metastasis is examined in this study. These experiments follow the protocol set out in Example 4.1.1 except that TCs are incubated with 10 g/ml exemplary anti-TM4SF1 antibodies for 1 h at 4° C. to saturate the TM4SF1 binding sites and then washed to remove unbound anti-TM4SF1 test antibodies prior to injection into mice. For an exemplary anti-TM4SF1 test antibody and control antibodies, 30 mice (2 antibodies x 1 doses/antibody×5 mice/group×repeat 3 times) are used in the study.

TCs treated as described above are subsequently injected via tail vein and are found to be cleared from the circulation after first passage through the lung, thereby demonstrating that immunoblockade of TC TM4SF1 contributes to metastasis inhibition in mice in vivo.

4.2. Spontaneous Lung Metastasis in the MMTV-Pyt Model

The MMTV-Pyt mouse mammary tumor metastasis model recapitulates the progression of human cancers from hyperplasia to pre-malignant and then to frankly invasive ductal carcinomas with metastatic potential by age 8-12 weeks. After age 8 weeks, TCs are shed continuously, replicating the clinical situation in humans in which a continuous immunoblockade will be necessary to prevent metastases. Visible lung metastases appear beginning at approximately week 13.

To test the efficacy of an exemplary anti-TM4SF1 test antibody, antibody treatment is administered beginning in 8 week old female MMTV-Pyt mice, as this is the age when primary malignant tumors first appear in mammary glands. The anti-TM4SF1 test antibody dosing schedule developed in Example 3 is used here. Mice are sacrificed at 16 weeks. The number and mass of lung metastases is assessed, counting metastases as described in Example 4.1. With control antibody, 90 seven-week old female Pyt mice (2 antibodies x 3 doses/Ab×5 mice/group×repeat 3 times) are used for the study.

It is possible that, because both TC and angiogenic EC in tumor vessels are actively metabolizing and dividing cells that are constantly generating new surface TM4SF1, the presence of tumors (both primary in mammary glands and lung metastases) may increase the dose of the anti-TM4SF1 test antibodies required to maintain immunoblockade. As a result, the dosing schedule developed in tumor-free mice in Example 3 is, in certain instances, adjusted to maintain an equivalent immunoblockade in tumor-bearing mice of Example 4.2. PK assessments of circulating anti-TM4SF1 test antibody levels is made regularly to verify that serum antibody level remains above 1 µg/ml; if they do not, additional antibody is injected to maintain the desired immunoblockade.

While it is possible that anti-TM4SF1 antibodies (directed against the human IgG backbone) can develop during the 8 weeks of experimental period, such antibodies are not found to have developed by 12 days. If anti-TM4SF1 antibodies are developed, the study is repeated with exemplary anti-TM4SF1 antibodies that include a mouse IgG backbone instead of a human IgG.

In both models described herein, the goal is to quantify the metastatic burden in the lung as a function of the degree of TM4SF1 immunoblockade and achieve at least a 50% reduction in lung metastasis.

Example 5. Humanized Mutated TM4SF1 Antibodies can Bind TM4SF1 in Primary Endothelial Cells Human umbilical vein endothelial cells (HUVEC) were pre-labeled with various test antibodies (1 µg/ml), at 4° C. and returned to culture at 37° C.

The test antibodies used in this study were: humanized AGX-A07 H2L5 (comprising a light chain amino acid sequence as set forth in SEQ ID NO: 97 (AGX-A07 L5) and a heavy chain amino acid sequence as set forth in SEQ ID NO: 90 (AGX-A07 H2)); humanized mutated (hm) AGX-A07 H2L5 V1 (comprising a light chain amino acid sequence as set forth in SEQ ID NO: 99 (AGX-A07 L5v1) and a heavy chain amino acid sequence as set forth in SEQ ID NO: 92 (AGX-A07 H2v1)); hm AGX-A07 H2L5 V2 (comprising a light chain amino acid sequence as set forth in SEQ ID NO: 101 (AGX-A07 L5v2) and a heavy chain amino acid sequence as set forth in SEQ ID NO: 92 (AGX-A07 H2v1)); hm AGX-A07 H2L5 V3 (comprising a light chain amino acid sequence as set forth in SEQ ID NO: 103 (AGX-A07 L5v3) and a heavy chain amino acid sequence as set forth in SEQ ID NO: 92 (AGX-A07 H2v1)); hm AGX-A07 H2L5 V4 (comprising a light chain amino acid sequence as set forth in SEQ ID NO: 105 (AGX-A07 L5v4) and a heavy chain amino acid sequence as set forth in SEQ ID NO: 92 (AGX-A07 H2v1)); and humanized AGX-A01.

Figure 12:
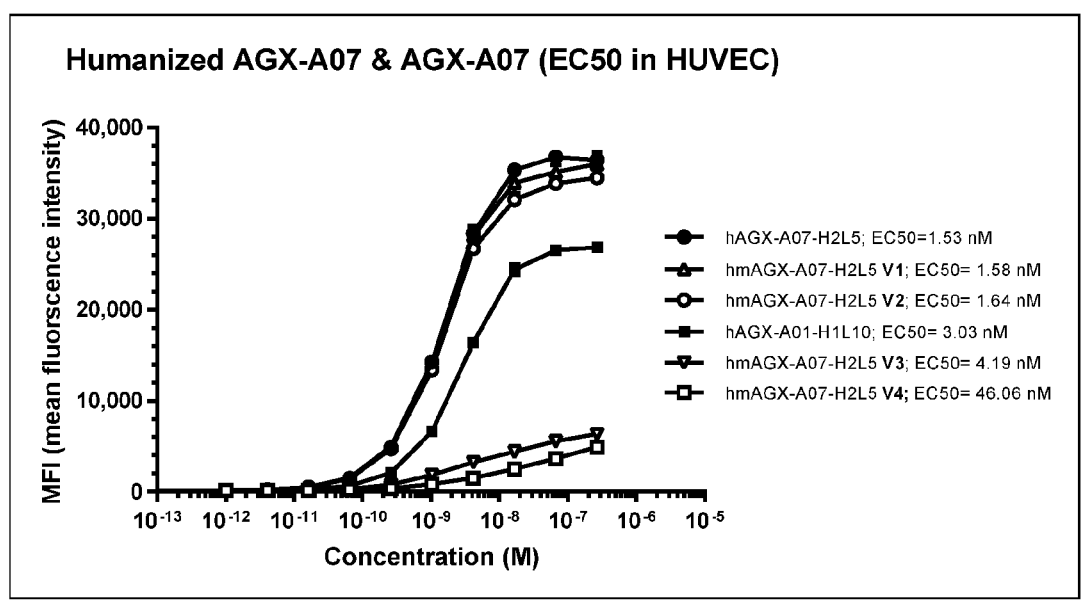
FIG. 12 shows target binding of several anti-TM4SF1 antibodies of this disclosure, h AGX-A07 H2L5, hm AGX- A07 H2L5 V1, hm AGX-A07 H2L5 V2, hm AGX-A07 H2L5 V3, hm AGX-A07 V4, and h AGX-A01 H1L10.

As shown in the mean fluorescence intensity (MFI) plot of FIG. 12, test antibodies hAGX-A07 H2L5, hm AGX-A07 H2L5 V1 and hm AGX-A07 H2L5 V2, comprising light chain sequences with a tryptophan residue at position 90, were superior in binding HUVEC cells (as indicated by the high MFI values for h AGX-A07 H2L5, hm AGX-A07 H2L5 V1, hm AGX-A07 H2L5 V2; and $EC_{50}$ for hAGX-A07 H2L5=1.53 nM; $EC_{50}$ for hm AGX-A07 H2L5 V1=1.58 nM, $EC_{50}$ for hm AGX-A07 H2L5 V2=1.64 nM), compared to test antibodies hm AGX-A07 H2L5 V3 and hm AGX-A07 H2L5 V4, comprising light chain sequences with a tryptophan to tyrosine substitution at position 90 (W90Y) (as demonstrated by the lower MFI values for hm AGX-A07 H2L5 V3 and hm AGX-A07 H2L5 V4; $EC_{50}$ for hm AGX-A07 H2L5 V3=4.19 nM; $EC_{50}$ for hm AGX-A07 H2L5 V4=46.06 nM). Humanized AGX-A01 was also able to bind with an $EC_{50}$=3.03 nM.

Figure 13:
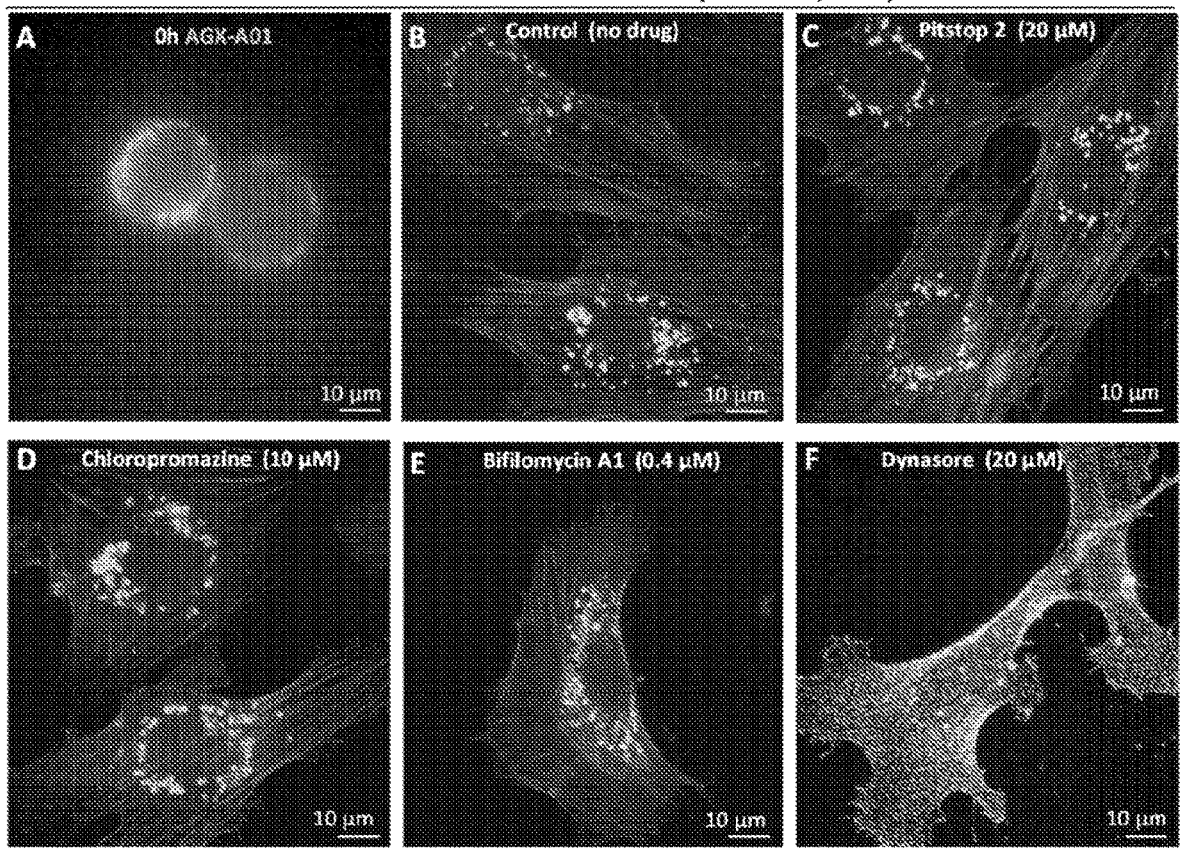
FIG. 13 shows effect on internalization of TM4SF1 in HUVEC in the presence of different inhibitors.

Example 6. Internationalization of TM4SF1 in Primary Endothelial Cells Pre-Labeled with anti-TM4SF1 Antibodies Human umbilical vein endothelial cells (HUVEC) were pre-labeled with AGX-A01 (1 µg/ml) at 4° C. (staining shown in FIG. 13(A)) and returned to culture at 37° C. without (as shown in FIG. 13(B)) or in the presence of the following inhibitors: 20 µM pitstop-2 (clathrin inhibitor) (as shown in FIG. 13(C)); 10 µM chloropromazine (clathrin and caveolin mediated endocytosis inhibitor) (as shown in FIG. 13(D)); 0.4 µM bifilomycin A (autophagy inhibitor) (as shown in FIG. 13 (E)); or 20 µM dynasore (dynamin inhibitor) (as shown in FIG. 13(F)). After 4 hours, cells were fixed in 4% paraformaldehyde and stained with Alexa-488 labeled donkey anti-human Ab, phallodin (to stain actin fibers) and DAPI (to stain nuclei). Immunocytochemistry demonstrated substantial and equivalent AGX-A01 uptake at 4 hours with no added inhibitor (FIG. 13(A)) or in the presence of pitstop-2 (FIG. 13(C)), chloropromazine (FIG. 13(D)), or bifilomycin A (FIG. 13 (E)). However, AGX-A01 remained largely on the cell surface when cultured with dynasore (FIG. 13(F)).

TABLE 2

SEQUENCE DESCRIPTION

| SEQ ID NO | Description | Sequence |
|---|---|---|
| Antibody AGX-A01 | | |
| 1 | AGX-A01 Variable heavy (VH) chain- amino acid | EVILVESGGGLVKPGGSLKLSCAASGFTFSSF AMSWVRQTPEKRLEWVATISSGSIYIYYTDG VKGRFTISRDNAKNTVHLQMSSLRSEDTAM YYCARRGIYYGYDGYAMDYWGQGTSVTVS |
| 2 | AGX-A01 Variable light (VL) chain- amino acid | AVVMTQTPLSLPVSLGDQASISCRSSQSLVHS NGNTYLHWYMQKPGQSPKVLIYKVSNRFSG VPDRFSGSGSGTDFTLKISRVEADDLGIYFCS QSTHIPLAFGAGTKLELK |
| Antibody AGX-A03 | | |
| 3 | AGX-A03 Variable heavy (VH) chain- amino acid | QIQLVQSGPELKKPGETVKISCKASGYSFRDY GMNWVKQAPGRTFKWMGWINTYTGAPVY AADFKGRFAFSLDTSASAAFLQINNLKNEDT ATYFCARWVSYGNNRNWFFDFWGAGTTVT VSS |
| 4 | AGX-A03 Variable heavy (VH) chain- nucleic acid | CAGATCCAGTTGGTGCAGTCTGGACCTGAG CTGAAGAAGCCTGGAGAGACAGTCAAGAT CTCCTGCAAGGCTTCTGGGTATTCCTTCAG AGACTATGGAATGAACTGGGTGAAGCAGG CTCCAGGAAGGACTTTTAAGTGGATGGGCT GGATAAACACCTACACTGGAGCGCCAGTA TATGCTGCTGACTTCAAGGGACGGTTTGCC TTCTCTTTGGACACCTCTGCCAGCGCTGCC TTTTTGCAGATCAACAACCTCAAAAATGAA GACACGGCTACATATTTCTGTGCAAGATGG GTCTCCTACGGTAATAACCGCAACTGGTTC TTCGATTTTTGGGGCGCAGGGACCACGGTC ACCGTCTCCTCA |

TABLE 2-continued

SEQUENCE DESCRIPTION

| SEQ ID NO | Description | Sequence |
|---|---|---|
| 5 | AGX-A03 Variable heavy (VH) chain- codon optimized nucleic acid | CAAATTCAGTTGGTTCAATCCGGCCCTGAG CTCAAGAAGCCTGGAGAGACAGTGAAGAT AAGTTGTAAGGCTAGTGGCTATTCATTTCG AGATTATGGGATGAATTGGGTCAAGCAGG CCCCAGGGCGGACCTTCAAATGGATGGGG TGGATCAATACTTACACTGGCGCACCAGTA TATGCAGCTGATTTTAAGGGTCGCTTTGCA TTTTCACTTGATACTTCAGCCAGTGCCGCT TTTTTGCAAATCAACAATCTCAAAAATGAA GACACTGCTACATATTTCTGCGCCAGGTGG GTGAGCTATGGCAATAACAGAAATTGGTT CTTTGACTTTTGGGGCGCAGGCACCACCGT CACTGTCTCATCA |
| 6 | VH-CDR1 | GYSFRDYGMN |
| 7 | VH-CDR2 | WINTYTGAPVYAADFKG |
| 8 | VH-CDR3 | WVSYGNNRNWFFDF |
| 9 | AGX-A03 Variable light (VL) chain- amino acid | DVLMTQTPLSLPVRLGDQASISCRSSQTLVHS NGNTYLEWYLQKPGQSPKLLIYKVSNRLSG VPDRFSGSGSGTDFTLKISRVETEDLGVYYCF QGSHGPWTFGGGTKLEIK |
| 10 | AGX-A03 Variable light (VL) chain- nucleic acid | GATGTTTTGATGACCCAAACTCCACTCTCC CTGCCTGTCCGTCTTGGAGATCAGGCCTCC ATCTCTTGTAGATCTAGTCAGACCCTTGTA CATAGTAATGGAAACACCTATTTAGAATG GTACCTGCAGAAACCAGGCCAGTCTCCAA AACTCTTGATCTACAAAGTTTCCAATCGAC TTTCTGGGGTCCCAGACAGGTTCAGTGGCA GTGGATCAGGGACAGATTTCACACTCAAG ATCAGCAGAGTGGAGACTGAGGATCTGGG AGTTTATTACTGCTTTCAAGGTTCACATGG TCCGTGGACGTTCGGTGGAGGCACCAAGC TGGAAATCAAA |
| 11 | AGX-A03 Variable light (VL) chain- codon optimized nucleic acid | GACGTACTTATGACACAAACTCCCTTGAGC TTGCCAGTACGGCTTGGCGATCAAGCTTCA ATTTCATGTCGTTCTTCTCAAACACTTGTCC ACTCAAATGGGAATACATATTTGGAATGGT ATCTCCAAAAGCCCGGCCAATCCCCAAAA TTGTTGATTTACAAGGTGTCTAATCGACTC TCAGGCGTCCCCGACCGATTCTCCGGGAGC GGGTCCGGTACAGACTTCACCTTGAAAATC TCCAGGGTAGAAACTGAAGACCTCGGAGT CTACTATTGTTTCCAGGGGTCACACGGCCC CTGGACATTTGGAGGAGGAACTAAGCTCG AGATCAAA |
| 12 | VL-CDR1 | RSSQTLVHSNGNTYLE |
| 13 | VL-CDR2 | KVSNRLS |
| 14 | VL-CDR3 | FQGSHGPWT |

Antibody AGX-A04

| 15 | AGX-A04 Variable heavy (VH) chain- amino acid | EVQLQQSGPELVKPGASVKISCKTSGYTFTD YTMHWVRQSHGKSLEWIGSFNPNNGGLTNY NQKFKGKATLTVDKSSSTVYMDLRSLTSEDS AVYYCTRIRATGFDSWGQGTTLTVSS |
| 16 | AGX-A04 Variable heavy (VH) chain- nucleic acid | GAGGTCCAGCTGCAACAGTCTGGACCTGA GCTGGTGAAGCCTGGGGCTTCAGTGAAGA TATCCTGCAAGACTTCTGGATACACATTCA CTGATTACACCATGCACTGGGTGAGGCAG AGCCATGGAAAGAGCCTTGAGTGGATTGG AAGTTTTAATCCTAACAATGGTGGTCTTAC TAACTACAACCAGAAGTTCAAGGGCAAGG CCACATTGACTGTGGACAAGTCTTCCAGCA |

TABLE 2-continued

SEQUENCE DESCRIPTION

| SEQ ID NO | Description | Sequence |
|---|---|---|
| | | CAGTGTACATGGACCTCCGCAGCCTGACAT CTGAGGATTCTGCAGTCTATTACTGTACAA GAATCCGGGCTACGGGCTTTGACTCCTGGG GCCAGGGCACCACTCTCACAGTCTCCTCA |
| 17 | AGX-A04 Variable heavy (VH) chain- codon optimized nucleic acid | GAGGTACAACTGCAACAGAGTGGACCTGA ACTTGTCAAACCTGGAGCAAGTGTGAAGA TTAGCTGTAAAACCAGTGGCTACACATTTA CCGATTATACTATGCACTGGGTAAGACAG AGCCACGGAAAATCACTGGAGTGGATTGG TAGTTTCAATCCTAACAACGGAGGATTGAC AAATTACAACCAGAAGTTCAAAGGGAAAG CCACCTTGACAGTTGATAAGTCCTCAAGTA CCGTGTATATGGATCTGCGTTCTCTCACAA GTGAAGATAGCGCAGTTTACTACTGTACCC GCATCCGAGCCACCGGGTTCGATTCATGGG GTCAGGGGACAACACTGACTGTTTCTTCT |
| 18 | VH-CDR1 | GYTFTDYTMH |
| 19 | VH-CDR2 | SFNPNNGGLTNYNQKFKG |
| 20 | VH-CDR3 | IRATGFDS |
| 21 | AGX-A04 Variable light (VL) chain- amino acid | DIVMSQSPSSLAVSAGEKVTMSCKSSQSLLN SRTRKNYLAWYQQKPGQSPKLLIYWASTRE SGVPDRFTGSGSGTDFTLTISNVQAEDLTVY YCKQSYNPPWTFGGGTKLEIK |
| 22 | AGX-A04 Variable light (VL) chain- nucleic acid | GACATTGTGATGTCACAGTCTCCATCCTCC CTGGCTGTGTCAGCAGGAGAGAAGGTCAC TATGAGCTGCAAATCCAGTCAGAGTCTGCT CAACAGTAGAACCCGAAAGAACTACTTGG CTTGGTACCAGCAGAAACCAGGGCAGTCT CCTAAACTGCTGATCTACTGGGCATCCACT AGGGAATCTGGGGTCCCTGATCGCTTCACA GGCAGTGGATCTGGGACAGATTTCACTCTC ACCATCAGCAATGTGCAGGCTGAAGACCT GACAGTTTATTACTGCAAGCAATCTTATAA TCCTCCGTGGACGTTCGGTGGAGGCACCAA GCTGGAAATCAAA |
| 23 | AGX-A04 Variable light (VL) chain- codon optimized nucleic acid | GACATAGTTATGTCCCAGTCTCCATCCAGC TTGGCTGTCAGCGCCGGAGAGAAAGTGAC TATGAGTTGTAAATCTTCCCAGTCCCTGCT TAACTCACGTACTCGGAAGAATTATCTTGC CTGGTATCAACAAAAGCCAGGTCAAAGTC CTAAGCTCCTTATTTACTGGGCCTCAACAC GGGAGTCAGGTGTCCCCGATCGCTTCACAG GTAGTGGGAGTGGTACTGACTTCACTCTCA CCATTTCAAATGTCCAAGCAGAAGACTTGA CTGTGTATTACTGTAAGCAGAGTTACAACC CTCCTTGGACCTTTGGTGGGGGACCAAAC TGGAGATCAAG |
| 24 | VL-CDR1 | KSSQSLLNSRTRKNYLA |
| 25 | VL-CDR2 | WASTRES |
| 26 | VL-CDR3 | KQSYNPPWT |

Antibody AGX-A05

| SEQ ID NO | Description | Sequence |
|---|---|---|
| 27 | AGX-A05 Variable heavy (VH) chain- amino acid | EVQVQQSGPELVKPGASVKMSCKASGYTFT SYVMHWVKQKPGQGLEWIGYINPNNDNINY NEKFKGKASLTSDKSSNTVYMELSSLTSEDS AVYYCAGYGNSGANWGQGTLVTVSA |
| 28 | AGX-A05 Variable heavy (VH) chain- nucleic acid | GAGGTCCAGGTACAGCAGTCTGGACCTGA ACTGGTAAAGCCTGGGGCTTCAGTGAAGA TGTCCTGTAAGGCTTCTGGATACACATTCA CTAGCTATGTCATGCACTGGGTGAAGCAG AAGCCTGGGCAGGGCCTTGAGTGGATTGG ATATATTAATCCTAACAATGATAATATTAA CTACAATGAGAAGTTCAAAGGCAAGGCCT |

TABLE 2-continued

SEQUENCE DESCRIPTION

| SEQ ID NO | Description | Sequence |
|---|---|---|
| | | CACTGACTTCAGACAAATCCTCCAACACAG TCTACATGGAGCTCAGCAGCCTGACCTCTG AGGACTCTGCGGTCTATTACTGTGCAGGCT ATGGTAACTCCGGAGCTAACTGGGGCCAA GGGACTCTGGTCACTGTCTCTGCA |
| 29 | AGX-A05 Variable heavy (VH) chain- codon optimized nucleic acid | GAAGTTCAAGTTCAGCAAAGCGGGCCTGA GCTTGTCAAGCCAGGCGCATCAGTCAAAA TGAGCTGTAAGGCTTCCGGGTACACCTTCA CCAGTTATGTCATGCATTGGGTAAAACAAA AGCCAGGACAGGGACTCGAGTGGATAGGA TACATTAACCCAAATAACGACAACATTAA CTACAACGAGAAATTCAAGGGCAAAGCAT CATTGACTTCCGATAAATCCTCTAACACCG TGTACATGGAGCTGAGTTCATTGACCAGCG AGGATTCTGCCGTGTACTACTGTGCAGGTT ATGGCAACTCTGGTGCTAACTGGGGGCAG GGGACTCTGGTCACAGTCAGCGCA |
| 30 | VH-CDR1 | GYTFTSYVMH |
| 31 | VH-CDR2 | YINPNNDNINYNEKFKG |
| 32 | VH-CDR3 | YGNSGAN |
| 33 | AGX-A05 Variable light (VL) chain- amino acid | DIQMTQSPASLSASVGETVTITCRTSKNIFNF LAWYHQKQGRSPRLLVSHTKTLAAGVPSRFS GSGSGTQFSLKINSLQPEDFGIYYCQHHYGTP WTFGGGTKLEIK |
| 34 | AGX-A05 Variable light (VL) chain- nucleic acid | GACATCCAGATGACTCAGTCTCCAGCCTCC CTATCTGCATCTGTGGGAGAAACTGTCACC ATCACATGTCGAACAAGTAAAAATATTTTC AATTTTTTAGCATGGTATCACCAGAAACAG GGAAGATCTCCTCGACTCCTGGTCTCTCAT ACAAAAACCTTAGCAGCAGGTGTGCCATC AAGGTTCAGTGGCAGTGGCTCAGGCACAC AGTTTTCTCTGAAGATCAACAGCCTGCAGC CTGAAGATTTTGGGATTTATTACTGTCAAC ATCATTATGGTACTCCGTGGACGTTCGGTG GAGGCACCAAACTGGAAATCAAA |
| 35 | AGX-A05 Variable light (VL) chain- codon optimized nucleic acid | GACATTCAGATGACCCAGTCACCAGCATCT TTGAGCGCATCCGTTGGGGAGACTGTGAC AATCACATGCCGAACCAGTAAGAACATCT TCAACTTCCTCGCATGGTACCATCAAAAGC AGGGCAGGTCTCCCAGACTGCTTGTCTCTC ACACCAAGACACTGGCAGCAGGCGTCCCC AGCCGGTTTAGTGGTAGTGGATCTGGCACA CAGTTTAGTTTGAAAATCAATTCCCTGCAA CCCGAAGACTTCGGCATATACTATTGCCAG CACCACTATGGGACACCTTGGACTTTCGGA GGTGGTACTAAACTTGAGATTAAA |
| 36 | VL-CDR1 | RTSKNIFNFLA |
| 37 | VL-CDR2 | HTKTLAA |
| 38 | VL-CDR3 | QHHYGTPWT |
| | Antibody AGX-A07 | |
| 39 | AGX-A07 Variable heavy (VH) chain- amino acid | QIQLVQSGPELKKPGETVKISCKASGYTFTNY GVKWVKQAPGKDLKWMGWINTYTGNPIYA ADFKGRFAFSLETSASTAFLQINNLKNEDTAT YFCVRFQYGDYRYFDVWGAGTTVTVSS |
| 40 | AGX-A07 Variable heavy (VH) chain- nucleic acid | CAGATCCAGTTGGTGCAGTCTGGACCTGAG CTGAAGAAGCCTGGAGAGACAGTCAAGAT CTCCTGCAAGGCTTCTGGGTATACCTTCAC AAACTATGGAGTGAAGTGGGTGAAGCAGG CTCCAGGAAAGGATTTAAAGTGGATGGGC TGGATAAACACCTACACTGGAAATCCAATT TATGCTGCTGACTTCAAGGGACGGTTTGCC TTCTCTTTGGAGACCTCTGCCAGCACTGCC |

TABLE 2-continued

SEQUENCE DESCRIPTION

| SEQ ID NO | Description | Sequence |
|---|---|---|
|  |  | TTTTTGCAGATCAACAACCTCAAAAATGAG GACACGGCTACATATTTCTGTGTAAGATTC CAATATGGCGATTACCGGTACTTCGATGTC TGGGGCGCAGGGACCACGGTCACCGTCTC CTCA |
| 41 | AGX-A07 Variable heavy (VH) chain- codon optimized nucleic acid | CAAATCCAACTTGTCCAGAGCGGTCCCGA GTTGAAGAAGCCTGGCGAAACCGTGAAAA TCTCATGCAAGGCCAGTGGATATACATTTA CAAACTATGGCGTCAAGTGGGTGAAACAA GCCCCAGGTAAAGACTTGAAATGGATGGG ATGGATCAACACATACACAGGGAATCCTA TCTATGCAGCCGACTTTAAAGGCAGATTTG CCTTCAGTTTGGAGACATCTGCCTCCACCG CTTTCCTGCAAATAAATAACCTGAAAAATG AAGATACCGCTACATACTTCTGTGTACGGT TCCAGTACGGAGATTACCGCTATTTCGATG TGTGGGGCGCAGGTACCACAGTAACCGTC TCCTCA |
| 42 | VH-CDR1 | GYTFTNYGVK |
| 43 | VH-CDR2 | WINTYTGNPIYAADFKG |
| 44 | VH-CDR3 | FQYGDYRYFDV |
| 45 | AGX-A07 Variable light (VL) chain- amino acid | QIILSQSPAILSASPGEKVTMTCRANSGISFI NWYQQKPGSSPKPWIYGTANLASGVPARFGG SGSGTSYSLTISRVEAEDAATYYCQQWSSNP LTFGAGTKLELR |
| 46 | AGX-A07 Variable light (VL) chain- nucleic acid | CAAATTATTCTCTCCCAGTCTCCAGCAATC CTGTCTGCATCTCCAGGGGAGAAGGTCAC CGATGACTTGCAGGGCCAACTCAGGTATTA GTTTCATCAACTGGTACCAGCAGAAGCCA GGATCCTCCCCCAAACCCTGGATTTATGGC ACAGCCAACCTGGCTTCTGGAGTCCCTGCT CGCTTCGGTGGCAGTGGGTCTGGGACTTCT TACTCTCTCACAATCAGCAGAGTGGAGGCT GAAGACGCTGCCACTTATTACTGCCAGCAG TGGAGTAGTAACCCGCTCACGTTCGGTGCT GGGACCAAGCTGGAGTTGAGA |
| 47 | AGX-A07 Variable light (VL) chain- codon optimized nucleic acid | CAAATAATTCTGTCACAGTCCCCCGCTATA CTTAGTGCTTCACCAGGAGAAAAAGTGAC CATGACTTGTAGAGCTAATTCTGGCATATC ATTCATCAACTGGTATCAACAAAAGCCAG GTTCCTCCCCCAAGCCATGGATTTACGGGA CCGCCAACCTTGCTTCTGGGGTACCCGCTC GTTTCGGCGGATCAGGTTCAGGAACTTCCT ATAGCCTCACTATCAGTCGGGTTGAAGCTG AGGATGCCGCTACATATTACTGCCAGCAAT GGTCTAGTAATCCACTTACCTTTGGAGCTG GCACCAAATTGGAACTTCGT |
| 48 | VL-CDR1 | RANSGISFIN |
| 49 | VL-CDR2 | GTANLAS |
| 50 | VL-CDR3 | QQWSSNPLT |

Antibody AGX-A08

| 51 | AGX-A08 Variable heavy chain (VH)- amino acid | EVQLQQSGPELVKPGASVKLSCKASGYTVTS YVMHWVKQKPGQGLEWIGYINPYSDVTNC NEKFKGKATLTSDKTSSTAYMELSSLTSEDS AVYYCSSYGGGFAYWGQGTLVTVSA |
| 52 | AGX-A08 Variable heavy (VH) chain- nucleic acid | GAGGTCCAGCTGCAGCAGTCTGGACCTGA GCTGGTAAAGCCTGGGGCTTCAGTGAAGC TGTCCTGCAAGGCTTCTGGATACACAGTCA CTAGCTATGTTATGCACTGGGTGAAGCAGA AGCCTGGGCAGGGCCTTGAGTGGATTGGA TATATTAATCCTTACAGTGATGTTACTAAC TGCAATGAGAAGTTCAAAGGCAAGGCCAC |

TABLE 2-continued

SEQUENCE DESCRIPTION

| SEQ ID NO | Description | Sequence |
|---|---|---|
|  |  | ACTGACTTCAGACAAAACCTCCAGCACAG CCTACATGGAGCTCAGCAGCCTGACCTCTG AGGACTCTGCGGTCTATTACTGTTCCTCCT ACGGTGGGGGTTTGCTTACTGGGGCCAA GGGACTCTGGTCACTGTCTCTGCA |
| 53 | AGX-A08 Variable heavy (VH) chain-codon optimized nucleic acid | GAAGTCCAGCTTCAGCAATCCGGCCCAGA ACTGGTAAAACCAGGCGCAAGTGTTAAGT TGAGTTGCAAAGCCAGTGGTTATACCGTTA CTTCATACGTCATGCATTGGGTAAAACAAA AGCCCGGCCAAGGGCTTGAATGGATCGGC TACATCAACCCTTACTCTGACGTCACCAAC TGCAACGAGAAATTCAAAGGGAAAGCCAC ATTGACCTCTGACAAGACAAGCAGTACCG CCTACATGGAGCTTTCTAGTTTGACTTCTG AAGACTCTGCTGTCTACTACTGTAGCAGCT ACGGCGGCGGCTTTGCTTACTGGGGCCAG GGTACATTGGTGACTGTGAGTGCA |
| 54 | VH-CDR1 | GYTVTSYVMH |
| 55 | VH-CDR2 | YINPYSDVTNCNEKFKG |
| 56 | VH-CDR3 | YGGGFAY |
| 57 | AGX-A08 Variable light chain(VL)-amino acid | DIQMTQSPASLSASVGEPVTITCRASKNIYTY LAWYHQKGKSPQFLVYNARTLAGGVPSRL SGSGSVTQFSLNINTLHREDLGTYFCQHHYD TPYTFGGGTNLEIK |
| 58 | AGX-A08 Variable light (VL) chain-nucleic acid | GACATCCAGATGACTCAGTCTCCAGCCTCC CTATCTGCATCTGTGGGAGAACCTGTCACC ATCACATGTCGAGCAAGTAAGAATATTTAC ACATATTTAGCATGGTATCACCAGAAACA GGGAAAATCTCCTCAGTTCCTGGTCTATAA TGCAAGAACCTTAGCAGGAGGTGTGCCAT CAAGGCTCAGTGGCAGTGGATCAGTCACG CAGTTTTCTCTAAACATCAACACCTTGCAT CGAGAAGATTTAGGGACTTACTTCTGTCAA CATCATTATGATACTCCGTACACGTTCGGA GGGGGGACCAACCTGGAAATAAAA |
| 59 | AGX-A08 Variable light (VL) chain-codon optimized nucleic acid | GACATCCAGATGACACAGTCACCAGCATC CCTGTCCGCCTCAGTTGGGGAGCCTGTTAC CATAACTTGTCGGGCAAGCAAAAACATAT ACACCTATTTGGCTTGGTATCACCAAAAGC AAGGTAAGTCACCTCAGTTTCTTGTATATA ATGCCCGCACACTTGCTGGCGGAGTACCCT CTCGATTGTCTGGATCTGGCAGCGTTACCC AATTCAGCCTGAACATCAACACCCTCCATC GGGAAGATTTGGGTACCTATTTCTGTCAAC ATCACTACGACACCCCATACACCTTCGGAG GCGGCACAAATTTGGAAATTAAA |
| 60 | VL-CDR1 | RASKNIYTYLA |
| 61 | VL-CDR2 | NARTLAG |
| 62 | VL-CDR3 | QHHYDTPYT |

Antibody AGX-A09

| SEQ ID NO | Description | Sequence |
|---|---|---|
| 63 | AGX-A09 Variable heavy (VH) chain-amino acid | EVQLQQSGPELVKPGASVKMSCKASGYTFSS YVMHWVKQKPGQGLEWIGYINPYSDVTNY NEKFKGKATLTSDRSSNTAYMELSSLTSEDS AVYYCARNYFDWGRGTLVTVSA |
| 64 | AGX-A09 Variable heavy (VH) chain-nucleic acid | GAGGTCCAGCTGCAGCAGTCTGGACCTGA GCTGGTAAAGCCTGGGGCTTCAGTGAAGA TGTCCTGCAAGGCTTCTGGATACACATTCT CTAGCTATGTTATGCACTGGGTGAAGCAGA AGCCTGGGCAGGGCCTTGAGTGGATTGGA TATATTAATCCTTACAGTGATGTCACTAAC TACAATGAGAAGTTCAAAGGCAAGGCCAC ACTGACTTCAGACAGATCCTCCAACACAGC |

TABLE 2-continued

SEQUENCE DESCRIPTION

| SEQ ID NO | Description | Sequence |
|---|---|---|
| | | CTACATGGAACTCAGCAGCCTGACCTCTGA GGACTCTGCGGTCTATTACTGTGCAAGAAA TTACTTCGACTGGGGCCGAGGGACTCTGGT CACAGTCTCTGCA |
| 65 | AGX-A09 Variable heavy (VH) chain-codon optimized nucleic acid | GAGGTACAGCTTCAGCAGAGTGGTCCAGA ACTCGTCAAGCCTGGGGCAAGCGTTAAGA TGAGTTGTAAAGCATCCGGTTACACATTCA GTAGCTATGTTATGCACTGGGTCAAACAGA AGCCTGGGCAGGGGTTGGAGTGGATCGGA TATATAAATCCCTATTCAGACGTAACTAAT TATAATGAAAAGTTCAAGGGGAAAGCAAC CTTGACAAGTGACCGGTCATCTAATACCGC ATACATGGAGCTGAGCTCATTGACAAGTG AGGACTCTGCTGTGTATTACTGTGCCCGGA ACTACTTCGACTGGGGTAGGGGCACACTG GTAACTGTTAGTGCA |
| 66 | VH-CDR1 | GYTFSSYVMH |
| 67 | VH-CDR2 | YINPYSDVTNYNEKFKG |
| 68 | VH-CDR3 | NYFD |
| 69 | AGX-A09 Variable light (VL) chain-amino acid | DIQMTQSPASLSASVGETVTITCRASKNVYS YLAWFQQKQGKSPQLLVYNAKTLAEGVPSR FSGGGSGTQFSLKINSLQPADFGSYYCQHHY NIPFTFGSGTKLEIK |
| 70 | AGX-A09 Variable light (VL) chain-nucleic acid | GACATCCAGATGACTCAGTCTCCAGCCTCC CTATCTGCATCTGTGGGAGAAACTGTCACC ATCACATGTCGAGCAAGTAAAAATGTTTAC AGTTATTTAGCATGGTTTCAACAGAAACAG GGGAAATCTCCTCAGCTCCTGGTCTATAAT GCTAAAACCTTAGCAGAAGGTGTGCCATC AAGGTTCAGTGGCGGGGATCAGGCACAC AGTTTTCTCTGAAGATCAACAGCCTGCAGC CTGCAGATTTTGGGAGTTATTACTGTCAAC ATCATTATAATATTCCATTCACGTTCGGCT CGGGGACAAAGTTGGAAATAAAA |
| 71 | AGX-A09 Variable light (VL) chain-codon optimized nucleic acid | GACATACAAATGACACAAAGTCCCGCTAG TCTTTCAGCCAGTGTTGGTGAGACTGTGAC AATAACCTGTAGAGCTAGCAAAAATGTCT ACTCCTATCTGGCTTGGTTCCAGCAGAAAC AAGGAAAGAGTCCTCAGTTGCTCGTATATA ATGCTAAAACTTTGGCAGAAGGCGTCCCTT CTCGTTTCAGTGGCGGAGGAAGTGGGACT CAATTCTCACTGAAGATCAATAGCCTCCAG CCCGCCGACTTTGGGAGCTACTATTGCCAA CATCATTACAACATACCATTCACCTTTGGC TCAGGTACTAAACTCGAAATTAAA |
| 72 | VL-CDR1 | RASKNVYSYLA |
| 73 | VL-CDR2 | NAKTLAE |
| 74 | VL-CDR3 | QHHYNIPFT |
| | Antibody AGX-A11 | |
| 75 | AGX-A11 Variable heavy (VH) chain-amino acid | QIQLVQSGPELKKPGETVKISCKASGFTFTNY PMHWVKQAPGKGLKWMGWINTYSGVPTY ADDFKGRFAFSLETSASTAYLQINNLKNEDM ATYFCARGGYDGSREFAYWGQGTLVTVS |
| 76 | AGX-A11 Variable heavy (VH) chain-nucleic acid | CAGATCCAGTTGGTGCAGTCTGGACCTGAG CTGAAGAAGCCTGGAGAGACAGTCAAGAT CTCCTGCAAGGCTTCTGGGTTTACCTTCAC AAACTATCCAATGCACTGGGTGAAGCAGG CTCCAGGAAAGGGTTTAAAGTGGATGGGC TGGATAAACACCTACTCTGGAGTGCCAAC ATATGCAGATGACTTCAAGGGACGGTTTGC CTTCTCTTTGGAAACCTCTGCCAGCACTGC ATATTTGCAGATCAACAACCTCAAAAATG |

TABLE 2-continued

SEQUENCE DESCRIPTION

| SEQ ID NO | Description | Sequence |
|---|---|---|
| | | AGGACATGGCTACATATTTCTGTGCAAGAG GGGGCTACGATGGTAGCAGGGAGTTTGCT TACTGGGGCCAAGGGACTCTGGTCACTGTC TCT |
| 77 | AGX-A11 Variable heavy (VH) chain-codon optimized nucleic acid | CAGATACAACTCGTCCAGTCAGGTCCAGA GTTGAAGAAACCCGGAGAAACTGTGAAGA TATCCTGTAAAGCCAGCGGCTTTACTTTCA CAAACTACCCCATGCATTGGGTGAAGCAG GCCCCCGGAAAAGGACTCAAATGGATGGG ATGGATCAACACATACAGTGGGGTGCCTA CTTACGCAGACGATTTCAAAGGAAGGTTC GCATTTAGCTTGGAAACTAGCGCATCTACA GCATATCTCCAGATTAACAATCTTAAAAAT GAGGATATGGCAACATACTTCTGCGCTAG GGGAGGTTACGATGGGAGCAGGGAGTTCG CTTATTGGGGCAAGGGACTCTTGTGACTG TAAGT |
| 78 | VH-CDR1 | GFTFTNYPMH |
| 79 | VH-CDR2 | WINTYSGVPTYADDFKG |
| 80 | VH-CDR3 | GGYDGSREFAY |
| 81 | AGX-A11 Variable light (VL) chain-amino acid | DIVLTQSPASLAASLGQRATTSYRASKSVSTS GYSYMHWNQQKPGQPPRLLIYLVSNLESGV PARFSGSGSGTDFTLNIHPVEEEDAATYYCQ HIRELTTFGGGTKLEIK |
| 82 | AGX-A11 Variable light (VL) chain-nucleic acid | GACATTGTGCTGACACAGTCTCCTGCTTCC TTAGCTGCATCTCTGGGGCAGAGGGCCACC ACCTCATACAGGGCCAGCAAAAGTGTCAG TACATCTGGCTATAGTTATATGCACTGGAA CCAACAGAAACCAGGACAGCCACCCAGAC TCCTCATCTATCTTGTATCCAACCTAGAAT CTGGGGTCCCTGCCAGGTTCAGTGGCAGTG GGTCTGGGACAGACTTCACCCTCAACATCC ATCCTGTGGAGGAGGAGGATGCTGCAACC TATTACTGTCAGCACATTAGGGAGCTTACC ACGTTCGGAGGGGGGACCAAGCTGGAAAT AAAA |
| 83 | AGX-A11 Variable light (VL) chain-codon optimized nucleic acid | GACATAGTGCTCACTCAGAGCCCTGCATCC CTTGCCGCCTCCCTCGGACAACAGCTACT ACAAGCTACCGGGCATCAAAGTCCGTTAG CACATCAGGATACAGCTATATGCACTGGAA ATCAGCAAAAGCCAGGCCAACCACCCCGT CTTCTCATCTACCTCGTAAGTAATCTGGAA TCAGGCGTGCCAGCCCGATTCAGTGGGTCA GGGTCTGGGACAGATTTCACCCTCAACATC CATCCAGTAGAGGAAGAGGACGCAGCAAC ATATTACTGCCAACACATTAGAGAACTTAC CACTTTCGGAGGAGGAACTAAATTGGAGA TCAAA |
| 84 | VL-CDR1 | RASKSVSTSGYSYMH |
| 85 | VL-CDR2 | LVSNLES |
| 86 | VL-CDR3 | QHIRELTT |
| | Constant Region Sequences | |
| 87 | IgG1 G1m17* (heavy chain constant region) *with L234A/L235A/G237A mutations SEQ ID NO: 88 is sequence without the terminal lysine | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPEAAGAPSVFL FPPKPKDTLMISRTPEVTCVVVDVSHEDPEV KFNWYVDGVEVHNAKTKPREEQYNSTYRV VSVLTVLHQDWLNGKEYKCKVSNKALPAPI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |

TABLE 2-continued

SEQUENCE DESCRIPTION

| SEQ ID NO | Description | Sequence |
|---|---|---|
| 88 | IgG1 G1m17* (heavy chain constant region) *with L234A/L235A/G237A mutations | ASTKGPSVFPLAPSSKSTSGGTAALGCLVKD YFPEPVTVSWNSGALTSGVHTFPAVLQSSGL YSLSSVVTVPSSSLGTQTYICNVNHKPSNTKV DKKVEPKSCDKTHTCPPCPAPEAAGAPSVFL FPPKPKDTLMISRTPEVTCVVVDVSHEDPEV KFNWYVDGVEVHNAKTKPREEQYNSTYRV VSVLTVLHQDWLNGKEYKCKVSNKALPAPI EKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPG |
| 89 | IgG1 Km3 (light chain constant region) | RTVAAPSVFIFPPSDEQLKSGTASVVCLLNNF YPREAKVQWKVDNALQSGNSQESVTEQDSK DSTYSLSSTLTLSKADYEKHKVYACEVTHQG LSSPVTKSFNRGEC |

Humanized AGX-A07 sequences

| SEQ ID NO | Description | Sequence |
|---|---|---|
| 90 | AGX-A07 (humanized) H2 Heavy chain amino acid | QVQLVQSGAEVKKPGASVKVSCKASGYTFT NYGVKWVRQAPGQDLEWMGWINTYTGNPI YAADFKGRVTMTTDTSTSTAFMELSRLRSD DTAVYYCVRFQYGDYRYFDVWGQGTLVTV SSASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPEAAGAPSVF LFPPKPKDTLMISRTPEVTCVVVDVSHEDPE VKFNWYVDGVEVHNAKTKPREEQYNSTYR VVSVLTVLHQDWLNGKEYKCKVSNKALPAP IEKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 91 | AGX-A07 (humanized) H2 Heavy chain nucleic acid | TCTACCGGACAGGTGCAGTTGGTTCAGTCT GGCGCCGAAGTGAAGAAACCTGGCGCTTC TGTGAAGGTGTCCTGCAAGGCCTCTGGCTA CACCTTTACCAACTACGGCGTGAAATGGGT CCGACAGGCTCCTGGACAGGATCTGGAAT GGATGGGCTGGATCAACACCTACACCGGC AATCCTATCTACGCCGCCGACTTCAAGGGC AGAGTGACCATGACCACCGACACCTCTAC CTCCACCGCCTTCATGGAACTGCGGTCCCT GAGATCTGACGACACCGCCGTGTACTACTG CGTGCGGTTTCAGTACGGCGACTACCGGTA CTTTGATGTGTGGGGCCAGGGCACACTGGT CACCGTTTCTTCCGCTTCTACCAAGGGACC CAGCGTGTTCCCTCTGGCTCCTTCCTCTAA ATCCACCTCTGGCGGAACCGCTGCTCTGGG CTGTCTGGTCAAGGATTACTTCCCTGAGCC TGTGACCGTGTCCTGGAACTCTGGTGCTCT GACATCCGGCGTGCACACCTTTCCAGCTGT GCTGCAGTCCTCTGGCCTGTACTCTCTGTC CTCTGTCGTGACCGTGCCTTCTAGCTCTCT GGGCACCCAGACCTACATCTGCAACGTGA ACCACAAGCCTTCCAACACCAAGGTGGAC AAGAAGGTGGAACCCAAGTCCTGCGACAA GACCCACACCTGTCCTCCATGTCCTGCTCC AGAAGCTGCTGGCGCTCCCTCTGTGTTCCT GTTTCCTCCAAAGCCTAAGGACACCCTGAT GATCTCTCGGACCCCTGAAGTGACCTGCGT GGTGGTGGATGTGTCTCACGAGGACCCAG AAGTGAAGTTCAATTGGTACGTGGACGGC GTGGAAGTGCACAACGCCAAGACCAAGCC TAGAGAGGAACAGTACAACTCCACCTACA GAGTGGTGTCCGTGCTGACCGTGCTGCACC AGGATTGGCTGAACGGCAAAGAGTACAAG TGCAAGGTGTCCAACAAGGCACTGCCCGC TCCTATCGAAAAGACCATCTCCAAGGCTAA GGGCCAGCCTCGGGAACCTCAGGTTTACA CCCTGCCTCCATCTCGGGAAGAGATGACCA AGAACCAGGTGTCCCTGACCTGCCTCGTGA AGGGCTTCTACCCTTCCGATATCGCCGTGG |

TABLE 2-continued

SEQUENCE DESCRIPTION

| SEQ ID NO | Description | Sequence |
|---|---|---|
|  |  | AATGGGAGTCCAATGGCCAGCCTGAGAAC AACTACAAGACAACCCCTCCTGTGCTGGAC TCCGACGGCTCATTCTTCCTGTACTCCAAG CTGACAGTGGACAAGTCTCGGTGGCAGCA GGGCAACGTGTTCTCCTGTTCTGTGATGCA CGAGGCCCTGCACAACCACTACACACAGA AGTCCCTGTCTCTGTCCCCTGGCAAGTGA |
| 92 | AGX-A07 H2v1 Heavy chain amino acid | EVQLVQSGAEVKKPGASVKVSCKASGYTFT NYGVKWVRQAPGQGLEWMGWINTYTGNPI YAADFKGRVTMTTDTSTSTAYMELRSLRSD DTAVYYCVRFQYGDYRYFDVWGQGTLVTV SSASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPEAAGAPSVF LFPPKPKDTLMISRTPEVTCVVVDVSHEDPE VKFNWYVDGVEVHNAKTKPREEQYNSTYR VVSVLTVLHQDWLNGKEYKCKVSNKALPAP IEKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 93 | AGX-A07 H2v1 Heavy chain nucleic acid | GAAGTGCAGTTGGTGCAGTCTGGCGCCGA AGTGAAGAAACCTGGCGCTTCTGTGAAGG TGTCCTGCAAGGCCTCTGGCTACACCTTTA CCAACTACGGCGTGAAATGGGTCCGACAG GCTCCTGGACAAGGCCTGGAATGGATGGG CTGGATCAACACCTACACCGGCAATCCTAT CTACGCCGCCGACTTCAAGGGCAGAGTGA CCATGACCACCGACACCTCTACCTCCACCG CCTACATGGAACTGCGGTCCCTGAGATCTG ACGACACCGCCGTGTACTACTGCGTGCGGT TTCAGTACGGCGACTACCGGTACTTTGATG TGTGGGGCCAGGGCACACTGGTCACCGTTT CTTCCGCTTCTACCAAGGGACCCAGCGTGT TCCCTCTGGCTCCTTCCTCTAAATCCACCTC TGGCGGAACCGCTGCTCTGGGCTGTCTGGT CAAGGATTACTTCCCTGAGCCTGTGACCGT GTCCTGGAATTCTGGTGCTCTGACATCCGG CGTGCACACCTTTCCAGCTGTGCTGCAGTC CTCTGGCCTGTACTCTCTGTCCTCTGTCGTG ACCGTGCCTTCTAGCTCTCTGGGCACCCAG ACCTACATCTGCAACGTGAACCACAAGCCT TCCAACACCAAGGTGGACAAGAAGGTGGA ACCCAAGTCCTGCGACAAGACCCACACCT GTCCTCCATGTCCTGCTCCAGAAGCTGCTG GCGCTCCCTCTGTGTTCCTGTTTCCTCCAAA GCCTAAGGACACCCTGATGATCTCTCGGAC CCCTGAAGTGACCTGCGTGGTGGTGGATGT GTCTCACGAGGACCCAGAAGTGAAGTTCA ATTGGTACGTGGACGGCGTGGAAGTGCAC AACGCCAAGACCAAGCCTAGAGAGGAACA GTACAACTCCACCTACAGAGTGGTGTCCGT GCTGACCGTGCTGCACCAGGATTGGCTGA ACGGCAAAGAGTACAAGTGCAAGGTGTCC AACAAGGCACTGCCCGCTCCTATCGAAAA GACCATCTCCAAGGCTAAGGGCCAGCCTC GGGAACCTCAGGTTTACACCCTGCCTCCAT CTCGGGAAGAGATGACCAAGAACCAGGTG TCCCTGACCTGCCTCGTGAAGGGCTTCTAC CCTTCCGATATCGCCGTGGAATGGGAGTCC AATGGCCAGCCTGAGAACAACTACAAGAC AACCCCTCCTGTGCTGGACTCCGACGGCTC ATTCTTCCTGTACTCCAAGCTGACAGTGGA CAAGTCTCGGTGGCAGCAGGGCAACGTGT TCTCCTGTTCTGTGATGCACGAGGCCCTGC ACAACCACTACACACAGAAGTCCCTGTCTC TGTCCCCTGGCAAGTGA |
| 94 | VH-CDR1 | GYTFTNYGVK |
| 95 | VH-CDR2 | WINTYTGNPIYAADFK |

TABLE 2-continued

SEQUENCE DESCRIPTION

| SEQ ID NO | Description | Sequence |
|---|---|---|
| 96 | VH-CDR3 | FQYGDYRYFDV |
| 97 | AGX-A07 L5<br>Light chain amino acid | EIILTQSPATLSLSPGERATLSCRANSGISFI<br>NWYQQKPGQAPRLLIYGTANLASGIPARFGGS<br>GSGRDFTLTISSLEPEDFAVYYCQQWSSNPLT<br>FGGGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKHK<br>VYACEVTHQGLSSPVTKSFNRGEC |
| 98 | AGX-A07 L5<br>Light chain nucleic acid | AAGCTTGCCACCATGGAAACCGACACACT<br>GCTGCTGTGGGTGCTGTTGTTGTGGGGTGCC<br>AGGATCTACCGGAGAGATCATCCTGACAC<br>AGAGCCCCGCCACATTGTCTCTGAGTCCTG<br>GCGAGAGAGCTACCCTGTCCTGTAGAGCC<br>AACTCCGGCATCTCCTTCATCAACTGGTAT<br>CAGCAGAAGCCCGGCCAGGCTCCTAGACT<br>GCTGATCTATGGCACCGCTAACCTGGCCTC<br>TGGCATCCCTGCTAGATTTGGCGGCTCTGG<br>CTCTGGCAGAGACTTCACCCTGACCATCTC<br>TAGCCTGGAACCTGAGGACTTCGCCGTGTA<br>CTACTGCCAGCAGTGGTCTAGCAACCCTCT<br>GACCTTTGGCGGAGGCACCAAGGTGGAAA<br>TCAAGAGAACCGTGGCCGCTCCTTCCGTGT<br>TCATCTTCCCACCATCTGACGAGCAGCTGA<br>AGTCTGGCACAGCCTCTGTCGTGTGCCTGC<br>TGAACAACTTCTACCCTCGGGAAGCCAAG<br>GTGCAGTGGAAGGTGGACAATGCCCTGCA<br>GTCCGGCAACTCCCAAGAGTCTGTGACCG<br>AGCAGGACTCCAAGGACTCTACCTACAGC<br>CTGTCCTCCACACTGACCCTGTCTAAGGCC<br>GACTACGAGAAGCACAAGGTGTACGCCTG<br>TGAAGTGACCCACCAGGGACTGTCTAGCC<br>CCGTGACCAAGTCTTTCAACCGGGGCGAGT<br>GCTGA |
| 99 | AGX-A07 L5v1<br>Light chain amino acid | EIVLTQSPATLSLSPGERATLSCRANSGISFI<br>NWYQQKPGQAPRLLIYGTANLASGIPARFSGS<br>GSGRDFTLTISSLEPEDFAVYYCQQWSSNPLT<br>FGGGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKHK<br>VYACEVTHQGLSSPVTKSFNRGEC |
| 100 | AGX-A07 L5v1<br>Light chain nucleic acid | TCTACAGGCGAGATCGTGCTGACCCAGTCT<br>CCTGCCACATTGTCTCTGAGTCCTGGCGAG<br>AGAGCTACCCTGTCCTGTAGAGCCAACTCC<br>GGCATCTCCTTCATCAACTGGTATCAGCAG<br>AAGCCCGGCCAGGCTCCTAGACTGCTGATC<br>TATGGCACCGCTAACCTGGCCTCTGGCATC<br>CCTGCTAGATTTTCCGGCTCTGGCTCTGGC<br>AGAGACTTCACCCTGACCATCTCTAGCCTG<br>GAACCTGAGGACTTCGCCGTGTACTACTGC<br>CAGCAGTGGTCTAGCAACCCTCTGACCTTT<br>GGCGGAGGCACCAAGGTGGAAATCAAGAG<br>AACCGTGGCCGCTCCTTCCGTGTTCATCTT<br>CCCACCATCTGACGAGCAGCTGAAGTCTG<br>GCACAGCCTCTGTCGTGTGCCTGCTGAACA<br>ACTTCTACCCTCGGGAAGCCAAGGTGCAGT<br>GGAAGGTGGACAATGCCCTGCAGTCCGGC<br>AACTCCCAAGAGTCTGTGACCGAGCAGGA<br>CTCCAAGGACTCTACCTACAGCCTGTCCTC<br>CACACTGACCCTGTCTAAGGCCGACTACGA<br>GAAGCACAAGGTGTACGCCTGTGAAGTGA<br>CCCACCAGGGACTGTCTAGCCCCGTGACCA<br>AGTCTTTCAACCGGGGCGAGTGCTGA |
| 101 | AGX-A07 L5v2<br>Light chain amino acid | EIVLTQSPATLSLSPGERATLSCRAQSGISFI<br>NWYQQKPGQAPRLLIYGTANLASGIPARFSGS<br>GSGRDFTLTISSLEPEDFAVYYCQQWSSNPLT<br>FGGGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKHK<br>VYACEVTHQGLSSPVTKSFNRGEC |

TABLE 2-continued

SEQUENCE DESCRIPTION

| SEQ ID NO | Description | Sequence |
|---|---|---|
| 102 | AGX-A07 L5v2<br>Light chain nucleic acid | TCTACAGGCGAGATCGTGCTGACCCAGTCT<br>CCTGCCACATTGTCTCTGAGTCCTGGCGAG<br>AGAGCTACCCTGTCTTGTAGAGCCCAGTCC<br>GGCATCTCCTTCATCAACTGGTATCAGCAG<br>AAGCCCGGCCAGGCTCCTAGACTGCTGATC<br>TATGGCACCGCTAACCTGGCCTCTGGCATC<br>CCTGCTAGATTTTCCGGCTCTGGCTCTGGC<br>AGAGACTTCACCCTGACCATCTCTAGCCTG<br>GAACCTGAGGACTTCGCCGTGTACTACTGC<br>CAGCAGTGGTCTAGCAACCCTCTGACCTTT<br>GGCGGAGGCACCAAGGTGGAAATCAAGAG<br>AACCGTGGCCGCTCCTTCCGTGTTCATCTT<br>CCCACCATCTGACGAGCAGCTGAAGTCTG<br>GCACAGCCTCTGTCGTGTGCCTGCTGAACA<br>ACTTCTACCCTCGGGAAGCCAAGGTGCAGT<br>GGAAGGTGGACAATGCCCTGCAGTCTGGC<br>AACTCCCAAGAGTCTGTGACCGAGCAGGA<br>CTCCAAGGACTCTACCTACAGCCTGTCCTC<br>CACACTGACCCTGTCTAAGGCCGACTACGA<br>GAAGCACAAGGTGTACGCCTGTGAAGTGA<br>CCCACCAGGGACTGTCTAGCCCCGTGACCA<br>AGTCTTTCAACCGGGGCGAGTGCTGA |
| 103 | AGX-A07 L5v3<br>Light chain amino acid | EIVLTQSPATLSLSPGERATLSCRANSGISFI<br>NWYQQKPGQAPRLLIYGTANLASGIPARFSGS<br>GSGRDFTLTISSLEPEDFAVYYCQQYSSNPLT<br>FGGGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKHK<br>VYACEVTHQGLSSPVTKSFNRGEC |
| 104 | AGX-A07 L5v3<br>Light chain nucleic acid | TCTACAGGCGAGATCGTGCTGACCCAGTCT<br>CCTGCCACATTGTCTCTGAGTCCTGGCGAG<br>AGAGCTACCCTGTCCTGTAGAGCCAACTCC<br>GGCATCTCCTTCATCAACTGGTATCAGCAG<br>AAGCCCGGCCAGGCTCCTAGACTGCTGATC<br>TATGGCACCGCTAACCTGGCCTCTGGCATC<br>CCTGCTAGATTTTCCGGCTCTGGCTCTGGC<br>AGAGACTTCACCCTGACCATCTCTAGCCTG<br>GAACCTGAGGACTTCGCCGTGTACTACTGC<br>CAGCAGTACAGCAGCAACCCTCTGACCTTT<br>GGCGGAGGCACCAAGGTGGAAATCAAGAG<br>AACCGTGGCCGCTCCTTCCGTGTTCATCTT<br>CCCACCATCTGACGAGCAGCTGAAGTCTG<br>GCACAGCCTCTGTCGTGTGCCTGCTGAACA<br>ACTTCTACCCTCGGGAAGCCAAGGTGCAGT<br>GGAAGGTGGACAATGCCCTGCAGTCCGGC<br>AACTCCCAAGAGTCTGTGACCGAGCAGGA<br>CTCCAAGGACTCTACCTACAGCCTGTCCTC<br>CACACTGACCCTGTCTAAGGCCGACTACGA<br>GAAGCACAAGGTGTACGCCTGTGAAGTGA<br>CCCACCAGGGACTGTCTAGCCCCGTGACCA<br>AGTCTTTCAACCGGGGCGAGTGCTGA |
| 105 | AGX-A07 L5v4<br>Light chain amino acid | EIVLTQSPATLSLSPGERATLSCRAQSGISFI<br>NWYQQKPGQAPRLLIYGTANLASGIPARFSGS<br>GSGRDFTLTISSLEPEDFAVYYCQQYSSNPLT<br>FGGGTKVEIKRTVAAPSVFIFPPSDEQLKSGT<br>ASVVCLLNNFYPREAKVQWKVDNALQSGNS<br>QESVTEQDSKDSTYSLSSTLTLSKADYEKHK<br>VYACEVTHQGLSSPVTKSFNRGEC |
| 106 | AGX-A07 L5v4<br>Light chain nucleic acid | TCTACAGGCGAGATCGTGCTGACCCAGTCT<br>CCTGCCACATTGTCTCTGAGTCCTGGCGAG<br>AGAGCTACCCTGTCTTGTAGAGCCCAGTCC<br>GGCATCTCCTTCATCAACTGGTATCAGCAG<br>AAGCCCGGCCAGGCTCCTAGACTGCTGATC<br>TATGGCACCGCTAACCTGGCCTCTGGCATC<br>CCTGCTAGATTTTCCGGCTCTGGCTCTGGC<br>AGAGACTTCACCCTGACCATCTCTAGCCTG<br>GAACCTGAGGACTTCGCCGTGTACTACTGC<br>CAGCAGTACAGCAGCAACCCTCTGACCTTT<br>GGCGGAGGCACCAAGGTGGAAATCAAGAG<br>AACCGTGGCCGCTCCTTCCGTGTTCATCTT<br>CCCACCATCTGACGAGCAGCTGAAGTCTG |

TABLE 2-continued

SEQUENCE DESCRIPTION

| SEQ ID NO | Description | Sequence |
|---|---|---|
| | | GCACAGCCTCTGTCGTGTGCCTGCTGAACA ACTTCTACCCTCGGGAAGCCAAGGTGCAGT GGAAGGTGGACAATGCCCTGCAGTCTGGC AACTCCCAAGAGTCTGTGACCGAGCAGGA CTCCAAGGACTCTACCTACAGCCTGTCCTC CACACTGACCCTGTCTAAGGCCGACTACGA GAAGCACAAGGTGTACGCCTGTGAAGTGA CCCACCAGGGACTGTCTAGCCCCGTGACCA AGTCTTTCAACCGGGGCGAGTGCTGA |
| 107 | VL-CDR1 (variant 1) | RANSGISFIN |
| 108 | VL-CDR1 (variant 2) | RAQSGISFIN |
| 109 | VL-CDR2 | GTANLAS |
| 110 | VL-CDR3 (variant 1) | QQWSSNPLT |
| 111 | VL-CDR3 (variant 2) | QQYSSNPLT |
| | Humanized AGX-A01 sequences | |
| 112 | AGX-A01 H1 Heavy chain amino acid | EVQLVESGGGLVKPGGSLRLSCAASGFTFSS FAMSWVRQAPGKGLEWVSTISSGSIYIYYTD GVKGRFTISRDNAKNSLYLQMNSLRAEDTA VYYCARRGIYYGYDGYAMDYWGQGTLVTV SSASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPEAAGAPSVF LFPPKPKDTLMISRTPEVTCVVVDVSHEDPE VKFNWYVDGVEVHNAKTKPREEQYNSTYR VVSVLTVLHQDWLNGKEYKCKVSNKALPAP IEKTISKAKGQPREPQVYTLPPSREEMTKNQV SLTCLVKGFYPSDIAVEWESNGQPENNYKTT PPVLDSDGSFFLYSKLTVDKSRWQQGNVFSC SVMHEALHNHYTQKSLSLSPGK |
| 113 | AGX-A01 H1 Heavy chain nucleic acid | GAGGTGCAGCTGGTTGAATCTGGCGGAGG ACTTGTGAAGCCTGGCGGCTCTCTGAGACT GTCTTGTGCCGCCTCTGGCTTCACCTTCTC AGCTTTGCCATGTCCTGGGTCCGACAGGCT CCTGGCAAAGGACTGGAATGGGTGTCCAC CATCTCCTCCGGCTCCATCTACATCTACTA CACCGACGGCGTGAAGGGCAGATTCACCA TCAGCAGAGACAACGCCAAGAACTCCCTG TACCTGCAGATGAACAGCCTGAGAGCCGA GGACACCGCCGTGTACTATTGTGCCAGACG GGGCATCTACTATGGCTACGACGGCTACGC TATGGACTATTGGGGACAGGGCACACTGG TCACCGTGTCCTCTGCTTCTACCAAGGGAC CCAGCGTGTTCCCTCTGGCTCCTTCCTCTA AATCCACCTCTGGCGGAACCGCTGCTCTGG GCTGTCTGGTCAAGGATTACTTCCCTGAGC CTGTGACCGTGTCCTGGAACTCTGGTGCTC TGACATCCGGCGTGCACACCTTTCCAGCTG TGCTGCAGTCCTCTGGCCTGTACTCTCTGT CCTCTGTCGTGACCGTGCCTTCTAGCTCTCT GGGCACCCAGACCTACATCTGCAACGTGA ACCACAAGCCTTCCAACACCAAGGTGGAC AAGAAGGTGGAACCCAAGTCCTGCGACAA GACCCACACCTGTCCTCCATGTCCTGCTCC AGAAGCTGCTGGCGCTCCCTCTGTGTTCCT GTTTCCTCCAAAGCCTAAGGACACCCTGAT GATCTCTCGGACCCCTGAAGTGACCTGCGT GGTGGTGGATGTGTCTCACGAGGACCCAG AAGTGAAGTTCAATTGGTACGTGGACGGC GTGGAAGTGCACAACGCCAAGACCAAGCC TAGAGAGGAACAGTACAACTCCACCTACA GAGTGGTGTCCGTGCTGACCGTGCTGCACC AGGATTGGCTGAACGGCAAAGAGTACAAG TGCAAGGTGTCCAACAAGGCACTGCCCGC TCCTATCGAAAAGACCATCTCCAAGGCTAA GGGCCAGCCTCGGGAACCTCAGGTTTACA CCCTGCCTCCATCTCGGGAAGAGATGACCA |

TABLE 2-continued

SEQUENCE DESCRIPTION

| SEQ ID NO | Description | Sequence |
|---|---|---|
| | | AGAACCAGGTGTCCCTGACCTGCCTCGTGA AGGGCTTCTACCCTTCCGATATCGCCGTGG AATGGGAGTCCAATGGCCAGCCTGAGAAC AACTACAAGACAACCCCTCCTGTGCTGGAC TCCGACGGCTCATTCTTCCTGTACTCCAAG CTGACAGTGGACAAGTCTCGGTGGCAGCA GGGCAACGTGTTCTCCTGTTCTGTGATGCA CGAGGCCCTGCACAACCACTACACACAGA AGTCCCTGTCTCTGTCCCCTGGCAAGTGA |
| 114 | AGX-A01 H1v1 Heavy chain amino acid | EVQLVESGGGLVKPGGSLRLSCAASGFTFSS FAMSWVRQAPGKGLEWVSTISSGSIYIYYTD SVKGRFTISRDNAKNSLYLQMNSLRAEDTAV YYCARRGIYYGYEGYAMDYWGQGTLVTVS SASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPEAAGAPSVF LFPPKPKDTLMISRTPEVTCVVVDVSHEDPE VKFNWYVDGVEVHNAKTKPREEQYNSTYR VVSVLTVLHQDWLNGKEYKCKVSNKALPAP IEKTISKAKGQPREPQVYTLPPSREEMTKNQV SLTCLVKGFYPSDIAVEWESNGQPENNYKTT PPVLDSDGSFFLYSKLTVDKSRWQQGNVESC SVMHEALHNHYTQKSLSLSPGK |
| 115 | VH-CDR1 | GFTFSSFAMS |
| 116 | VH-CDR2 (variant 1) | TISSGSIYIYYTDGVKG |
| 117 | VH-CDR2 (variant 2) | TISSGSIYIYYTDSVKG |
| 118 | VH-CDR3 (variant 1) | RGIYYGYDGYAMDY |
| 119 | VH-CDR3 (variant 2) | RGIYYGYEGYAMDY |
| 120 | VH-CDR3 (variant 3) | RGIYYGYSGYAMDY |
| 121 | VH-CDR3 (variant 4) | RGIYYGYAGYAMDY |
| 122 | AGX-A01 L10 Light chain amino acid | AIVLTQSPGTLSLSPGERATLSCRSSQSLVHS NGNTYLHWYMQKPGQAPRVLIYKVSNRFSGI PDRFSGSGSGTDFTLTISRLEPDDFAIYYCSQ STHIPLAFGQGTKLEIKRTVAAPSVFIFPPSD EQLKSGTASVVCLLNNFYPREAKVQWKVDN ALQSGNSQESVTEQDSKDSTYSLSSTLTLSKA DYEKHKVYACEVTHQGLSSPVTKSFNRGEC |
| 123 | AGX-A01 L10 Light chain nucleic acid | GCCATCGTGTTGACCCAGTCTCCAGGCACA TTGTCTCTGAGCCCTGGCGAGAGAGCTACC CTGTCCTGCAGATCTTCTCAGTCCCTGGTG CACTCCAACGGCAACACCTACCTGCACTGG TACATGCAGAAGCCCGGACAGGCTCCCAG AGTGCTGATCTACAAGGTGTCCAACCGGTT CTCTGGCATCCCCGACAGATTTTCCGGCTC TGGCTCTGGCACCGACTTCACCCTGACCAT CTCTAGACTGGAACCCGACGACTTCGCCAT CTACTACTGCTCCCAGTCCACACACATCCC TCTGGCTTTTGGCCAGGGCACCAAGCTGGA AATCAAGAGAACCGTGGCCGCTCCTTCCGT GTTCATCTTCCCACCATCTGACGAGCAGCT GAAGTCCGGCACAGCTTCTGTCGTGTGCCT GCTGAACAACTTCTACCCTCGGGAAGCCA AGGTGCAGTGGAAGGTGGACAATGCCCTG CAGTCCGGCAACTCCCAAGAGTCTGTGACC GAGCAGGACTCCAAGGACTCTACCTACAG CCTGTCCTCCACACTGACCCTGTCTAAGGC CGACTACGAGAAGCACAAGGTGTACGCCT GTGAAGTGACCCACCAGGGCCTGTCTAGC CCTGTGACCAAGTCTTTCAACCGGGGCGAG TGTTGA |
| 124 | VL-CDR1 (variant 1) | RSSQSLVHSNGNTYLH |
| 125 | VL-CDR1 (variant 2) | RSSQSLVHSSGNTYLH |

TABLE 2-continued

SEQUENCE DESCRIPTION

| SEQ ID NO | Description | Sequence |
|---|---|---|
| 126 | VL-CDR1 (variant 3) | RSSQSLVHSTGNTYLH |
| 127 | VL-CDR1 (variant 4) | RSSQSLVHSQGNTYLH |
| 128 | VL-CDR2 | KVSNRFS |
| 129 | VL-CDR3 | SQSTHIPLA |
| | Humanized AGX-A07 H2v1L5v2 | |
| 130 | AGX-A07 H2v1<br>Heavy chain variable region<br>amino acid | EVQLVQSGAEVKKPGASVKVSCKASGYTFT<br>NYGVKWVRQAPGQGLEWMGWINTYTGNPI<br>YAADFKGRVTMTTDTSTSTAYMELRSLRSD<br>DTAVYYCVRFQYGDYRYFDVWGQGTLVTV<br>SS |
| 131 | AGX-A07 H2v1L5v2<br>Light chain variable region<br>amino acid | EIVLTQSPATLSLSPGERATLSCRAQSGISFI<br>NWYQQKPGQAPRLLIYGTANLASGIPARFSGS<br>GSGRDFTLTISSLEPEDFAVYYCQQWSSNPLT<br>FGGGTKVEIK |
| | Humanized AGX-A07 H2L5 | |
| 132 | AGX-A07 H2<br>Heavy chain variable region<br>amino acid | QVQLVQSGAEVKKPGASVKVSCKAS<u>GYTFT</u><br><u>NYGVK</u>WVRQAPGQDLEWMG<u>WINTYTGNPI</u><br><u>YAADFK</u>GRVTMTTDTSTSTAFMELRSLRSD<br>DTAVYYCVR<u>FQYGDYRYFDV</u>WGQGTLVTV<br>SS |
| 133 | AGX-A07 L5<br>Light chain variable region<br>amino acid | EIILTQSPATLSLSPGERATLSC<u>RANSGISFI</u><br><u>N</u>WYQQKPGQAPRLLIY<u>GTANLAS</u>GIPARFGGS<br>GSGRDFTLTISSLEPEDFAVYYC<u>QQWSSNPLT</u><br>FGGGTKVEIK |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An anti-TM4SF1 binding protein comprising:
   a heavy chain variable domain comprising a CDR3 domain comprising the amino acid sequence of SEQ ID NO: 96; a CDR2 domain comprising the amino acid sequence of SEQ ID NO: 95; and a CDR1 domain comprising the amino acid sequence of SEQ ID NO: 94; and
   a light chain variable domain comprising a CDR3 domain comprising the amino acid sequence of SEQ ID NO: 110 or 111; a CDR2 domain comprising the amino acid sequence of SEQ ID NO: 109; and a CDR1 comprising the amino acid sequence of SEQ ID NO: 107 or 108.

2. The anti-TM4SF1 binding protein of claim 1, comprising
   a heavy chain comprising an amino acid sequence that has at least 95% identity to a sequence selected from the group consisting of: SEQ ID NOs: 90, 92, 130, and 132; and
   a light chain comprising an amino acid sequence that has at least 95% identity to a sequence selected from the group consisting of: SEQ ID NO: 97, 99, 101, 103, 105, 131, and 133.

3. An anti-TM4SF1 binding protein comprising a heavy chain comprising an amino acid sequence selected from the group consisting of: SEQ ID NOs: 90, 92, 130 and 132; and a light chain comprising an amino acid sequence selected from the group consisting of: SEQ ID NOs: 97, 99, 101, 103, 105, 131, and 133.

4. The anti-TM4SF1 binding protein of claim 1, wherein the binding protein comprises an Fc region comprising a mutation at position N297.

5. The anti-TM4SF1 binding protein of claim 1, comprising an antigen-binding fragment of an anti-TM4SF1 antibody, wherein the antigen-binding fragment comprises a Fab, a Fab', a F(ab')2, an Fv, or an scFv.

6. The anti-TM4SF1 binding protein of claim 1, wherein the binding of the protein to human TM4SF1 is not dependent on glycosylation of the ECL2 loop of human TM4SF1, wherein the human TM4SF1 comprises a sequence as set forth in SEQ ID NO: 134.

7. The anti-TM4SF1 binding protein of claim 1, wherein the protein binds to a cynomolgus TM4SF1 with a KD about $1 \times 10^{-8}$ M or less in a standard flow cytometry assay using HEK293 overexpressing cells.

8. The anti-TM4SF1 binding protein of claim 1, wherein the protein binds to human TM4SF1 with a KD of about $1 \times 10^{-9}$ M or less in a standard flow cytometry assay using HUVEC cells.

9. A antibody drug conjugate comprising:
i) an antigen binding protein comprising the anti-TM4SF1 binding protein of claim 1; and
ii) a therapeutic molecule.

10. The antibody drug conjugate of claim 9, wherein the therapeutic molecule is selected from a group consisting of a cytotoxic agent, a chemotherapeutic agent, a protein, a peptide, an antibody, a growth inhibitory agent, an anti-hormonal agent, or a combination thereof.

11. The anti-TM4SF1 binding protein of claim 1, wherein the heavy chain variable domain comprises the CDR3 domain comprising the amino acid sequence of SEQ ID NO: 96, the CDR2 domain comprising the amino acid sequence of SEQ ID NO: 95, and the CDR1 domain comprising the amino acid sequence of SEQ ID NO: 94; and
wherein the light chain variable domain comprises the CDR3 domain comprising the amino acid sequence of SEQ ID NO: 110, the CDR2 domain comprising the amino acid sequence of SEQ ID NO: 109, and the CDR1 domain comprising the amino acid sequence of SEQ ID NO: 108.

12. The anti-TM4SF1 binding protein of claim 1, wherein the heavy chain variable domain comprises the CDR3 domain comprising the amino acid sequence of SEQ ID NO: 96, the CDR2 domain comprising the amino acid sequence of SEQ ID NO: 95, and the CDR1 domain comprising the amino acid sequence of SEQ ID NO: 94; and
wherein the light chain variable domain comprises the CDR3 domain comprising the amino acid sequence of SEQ ID NO: 110, the CDR2 domain comprising the amino acid sequence of SEQ ID NO: 109, and the CDR1 domain comprising the amino acid sequence of SEQ ID NO: 107.

13. The anti-TM4SF1 binding protein of claim 1, wherein the heavy chain variable domain comprises the CDR3 domain comprising the amino acid sequence of SEQ ID NO: 96, the CDR2 domain comprising the amino acid sequence of SEQ ID NO: 95, and the CDR1 domain comprising the amino acid sequence of SEQ ID NO: 94; and
wherein the light chain variable domain comprises the CDR3 domain comprising the amino acid sequence of SEQ ID NO: 111, the CDR2 domain comprising the amino acid sequence of SEQ ID NO: 109, and the CDR1 domain comprising the amino acid sequence of SEQ ID NO: 107.

14. The anti-TM4SF1 binding protein of claim 1, wherein the heavy chain variable domain comprises the CDR3 domain comprising the amino acid sequence of SEQ ID NO: 96, the CDR2 domain comprising the amino acid sequence of SEQ ID NO: 95, and the CDR1 domain comprising the amino acid sequence of SEQ ID NO: 94; and
wherein the light chain variable domain comprises the CDR3 domain comprising the amino acid sequence of SEQ ID NO: 111, the CDR2 domain comprising the amino acid sequence of SEQ ID NO: 109, and the CDR1 domain comprising the amino acid sequence of SEQ ID NO: 108.

15. The antibody drug conjugate of claim 9, wherein the therapeutic molecule is maytansine.

\* \* \* \* \*

SEQUENCE LISTING

```
<160> NUMBER OF SEQ ID NOS: 135

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Val Arg Gln Thr Pro Glu Lys Arg Leu Glu Trp Val
        35                  40                  45

Ala Thr Ile Ser Ser Gly Ser Ile Tyr Ile Tyr Tyr Thr Asp Gly Val
    50                  55                  60

Lys Gly Arg Phe Thr Ile Ser Arg Asp Asn Ala Lys Asn Thr Val His
```

```
                65                  70                  75                  80
Leu Gln Met Ser Ser Leu Arg Ser Glu Asp Thr Ala Met Tyr Tyr Cys
                    85                  90                  95

Ala Arg Arg Gly Ile Tyr Tyr Gly Tyr Asp Gly Tyr Ala Met Asp Tyr
                100                 105                 110

Trp Gly Gln Gly Thr Ser Val Thr Val Ser
            115                 120

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Met Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Ile Tyr Phe Cys Ser Gln Ser
                85                  90                  95

Thr His Ile Pro Leu Ala Phe Gly Ala Gly Thr Lys Leu Glu Leu Lys
            100                 105                 110

<210> SEQ ID NO 3
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Arg Asp Tyr
            20                  25                  30

Gly Met Asn Trp Val Lys Gln Ala Pro Gly Arg Thr Phe Lys Trp Met
        35                  40                  45

Gly Trp Ile Asn Thr Tyr Thr Gly Ala Pro Tyr Ala Ala Asp Phe
    50                  55                  60

Lys Gly Arg Phe Ala Phe Ser Leu Asp Thr Ser Ala Ser Ala Ala Phe
65                  70                  75                  80

Leu Gln Ile Asn Asn Leu Lys Asn Glu Asp Thr Ala Thr Tyr Phe Cys
                85                  90                  95

Ala Arg Trp Val Ser Tyr Gly Asn Asn Arg Asn Trp Phe Phe Asp Phe
            100                 105                 110

Trp Gly Ala Gly Thr Thr Val Thr Val Ser Ser
            115                 120
```

<210> SEQ ID NO 4
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
cagatccagt tggtgcagtc tggacctgag ctgaagaagc tggagagac agtcaagatc      60
tcctgcaagg cttctgggta ttccttcaga gactatggaa tgaactgggt gaagcaggct     120
ccaggaagga cttttaagtg gatgggctgg ataaacacct acactggagc gccagtatat    180
gctgctgact tcaagggacg gtttgccttc tctttggaca cctctgccag cgctgccttt    240
ttgcagatca acaacctcaa aaatgaagac acggctacat atttctgtgc aagatgggtc    300
tcctacggta ataaccgcaa ctggttcttc gattttggg gcgcagggac cacggtcacc    360
gtctcctca                                                            369
```

<210> SEQ ID NO 5
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
caaattcagt tggttcaatc cggccctgag ctcaagaagc tggagagac agtgaagata      60
agttgtaagg ctagtggcta ttcatttcga gattatggga tgaattgggt caagcaggcc    120
ccagggcgga ccttcaaatg gatggggtgg atcaatactt acactggcgc accagtatat    180
gcagctgatt ttaagggtcg ctttgcattt tcacttgata cttcagccag tgccgctttt    240
ttgcaaatca acaatctcaa aaatgaagac actgctacat atttctgcgc aggtgggtg    300
agctatggca ataacagaaa ttggttcttt gacttttggg gcgcaggcac caccgtcact    360
gtctcatca                                                            369
```

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly Tyr Ser Phe Arg Asp Tyr Gly Met Asn
1               5                   10
```

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Trp Ile Asn Thr Tyr Thr Gly Ala Pro Val Tyr Ala Ala Asp Phe Lys
1               5                   10                  15
Gly
```

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Ser Tyr Gly Asn Asn Arg Asn Trp Phe Phe Asp Phe
1               5                   10

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Leu Met Thr Gln Thr Pro Leu Ser Leu Pro Val Arg Leu Gly
1               5                   10                  15

Asp Gln Ala Ser Ile Ser Cys Arg Ser Ser Gln Thr Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Phe Gln Gly
                85                  90                  95

Ser His Gly Pro Trp Thr Phe Gly Gly Gly Thr Lys Leu Glu Ile Lys
            100                 105                 110

<210> SEQ ID NO 10
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gatgttttga tgacccaaac tccactctcc ctgcctgtcc gtcttggaga tcaggcctcc      60
atctcttgta gatctagtca gacccttgta catagtaatg gaaacaccta tttagaatgg    120
tacctgcaga aaccaggcca gtctccaaaa ctcttgatct acaaagtttc caatcgactt    180
tctggggtcc cagacaggtt cagtggcagt ggatcaggga cagatttcac actcaagatc    240
agcagagtgg agactgagga tctgggagtt tattactgct ttcaaggttc acatggtccg    300
tggacgttcg gtggaggcac caagctggaa atcaaa                              336

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gacgtactta tgacacaaac tcccttgagc ttgccagtac ggcttggcga tcaagcttca      60
atttcatgtc gttcttctca aacacttgtc cactcaaatg gaatacata  tttggaatgg     120 tatctccaaa agcccggcca atccccaaaa ttgttgattt acaaggtgtc taatcgactc     180
tcaggcgtcc ccgaccgatt ctccgggagc gggtccggta cagacttcac cttgaaaatc     240
tccagggtag aaactgaaga cctcggagtc tactattgtt tccagggatc acacggcccc     300
tggacatttg gaggaggaac taagctcgag atcaaa                               336
```

<210> SEQ ID NO 12  
<211> LENGTH: 16  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 12

```
Arg Ser Ser Gln Thr Leu Val His Ser Asn Gly Asn Thr Tyr Leu Glu
1               5                   10                  15
```

<210> SEQ ID NO 13  
<211> LENGTH: 7  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 13

```
Lys Val Ser Asn Arg Leu Ser
1               5
```

<210> SEQ ID NO 14  
<211> LENGTH: 9  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 14

```
Phe Gln Gly Ser His Gly Pro Trp Thr
1               5
```

<210> SEQ ID NO 15  
<211> LENGTH: 118  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 15

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Asp Tyr
                20                  25                  30

Thr Met His Trp Val Arg Gln Ser His Gly Lys Ser Leu Glu Trp Ile
            35                  40                  45

Gly Ser Phe Asn Pro Asn Asn Gly Gly Leu Thr Asn Tyr Asn Gln Lys
        50                  55                  60

Phe Lys Gly Lys Ala Thr Leu Thr Val Asp Lys Ser Ser Ser Thr Val
```

```
                 65                  70                  75                  80
Tyr Met Asp Leu Arg Ser Leu Thr Ser Glu Asp Ser Ala Val Tyr Tyr
                85                  90                  95

Cys Thr Arg Ile Arg Ala Thr Gly Phe Asp Ser Trp Gly Gln Gly Thr
            100                 105                 110

Thr Leu Thr Val Ser Ser
        115
```

<210> SEQ ID NO 16
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gaggtccagc tgcaacagtc tggacctgag ctggtgaagc ctggggcttc agtgaagata      60
tcctgcaaga cttctggata cacattcact gattacacca tgcactgggt gaggcagagc     120
catggaaaga gccttgagtg gattggaagt tttaatccta acaatggtgg tcttactaac     180
tacaaccaga agttcaaggg caaggccaca ttgactgtgg acaagtcttc agcacagtg      240 tacatggacc tccgcagcct gacatctgag gattctgcag tctattactg tacaagaatc     300
cgggctacgg gctttgactc ctggggccag ggcaccactc tcacagtctc ctca           354
```

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gaggtacaac tgcaacagag tggacctgaa cttgtcaaac ctggagcaag tgtgaagatt      60
agctgtaaaa ccagtggcta cacatttacc gattatacta tgcactgggt aagacagagc     120
cacggaaaat cacttgagtg gattggtagt ttcaatccta caacggagg attgacaaat      180 tacaaccaga agttcaaagg gaaagccacc ttgacagttg ataagtcctc aagtaccgtg     240
tatatggatc tgcgttctct cacaagtgaa gatagcgcag tttactactg tacccgcatc     300
cgagccaccg ggttcgattc atggggtcag gggacaacac tgactgtttc ttct           354
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gly Tyr Thr Phe Thr Asp Tyr Thr Met His
1               5                   10
```

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Phe Asn Pro Asn Asn Gly Gly Leu Thr Asn Tyr Asn Gln Lys Phe
1               5                   10                  15

Lys Gly

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Arg Ala Thr Gly Phe Asp Ser
1               5

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Val Gln Ala Glu Asp Leu Thr Val Tyr Tyr Cys Lys Gln
                85                  90                  95

Ser Tyr Asn Pro Pro Trp Thr Phe Gly Gly Gly Thr Lys Leu Glu Ile
            100                 105                 110

Lys

<210> SEQ ID NO 22
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gacattgtga tgtcacagtc tccatcctcc ctggctgtgt cagcaggaga gaaggtcact      60
atgagctgca atccagtca gagtctgctc aacagtagaa cccgaaagaa ctacttggct     120
tggtaccagc agaaaccagg gcagtctcct aaactgctga tctactgggc atccactagg    180
gaatctgggg tccctgatcg cttcacaggc agtggatctg gacagatttt cactctcacc    240
atcagcaatg tgcaggctga agacctgaca gtttattact gcaagcaatc ttataatcct    300
ccgtggacgt tcggtggagg caccaagctg gaaatcaaa                           339

<210> SEQ ID NO 23
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gacatagtta tgtcccagtc tccatccagc ttggctgtca gcgccggaga gaaagtgact      60
atgagttgta aatcttccca gtccctgctt aactcacgta ctcggaagaa ttatcttgcc     120
tggtatcaac aaaagccagg tcaaagtcct aagctcctta tttactgggc ctcaacacgg     180
gagtcaggtg tccccgatcg cttcacaggt agtgggagtg gtactgactt cactctcacc     240
atttcaaatg tccaagcaga agacttgact gtgtattact gtaagcagag ttacaaccct     300
ccttggacct ttggtggggg gaccaaactg gagatcaag                            339
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Ser Ser Gln Ser Leu Leu Asn Ser Arg Thr Arg Lys Asn Tyr Leu
1               5                   10                  15

Ala

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Ala Ser Thr Arg Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Gln Ser Tyr Asn Pro Pro Trp Thr
1               5

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Val Gln Gln Ser Gly Pro Glu Leu Val Lys Pro Gly Ala

```
              1               5                  10                 15
         Ser Val Lys Met Ser Cys Lys Ala Ser Gly Tyr Thr Phe Thr Ser Tyr
                         20                  25                 30

Val Met His Trp Val Lys Gln Lys Pro Gly Gln Gly Leu Glu Trp Ile
                         35                  40                 45

Gly Tyr Ile Asn Pro Asn Asn Asp Asn Ile Asn Tyr Asn Glu Lys Phe
                         50                  55                 60

Lys Gly Lys Ala Ser Leu Thr Ser Asp Lys Ser Asn Thr Val Tyr
          65                  70                  75                 80

Met Glu Leu Ser Ser Leu Thr Ser Glu Asp Ser Ala Val Tyr Tyr Cys
                         85                  90                 95

Ala Gly Tyr Gly Asn Ser Gly Ala Asn Trp Gly Gln Gly Thr Leu Val
                         100                 105                110

Thr Val Ser Ala
                 115

<210> SEQ ID NO 28
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gaggtccagg tacagcagtc tggacctgaa ctggtaaagc ctggggcttc agtgaagatg      60
tcctgtaagg cttctggata cacattcact agctatgtca tgcactgggt gaagcagaag    120
cctgggcagg gccttgagtg gattggatat attaatccta caatgataa tattaactac     180 aatgagaagt tcaaaggcaa ggcctcactg acttcagaca atcctccaa cacagtctac     240 atggagctca gcagcctgac ctctgaggac tctgcggtct attactgtgc aggctatggt    300
aactccggag ctaactgggg ccaagggact ctggtcactg tctctgca                 348

<210> SEQ ID NO 29
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gaagttcaag ttcagcaaag cgggcctgag cttgtcaagc caggcgcatc agtcaaaatg      60
agctgtaagg cttccgggta caccttcacc agttatgtca tgcattgggt aaaacaaaag    120
ccaggacagg gactcgagtg gataggatac attaacccaa ataacgacaa cattaactac    180
aacgagaaat tcaagggcaa agcatcattg acttccgata atcctctaa caccgtgtac     240 atggagctga gttcattgac cagcgaggat tctgccgtgt actactgtgc aggttatggc    300
aactctggtg ctaactgggg gcaggggact ctggtcacag tcagcgca                 348

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

Gly Tyr Thr Phe Thr Ser Tyr Val Met His
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ile Asn Pro Asn Asn Asp Asn Ile Asn Tyr Asn Glu Lys Phe Lys
1               5                   10                  15

Gly

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Gly Asn Ser Gly Ala Asn
1               5

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ala Ser Leu Ser Ala Ser Val Gly
1               5                   10                  15

Glu Thr Val Thr Ile Thr Cys Arg Thr Ser Lys Asn Ile Phe Asn Phe
            20                  25                  30

Leu Ala Trp Tyr His Gln Lys Gln Gly Arg Ser Pro Arg Leu Leu Val
        35                  40                  45

Ser His Thr Lys Thr Leu Ala Ala Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ile Tyr Tyr Cys Gln His His Tyr Gly Thr Pro Trp
                85                  90                  95

Thr Phe Gly Gly Gly Thr Lys Leu Glu Ile Lys
            100                 105

<210> SEQ ID NO 34
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gacatccaga tgactcagtc tccagcctcc ctatctgcat ctgtgggaga aactgtcacc      60

```
atcacatgtc gaacaagtaa aaatattttc aattttttag catggtatca ccagaaacag    120
ggaagatctc ctcgactcct ggtctctcat acaaaaacct tagcagcagg tgtgccatca    180
aggttcagtg gcagtggctc aggcacacag ttttctctga agatcaacag cctgcagcct    240
gaagattttg ggatttatta ctgtcaacat cattatggta ctccgtggac gttcggtgga    300
ggcaccaaac tggaaatcaa a                                              321
```

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gacattcaga tgacccagtc accagcatct ttgagcgcat ccgttgggga gactgtgaca    60
atcacatgcc gaaccagtaa gaacatcttc aacttcctcg catggtacca tcaaaagcag    120
ggcaggtctc ccagactgct tgtctctcac accaagacac tggcagcagg cgtccccagc    180
cggtttagtg gtagtggatc tggcacacag tttagtttga aaatcaattc cctgcaaccc    240
gaagacttcg gcatatacta ttgccagcac cactatggga caccttggac tttcggaggt    300
ggtactaaac ttgagattaa a                                              321
```

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Arg Thr Ser Lys Asn Ile Phe Asn Phe Leu Ala
1               5                   10
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
His Thr Lys Thr Leu Ala Ala
1               5
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gln His His Tyr Gly Thr Pro Trp Thr
1               5
```

<210> SEQ ID NO 39
<211> LENGTH: 120
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 39

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
            20                  25                  30
Gly Val Lys Trp Val Lys Gln Ala Pro Gly Lys Asp Leu Lys Trp Met
        35                  40                  45
Gly Trp Ile Asn Thr Tyr Thr Gly Asn Pro Ile Tyr Ala Ala Asp Phe
    50                  55                  60
Lys Gly Arg Phe Ala Phe Ser Leu Glu Thr Ser Ala Ser Thr Ala Phe
65                  70                  75                  80
Leu Gln Ile Asn Asn Leu Lys Asn Glu Asp Thr Ala Thr Tyr Phe Cys
                85                  90                  95
Val Arg Phe Gln Tyr Gly Asp Tyr Arg Tyr Phe Asp Val Trp Gly Ala
            100                 105                 110
Gly Thr Thr Val Thr Val Ser Ser
        115                 120
```

<210> SEQ ID NO 40
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
cagatccagt tggtgcagtc tggacctgag ctgaagaagc ctggagagac agtcaagatc      60
tcctgcaagg cttctgggta taccttcaca aactatggag tgaagtgggt gaagcaggct     120
ccaggaaagg atttaaagtg gatgggctgg ataaacacct acactggaaa tccaatttat     180
gctgctgact caagggacg gtttgccttc tctttggaga cctctgccag cactgccttt      240
ttgcagatca caacctcaa aaatgaggac acggctacat atttctgtgt aagattccaa      300
tatggcgatt accggtactt cgatgtctgg ggcgcaggga ccacggtcac cgtctcctca     360
```

<210> SEQ ID NO 41
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
caaatccaac ttgtccagag cggtcccgag ttgaagaagc tggcgaaac cgtgaaaatc       60
tcatgcaagg ccagtggata tacatttaca aactatggcg tcaagtgggt gaaacaagcc    120
ccaggtaaag acttgaaatg gatgggatgg atcaacacat acacagggaa tcctatctat    180
gcagccgact ttaaaggcag atttgccttc agtttggaga catctgcctc caccgctttc    240
ctgcaaataa ataacctgaa aaatgaagat accgctacat acttctgtgt acggttccag    300
tacggagatt accgctattt cgatgtgtgg ggcgcaggta ccacagtaac cgtctcctca    360
```

<210> SEQ ID NO 42

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Thr Phe Thr Asn Tyr Gly Val Lys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Ile Asn Thr Tyr Thr Gly Asn Pro Ile Tyr Ala Ala Asp Phe Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Gln Tyr Gly Asp Tyr Arg Tyr Phe Asp Val
1               5                   10

<210> SEQ ID NO 45
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Ile Ile Leu Ser Gln Ser Pro Ala Ile Leu Ser Ala Ser Pro Gly
1               5                   10                  15

Glu Lys Val Thr Met Thr Cys Arg Ala Asn Ser Gly Ile Ser Phe Ile
            20                  25                  30

Asn Trp Tyr Gln Gln Lys Pro Gly Ser Ser Pro Lys Pro Trp Ile Tyr
        35                  40                  45

Gly Thr Ala Asn Leu Ala Ser Gly Val Pro Ala Arg Phe Gly Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Arg
            100                 105

<210> SEQ ID NO 46
<211> LENGTH: 318
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 46

```
caaattattc tctcccagtc tccagcaatc ctgtctgcat ctccagggga gaaggtcacg      60
atgacttgca gggccaactc aggtattagt ttcatcaact ggtaccagca gaagccagga    120
tcctccccca aaccctggat ttatggcaca gccaacctgg cttctggagt ccctgctcgc    180
ttcggtggca gtgggtctgg gacttcttac tctctcacaa tcagcagagt ggaggctgaa    240
gacgctgcca cttattactg ccagcagtgg agtagtaacc cgctcacgtt cggtgctggg    300
accaagctgg agttgaga                                                  318
```

<210> SEQ ID NO 47
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
caaataattc tgtcacagtc ccccgctata cttagtgctt caccaggaga aaaagtgacc      60
atgacttgta gagctaattc tggcatatca ttcatcaact ggtatcaaca aaagccaggt    120
tcctccccca agccatggat ttacgggacc gccaaccttg cttctggggt accgctcgt     180
ttcggcggat caggttcagg aacttcctat agcctcacta tcagtcgggt tgaagctgag    240
gatgccgcta catattactg ccagcaatgg tctagtaatc cacttacctt tggagctggc    300
accaaattgg aacttcgt                                                  318
```

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Arg Ala Asn Ser Gly Ile Ser Phe Ile Asn
1               5                   10
```

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Gly Thr Ala Asn Leu Ala Ser
1               5
```

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Trp Ser Ser Asn Pro Leu Thr
1               5

<210> SEQ ID NO 51
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Val Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Ser Asp Val Thr Asn Cys Asn Glu Lys Phe
    50                  55                  60

Lys Gly Lys Ala Thr Leu Thr Ser Asp Lys Thr Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Ser Tyr Gly Gly Gly Phe Ala Tyr Trp Gly Gln Gly Thr Leu Val
            100                 105                 110

Thr Val Ser Ala
        115

<210> SEQ ID NO 52
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gaggtccagc tgcagcagtc tggacctgag ctggtaaagc ctggggcttc agtgaagctg      60
tcctgcaagg cttctggata cacagtcact agctatgtta tgcactgggt gaagcagaag     120
cctgggcagg gccttgagtg gattggatat attaatcctt acagtgatgt tactaactgc     180
aatgagaagt tcaaaggcaa ggccacactg acttcagaca aaacctccag cacagcctac     240
atggagctca gcagcctgac ctctgaggac tctgcggtct attactgttc ctcctacggt     300
gggggttttg cttactgggg ccaagggact ctggtcactg tctctgca                  348

<210> SEQ ID NO 53
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gaagtccagc ttcagcaatc cggcccagaa ctggtaaaac caggcgcaag tgttaagttg      60
agttgcaaag ccagtggtta taccgttact tcatacgtca tgcattgggt aaaacaaaag     120
cccggccaag ggcttgaatg gatcggctac atcaaccctt actctgacgt caccaactgc     180

```
aacgagaaat tcaaaggaa agccacattg acctctgaca agacaagcag taccgcctac    240
atggagcttt ctagtttgac ttctgaagac tctgctgtct actactgtag cagctacggc    300
ggcggctttg cttactgggg ccagggtaca ttggtgactg tgagtgca                 348
```

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Tyr Thr Val Thr Ser Tyr Val Met His
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Ile Asn Pro Tyr Ser Asp Val Thr Asn Cys Asn Glu Lys Phe Lys
1               5                   10                  15

Gly

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Gly Gly Gly Phe Ala Tyr
1               5

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ala Ser Leu Ser Ala Ser Val Gly
1               5                   10                  15

Glu Pro Val Thr Ile Thr Cys Arg Ala Ser Lys Asn Ile Tyr Thr Tyr
            20                  25                  30

Leu Ala Trp Tyr His Gln Lys Gln Gly Lys Ser Pro Gln Phe Leu Val
        35                  40                  45

Tyr Asn Ala Arg Thr Leu Ala Gly Gly Val Pro Ser Arg Leu Ser Gly
    50                  55                  60

Ser Gly Ser Val Thr Gln Phe Ser Leu Asn Ile Asn Thr Leu His Arg
65                  70                  75                  80

Glu Asp Leu Gly Thr Tyr Phe Cys Gln His His Tyr Asp Thr Pro Tyr
                85                  90                  95

Thr Phe Gly Gly Gly Thr Asn Leu Glu Ile Lys
            100                 105

<210> SEQ ID NO 58
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacatccaga tgactcagtc tccagcctcc ctatctgcat ctgtgggaga acctgtcacc      60
atcacatgtc gagcaagtaa gaatatttac acatatttag catggtatca ccagaaacag     120
ggaaaatctc ctcagttcct ggtctataat gcaagaacct tagcaggagg tgtgccatca    180
aggctcagtg gcagtggatc agtcacgcag ttttctctaa acatcaacac cttgcatcga    240
gaagatttag ggacttactt ctgtcaacat cattatgata ctccgtacac gttcggaggg    300
gggaccaacc tggaaataaa a                                               321

<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gacatccaga tgacacagtc accagcatcc ctgtccgcct cagttgggga gcctgttacc      60
ataacttgtc gggcaagcaa aaacatatac acctatttgg cttggtatca ccaaaagcaa    120
ggtaagtcac ctcagtttct tgtatataat gcccgcacac ttgctggcgg agtaccctct    180
cgattgtctg gatctggcag cgttacccaa ttcagcctga acatcaacac cctccatcgg    240
gaagatttgg gtacctattt ctgtcaacat cactacgaca ccccatacac cttcggaggc    300
ggcacaaatt tggaaattaa a                                               321

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Lys Asn Ile Tyr Thr Tyr Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Ala Arg Thr Leu Ala Gly
1               5

<210> SEQ ID NO 62

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln His His Tyr Asp Thr Pro Tyr Thr
1               5

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Ser Asp Val Thr Asn Tyr Asn Glu Lys Phe
    50                  55                  60

Lys Gly Lys Ala Thr Leu Thr Ser Asp Arg Ser Ser Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Asn Tyr Phe Asp Trp Gly Arg Gly Thr Leu Val Thr Val Ser
            100                 105                 110

Ala

<210> SEQ ID NO 64
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gaggtccagc tgcagcagtc tggacctgag ctggtaaagc ctggggcttc agtgaagatg     60
tcctgcaagg cttctggata cacattctct agctatgtta tgcactgggt gaagcagaag    120
cctgggcagg gccttgagtg gattggatat attaatcctt acagtgatgt cactaactac    180
aatgagaagt tcaaaggcaa ggccacactg acttcagaca gatcctccaa cacagcctac    240
atggaactca gcagcctgac ctctgaggac tctgcggtct attactgtgc aagaaattac    300
ttcgactggg gccgagggac tctggtcaca gtctctgca                           339

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gaggtacagc ttcagcagag tggtccagaa ctcgtcaagc ctggggcaag cgttaagatg      60
agttgtaaag catccggtta cacattcagt agctatgtta tgcactgggt caaacagaag     120
cctgggcagg ggttggagtg gatcggatat ataaatccct attcagacgt aactaattat     180
aatgaaaagt tcaaggggaa agcaaccttg acaagtgacc ggtcatctaa taccgcatac     240
atggagctga gctcattgac aagtgaggac tctgctgtgt attactgtgc ccggaactac     300
ttcgactggg gtaggggcac actggtaact gttagtgca                            339
```

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Tyr Thr Phe Ser Ser Tyr Val Met His
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Ile Asn Pro Tyr Ser Asp Val Thr Asn Tyr Asn Glu Lys Phe Lys
1               5                   10                  15

Gly

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Tyr Phe Asp
1

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ala Ser Leu Ser Ala Ser Val Gly
1               5                   10                  15

Glu Thr Val Thr Ile Thr Cys Arg Ala Ser Lys Asn Val Tyr Ser Tyr
            20                  25                  30

Leu Ala Trp Phe Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

```
Gly Gly Ser Gly Thr Gln Phe Ser Leu Lys Ile Asn Ser Leu Gln Pro
65                  70                  75                  80

Ala Asp Phe Gly Ser Tyr Tyr Cys Gln His Tyr Asn Ile Pro Phe
                85                  90                  95

Thr Phe Gly Ser Gly Thr Lys Leu Glu Ile Lys
            100                 105
```

<210> SEQ ID NO 70
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
gacatccaga tgactcagtc tccagcctcc ctatctgcat ctgtgggaga aactgtcacc    60
atcacatgtc gagcaagtaa aaatgtttac agttatttag catggtttca acagaaacag   120
gggaaatctc ctcagctcct ggtctataat gctaaaacct tagcagaagg tgtgccatca   180
aggttcagtg gcgggggatc aggcacacag ttttctctga agatcaacag cctgcagcct   240
gcagattttg ggagttatta ctgtcaacat cattataata ttccattcac gttcggctcg   300
gggacaaagt tggaaataaa a                                             321
```

<210> SEQ ID NO 71
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
gacatacaaa tgacacaaag tcccgctagt ctttcagcca gtgttggtga gactgtgaca    60
ataacctgta gagctagcaa aaatgtctac tcctatctgg cttggttcca gcagaaacaa   120
ggaaagagtc ctcagttgct cgtatataat gctaaaactt tggcagaagg cgtcccttct   180
cgtttcagtg gcggaggaag tgggactcaa ttctcactga agatcaatag cctccagccc   240
gccgactttg ggagctacta ttgccaacat cattacaaca taccattcac ctttggctca   300
ggtactaaac tcgaaattaa a                                             321
```

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Arg Ala Ser Lys Asn Val Tyr Ser Tyr Leu Ala
1               5                   10
```

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asn Ala Lys Thr Leu Ala Glu
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln His His Tyr Asn Ile Pro Phe Thr
1               5

<210> SEQ ID NO 75
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
            20                  25                  30

Pro Met His Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Gly Tyr Asp Gly Ser Arg Glu Phe Ala Tyr Trp Gly Gln
            100                 105                 110

Gly Thr Leu Val Thr Val Ser
        115

<210> SEQ ID NO 76
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
cagatccagt tggtgcagtc tggacctgag ctgaagaagc tggagagaca agtcaagatc      60
tcctgcaagg cttctgggtt taccttcaca aactatccaa tgcactgggt gaagcaggct     120
ccaggaaagg gtttaaagtg gatgggctgg ataaacacct actctggagt gccaacatat     180
gcagatgact caagggacg gtttgccttc tctttggaaa cctctgccag cactgcatat      240
ttgcagatca acaacctcaa aaatgaggac atggctacat atttctgtgc aagagggggc     300
tacgatggta gcagggagtt tgcttactgg ggccaaggga ctctggtcac tgtctct        357

<210> SEQ ID NO 77

<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
cagatacaac tcgtccagtc aggtccagag ttgaagaaac ccggagaaac tgtgaagata      60
tcctgtaaag ccagcggctt tactttcaca aactacccca tgcattgggt gaagcaggcc     120
cccggaaaag gactcaaatg gatgggatgg atcaacacat acagtggggt gcctacttac     180
gcagacgatt tcaaaggaag gttcgcattt agcttggaaa ctagcgcatc tacagcatat     240
ctccagatta acaatcttaa aaatgaggat atggcaacat acttctgcgc tagggaggt      300 tacgatggga gcagggagtt cgcttattgg gggcaaggga ctcttgtgac tgtaagt        357

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Thr Phe Thr Asn Tyr Pro Met His
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Ile Asn Thr Tyr Ser Gly Val Pro Thr Tyr Ala Asp Asp Phe Lys
1               5                   10                  15

Gly

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Tyr Asp Gly Ser Arg Glu Phe Ala Tyr
1               5                   10

<210> SEQ ID NO 81
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Val Leu Thr Gln Ser Pro Ala Ser Leu Ala Ala Ser Leu Gly
1               5                   10                  15

```
Gln Arg Ala Thr Thr Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Thr Phe Gly Gly Gly Thr Lys Leu Glu Ile Lys
            100                 105                 110
```

<210> SEQ ID NO 82
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
gacattgtgc tgacacagtc tcctgcttcc ttagctgcat ctctgggca gagggccacc    60 acctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttaccacg   300
ttcggagggg ggaccaagct ggaaataaaa                                    330
```

<210> SEQ ID NO 83
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
gacatagtgc tcactcagag ccctgcatcc cttgccgcct ccctcggaca acgagctact    60
acaagctacc gggcatcaaa gtccgttagc acatcaggat acagctatat gcactggaat   120
cagcaaaagc caggccaacc accccgtctt ctcatctacc tcgtaagtaa tctggaatca   180
ggcgtgccag cccgattcag tgggtcaggg tctgggacag atttcaccct caacatccat   240
ccagtagagg aagaggacgc agcaacatat tactgccaac acattagaga acttaccact   300
ttcggaggag gaactaaatt ggagatcaaa                                    330
```

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

```
Arg Ala Ser Lys Ser Val Ser Thr Ser Gly Tyr Ser Tyr Met His
1               5                   10                  15
```

```
<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Val Ser Asn Leu Glu Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln His Ile Arg Glu Leu Thr Thr
1               5

<210> SEQ ID NO 87
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 88
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                        245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 90
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Asp Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Phe
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
```

100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 91
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

| | | |
|---|---|---|
| tctaccggac aggtgcagtt ggttcagtct ggcgccgaag tgaagaaacc tggcgcttct | 60 | |
| gtgaaggtgt cctgcaaggc tctggctac acctttacca actacggcgt gaaatgggtc | 120 | |
| cgacaggctc ctggacagga tctggaatgg atgggctgga tcaacaccta caccggcaat | 180 | |
| cctatctacg ccgccgactt caagggcaga gtgaccatga ccaccgacac ctctacctcc | 240 | |
| accgccttca tggaactgcg gtccctgaga tctgacgaca ccgccgtgta ctactgcgtg | 300 | |
| cggtttcagt acggcgacta ccggtacttt gatgtgtggg gccagggcac actggtcacc | 360 | |
| gtttcttccg cttctaccaa gggacccagc gtgttccctc tggctccttc ctctaaatcc | 420 | |
| acctctggcg gaaccgctgc tctgggctgt ctggtcaagg attacttccc tgagcctgtg | 480 | |
| accgtgtcct ggaactctgg tgctctgaca tccggcgtgc acacctttcc agctgtgctg | 540 | |
| cagtcctctg gcctgtactc tctgtcctct gtcgtgaccg tgccttctag ctctctgggc | 600 | |
| acccagacct acatctgcaa cgtgaaccac aagccttcca acaccaaggt ggacaagaag | 660 | |
| gtggaaccca gtcctgcga caagaccac acctgtcctc catgtcctgc tccagaagct | 720 | |
| gctggcgctc cctctgtgtt cctgtttcct ccaaagccta aggacaccct gatgatctct | 780 | |
| cggacccctg aagtgacctg cgtggtggtg gatgtgtctc acgaggaccc agaagtgaag | 840 | |
| ttcaattggt acgtggacgg cgtggaagtg cacaacgcca agaccaagcc tagagaggaa | 900 | |
| cagtacaact ccacctacag agtggtgtcc gtgctgaccg tgctgcacca ggattggctg | 960 | |
| aacggcaaag agtacaagtg caaggtgtcc aacaaggcac tgcccgctcc tatcgaaaag | 1020 | |
| accatctcca aggctaaggg ccagcctcgg gaacctcagg tttacaccct gcctccatct | 1080 | |
| cgggaagaga tgaccaagaa ccaggtgtcc ctgacctgcc tcgtgaaggg cttctacccc | 1140 | |
| tccgatatcg ccgtggaatg ggagtccaat ggccagcctg agaacaacta agacaacc | 1200 | |
| cctcctgtgc tggactccga cggctcattc ttcctgtact ccaagctgac agtggacaag | 1260 | |
| tctcggtggc agcagggcaa cgtgttctcc tgttctgtga tgcacgaggc cctgcacaac | 1320 | |
| cactacacac agaagtccct gtctctgtcc cctggcaagt ga | 1362 | |

```
<210> SEQ ID NO 92
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser Ala Ser Thr Lys Gly Pro Ser Val
```

```
            115                 120                 125
Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 93
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gaagtgcagt tggtgcagtc tggcgccgaa gtgaagaaac tggcgcttc tgtgaaggtg      60 tcctgcaagg cctctggcta caccttacc aactacggcg tgaaatgggt ccgacaggct     120
```

```
cctggacaag gcctggaatg gatgggctgg atcaacacct acaccggcaa tcctatctac    180
gccgccgact tcaagggcag agtgaccatg accaccgaca cctctacctc caccgcctac    240
atggaactgc ggtccctgag atctgacgac accgccgtgt actactgcgt gcggtttcag    300
tacggcgact accggtactt tgatgtgtgg ggccagggca cactggtcac cgtttcttcc    360
gcttctacca agggacccag cgtgttccct ctggctcctt cctctaaatc cacctctggc    420
ggaaccgctg ctctgggctg tctggtcaag gattacttcc ctgagcctgt gaccgtgtcc    480
tggaattctg gtgctctgac atccggcgtg cacacctttc cagctgtgct gcagtcctct    540
ggcctgtact ctctgtcctc tgtcgtgacc gtgccttcta gctctctggg cacccagacc    600
tacatctgca acgtgaacca caagccttcc aacaccaagg tggacaagaa ggtggaaccc    660
aagtcctgcg acaagaccca cacctgtcct ccatgtcctg ctccagaagc tgctggcgct    720
ccctctgtgt tcctgtttcc tccaaagcct aaggacaccc tgatgatctc tcggacccct    780
gaagtgacct gcgtggtggt ggatgtgtct cacgaggacc cagaagtgaa gttcaattgg    840
tacgtggacg gcgtggaagt gcacaacgcc aagaccaagc ctagagagga acagtacaac    900
tccacctaca gtggtgtc cgtgctgacc gtgctgcacc aggattggct gaacggcaaa    960
gagtacaagt gcaaggtgtc caacaaggca ctgcccgctc tatcgaaaa gaccatctcc    1020 aaggctaagg gccagcctcg ggaacctcag gtttacaccc tgcctccatc tcgggaagag    1080
atgaccaaga accaggtgtc cctgacctgc ctcgtgaagg gcttctaccc ttccgatatc    1140
gccgtggaat gggagtccaa tggccagcct gagaacaact acaagacaac ccctcctgtg    1200
ctggactccg acggctcatt cttcctgtac tccaagctga cagtggacaa gtctcggtgg    1260
cagcagggca acgtgttctc ctgttctgtg atgcacgagg ccctgcacaa ccactacaca    1320
cagaagtccc tgtctctgtc ccctggcaag tga                                 1353
```

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Tyr Thr Phe Thr Asn Tyr Gly Val Lys
1               5                   10

<210> SEQ ID NO 95
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Ile Asn Thr Tyr Thr Gly Asn Pro Ile Tyr Ala Ala Asp Phe Lys
1               5                   10                  15

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Phe Gln Tyr Gly Asp Tyr Arg Tyr Phe Asp Val
1               5                   10

<210> SEQ ID NO 97
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Ile Ile Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Gly Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 98
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
aagcttgcca ccatggaaac cgacacactg ctgctgtggg tgctgttgtt gtgggtgcca      60
ggatctaccg gagagatcat cctgacacag agccccgcca cattgtctct gagtcctggc     120
gagagagcta ccctgtcctg tagagccaac tccggcatct ccttcatcaa ctggtatcag     180
cagaagcccg gccaggctcc tagactgctg atctatggca ccgctaacct ggcctctggc     240
atccctgcta gatttggcgg ctctggctct ggcagagact tcaccctgac catctctagc     300

```
ctggaacctg aggacttcgc cgtgtactac tgccagcagt ggtctagcaa ccctctgacc      360
tttggcggag gcaccaaggt ggaaatcaag agaaccgtgg ccgctccttc cgtgttcatc      420
ttcccaccat ctgacgagca gctgaagtct ggcacagcct ctgtcgtgtg cctgctgaac      480
aacttctacc ctcgggaagc caaggtgcag tggaaggtgg acaatgccct gcagtccggc      540
aactcccaag agtctgtgac cgagcaggac tccaaggact ctacctacag cctgtcctcc      600
acactgaccc tgtctaaggc cgactacgag aagcacaagg tgtacgcctg tgaagtgacc      660
caccagggac tgtctagccc cgtgaccaag tctttcaacc ggggcgagtg ctga           714
```

<210> SEQ ID NO 99
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 100
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
tctacaggcg agatcgtgct gacccagtct cctgccacat tgtctctgag tcctggcgag    60
agagctaccc tgtcctgtag agccaactcc ggcatctcct tcatcaactg gtatcagcag   120
aagcccggcc aggctcctag actgctgatc tatggcaccg ctaacctggc ctctggcatc   180
cctgctagat tttccggctc tggctctggc agagacttca ccctgaccat ctctagcctg   240
gaacctgagg acttcgccgt gtactactgc cagcagtggt ctagcaaccc tctgaccttt   300
ggcggaggca ccaaggtgga aatcaagaga accgtggccg ctccttccgt gttcatcttc   360
ccaccatctg acgagcagct gaagtctggc acagcctctg tcgtgtgcct gctgaacaac   420
ttctaccctc gggaagccaa ggtgcagtgg aaggtggaca atgccctgca gtccggcaac   480
tcccaagagt ctgtgaccga gcaggactcc aaggactcta cctacagcct gtcctccaca   540
ctgaccctgt ctaaggccga ctacgagaag cacaaggtgt acgcctgtga agtgacccac   600
cagggactgt ctagccccgt gaccaagtct ttcaaccggg gcgagtgctg a            651
```

<210> SEQ ID NO 101
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Glu Ile Val Leu Thr Gln Ser Pro Ala Thr Leu Ser Leu Ser Pro Gly
1               5                   10                  15

Glu Arg Ala Thr Leu Ser Cys Arg Ala Gln Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 102
<211> LENGTH: 651
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 102

```
tctacaggcg agatcgtgct gacccagtct cctgccacat tgtctctgag tcctggcgag    60
agagctaccc tgtcttgtag agcccagtcc ggcatctcct tcatcaactg gtatcagcag   120
aagcccggcc aggctcctag actgctgatc tatggcaccg ctaacctggc ctctggcatc   180
cctgctagat tttccggctc tggctctggc agagacttca ccctgaccat ctctagcctg   240
gaacctgagg acttcgccgt gtactactgc cagcagtggt ctagcaaccc tctgaccttt   300
ggcggaggca ccaaggtgga aatcaagaga accgtggccg ctccttccgt gttcatcttc   360
ccaccatctg acgagcagct gaagtctggc acagcctctg tcgtgtgcct gctgaacaac   420
ttctaccctc gggaagccaa ggtgcagtgg aaggtggaca atgccctgca gtctggcaac   480
tcccaagagt ctgtgaccga gcaggactcc aaggactcta cctacagcct gtcctccaca   540
ctgaccctgt ctaaggccga ctacgagaag cacaaggtgt acgcctgtga agtgacccac   600
cagggactgt ctagccccgt gaccaagtct ttcaaccggg gcgagtgctg a             651
```

<210> SEQ ID NO 103
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Tyr Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 104
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
tctacaggcg agatcgtgct gacccagtct cctgccacat tgtctctgag tcctggcgag      60
agagctaccc tgtcctgtag agccaactcc ggcatctcct tcatcaactg gtatcagcag     120
aagcccggcc aggctcctag actgctgatc tatggcaccg ctaacctggc ctctggcatc     180
cctgctagat tttccggctc tggctctggc agagacttca ccctgaccat ctctagcctg     240
gaacctgagg acttcgccgt gtactactgc cagcagtaca gcagcaaccc tctgaccttt     300
ggcggaggca ccaaggtgga aatcaagaga accgtggccg ctccttccgt gttcatcttc     360
ccaccatctg acgagcagct gaagtctggc acagcctctg tcgtgtgcct gctgaacaac     420
ttctaccctc gggaagccaa ggtgcagtgg aaggtggaca atgccctgca gtccggcaac     480
tcccaagagt ctgtgaccga gcaggactcc aaggactcta cctacagcct gtcctccaca     540
ctgaccctgt ctaaggccga ctacgagaag cacaaggtgt acgcctgtga agtgacccac     600
cagggactgt ctagccccgt gaccaagtct ttcaaccggg gcgagtgctg a              651

<210> SEQ ID NO 105
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Gln Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Tyr Ser Ser Asn Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 106
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
tctacaggcg agatcgtgct gacccagtct cctgccacat tgtctctgag tcctggcgag      60
agagctaccc tgtcttgtag agcccagtcc ggcatctcct tcatcaactg gtatcagcag     120
aagcccggcc aggctcctag actgctgatc tatggcaccg ctaacctggc ctctggcatc     180
cctgctagat tttccggctc tggctctggc agagacttca ccctgaccat ctctagcctg     240
gaacctgagg acttcgccgt gtactactgc cagcagtaca gcagcaaccc tctgaccttt     300
ggcggaggca ccaaggtgga aatcaagaga accgtggccg ctccttccgt gttcatcttc     360
ccaccatctg acgagcagct gaagtctggc acagcctctg tcgtgtgcct gctgaacaac     420
ttctaccctc gggaagccaa ggtgcagtgg aaggtggaca atgccctgca gtctggcaac     480
tcccaagagt ctgtgaccga gcaggactcc aaggactcta cctacagcct gtcctccaca     540
ctgaccctgt ctaaggccga ctacgagaag cacaaggtgt acgcctgtga agtgacccac     600
cagggactgt ctagccccgt gaccaagtct ttcaaccggg gcgagtgctg a               651

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala Asn Ser Gly Ile Ser Phe Ile Asn
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Gln Ser Gly Ile Ser Phe Ile Asn
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Thr Ala Asn Leu Ala Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Trp Ser Ser Asn Pro Leu Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Tyr Ser Ser Asn Pro Leu Thr
1               5

<210> SEQ ID NO 112
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Thr Ile Ser Ser Gly Ser Ile Tyr Ile Tyr Tyr Thr Asp Gly Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ile Tyr Tyr Gly Tyr Asp Gly Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val

-continued

```
                180                 185                 190
Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
        210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 113
<211> LENGTH: 1362
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

```
gaggtgcagc tggttgaatc tggcggagga cttgtgaagc ctggcggctc tctgagactg    60
tcttgtgccg cctctggctt caccttctcc agctttgcca tgtcctgggt ccgacaggct   120
cctggcaaag gactggaatg ggtgtccacc atctcctccg gctccatcta catctactac   180
accgacggcg tgaagggcag attcaccatc agcagagaca cgccaagaa ctccctgtac   240
ctgcagatga acagcctgag agccgaggac accgccgtgt actattgtgc cagacggggc   300
atctactatg ctacgacgg ctacgctatg gactattggg gacagggcac actggtcacc   360
gtgtcctctg cttctaccaa gggacccagc gtgttccctc tggctccttc ctctaaatcc   420
acctctggcg gaaccgctgc tctgggctgt ctggtcaagg attacttccc tgagcctgtg   480
```

```
accgtgtcct ggaactctgg tgctctgaca tccggcgtgc acacctttcc agctgtgctg    540
cagtcctctg gcctgtactc tctgtcctct gtcgtgaccg tgccttctag ctctctgggc    600
acccagacct acatctgcaa cgtgaaccac aagccttcca acaccaaggt ggacaagaag    660
gtggaaccca gtcctgcga caagacccac acctgtcctc catgtcctgc tccagaagct    720
gctggcgctc cctctgtgtt cctgtttcct ccaaagccta aggacaccct gatgatctct    780
cggacccctg aagtgacctg cgtggtggtg gatgtgtctc acgaggaccc agaagtgaag    840
ttcaattggt acgtggacgg cgtggaagtg cacaacgcca agaccaagcc tagagaggaa    900
cagtacaact ccacctacag agtggtgtcc gtgctgaccg tgctgcacca ggattggctg    960
aacggcaaag agtacaagtg caaggtgtcc aacaaggcac tgcccgctcc tatcgaaaag   1020
accatctcca aggctaaggg ccagcctcgg aacctcagg tttacaccct gcctccatct    1080
cgggaagaga tgaccaagaa ccaggtgtcc ctgacctgcc tcgtgaaggg cttctaccct   1140
tccgatatcg ccgtggaatg ggagtccaat ggccagcctg agaacaacta caagacaacc   1200
cctcctgtgc tggactccga cggctcattc ttcctgtact ccaagctgac agtggacaag   1260
tctcggtggc agcagggcaa cgtgttctcc tgttctgtga tgcacgaggc cctgcacaac   1320
cactacacac agaagtccct gtctctgtcc cctggcaagt ga                      1362
```

<210> SEQ ID NO 114
<211> LENGTH: 453
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 114

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Thr Ile Ser Ser Gly Ser Ile Tyr Ile Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ile Tyr Tyr Gly Tyr Glu Gly Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
```

-continued

```
                195                 200                 205
Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Thr Phe Ser Ser Phe Ala Met Ser
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Ile Ser Ser Gly Ser Ile Tyr Ile Tyr Tyr Thr Asp Gly Val Lys
1               5                   10                  15

Gly
```

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Ile Ser Ser Gly Ser Ile Tyr Ile Tyr Tyr Thr Asp Ser Val Lys
1               5                   10                  15
Gly

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Gly Ile Tyr Tyr Gly Tyr Asp Gly Tyr Ala Met Asp Tyr
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Gly Ile Tyr Tyr Gly Tyr Glu Gly Tyr Ala Met Asp Tyr
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Gly Ile Tyr Tyr Gly Tyr Ser Gly Tyr Ala Met Asp Tyr
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Gly Ile Tyr Tyr Gly Tyr Ala Gly Tyr Ala Met Asp Tyr
1               5                   10

<210> SEQ ID NO 122
<211> LENGTH: 219
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 122

```
Ala Ile Val Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Met Gln Lys Pro Gly Gln Ala
        35                  40                  45

Pro Arg Val Leu Ile Tyr Lys Val Ser Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Asp Asp Phe Ala Ile Tyr Tyr Cys Ser Gln Ser
                85                  90                  95

Thr His Ile Pro Leu Ala Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 123
<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 123

```
gccatcgtgt tgacccagtc tccaggcaca ttgtctctga gccctggcga gagagctacc      60
ctgtcctgca gatcttctca gtccctggtg cactccaacg gcaacaccta cctgcactgg     120
tacatgcaga gcccggaca ggctcccaga gtgctgatct acaaggtgtc caaccggttc      180
tctggcatcc ccgacagatt ttccggctct ggctctggca ccgacttcac cctgaccatc     240
tctagactgg aacccgacga cttcgccatc tactactgct cccagtccac acacatccct     300
ctggcttttg gccagggcac caagctggaa atcaagagaa ccgtggccgc tccttccgtg     360
ttcatcttcc caccatctga cgagcagctg aagtccggca cagcttctgt cgtgtgcctg     420
ctgaacaact ctaccctcg ggaagccaag gtgcagtgga aggtggacaa tgccctgcag      480
tccggcaact cccaagagtc tgtgaccgag caggactcca aggactctac ctacagcctg     540
tcctccacac tgaccctgtc taaggccgac tacgagaagc acaaggtgta cgcctgtgaa     600
gtgacccacc agggcctgtc tagccctgtg accaagtctt tcaaccgggg cgagtgttga     660
```

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Arg Ser Ser Gln Ser Leu Val His Ser Asn Gly Asn Thr Tyr Leu His
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Arg Ser Ser Gln Ser Leu Val His Ser Ser Gly Asn Thr Tyr Leu His
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Arg Ser Ser Gln Ser Leu Val His Ser Thr Gly Asn Thr Tyr Leu His
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Arg Ser Ser Gln Ser Leu Val His Ser Gln Gly Asn Thr Tyr Leu His
1               5                   10                  15

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Lys Val Ser Asn Arg Phe Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Ser Gln Ser Thr His Ile Pro Leu Ala
1               5

<210> SEQ ID NO 130
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Lys Trp Val Arg Gln Ala Pro Gly Gln Gly Leu Glu Trp Met
        35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser
        115                 120

<210> SEQ ID NO 131
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Ile Val Leu Thr Gln Ser Pro Ala Thr Leu Ser Leu Ser Pro Gly
1               5                   10                  15

Glu Arg Ala Thr Leu Ser Cys Arg Ala Gln Ser Gly Ile Ser Phe Ile
            20                  25                  30

Asn Trp Tyr Gln Gln Lys Pro Gly Gln Ala Pro Arg Leu Leu Ile Tyr
        35                  40                  45

Gly Thr Ala Asn Leu Ala Ser Gly Ile Pro Ala Arg Phe Ser Gly Ser
    50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 132
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 132

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn Tyr
                20                  25                  30

Gly Val Lys Trp Val Arg Gln Ala Pro Gly Gln Asp Leu Glu Trp Met
            35                  40                  45

Gly Trp Ile Asn Thr Tyr Thr Gly Asn Pro Ile Tyr Ala Ala Asp Phe
    50                  55                  60

Lys Gly Arg Val Thr Met Thr Thr Asp Thr Ser Thr Ser Thr Ala Phe
65                  70                  75                  80

Met Glu Leu Arg Ser Leu Arg Ser Asp Asp Thr Ala Val Tyr Tyr Cys
                85                  90                  95

Val Arg Phe Gln Tyr Gly Asp Tyr Arg Tyr Phe Asp Val Trp Gly Gln
            100                 105                 110

Gly Thr Leu Val Thr Val Ser Ser
        115                 120

<210> SEQ ID NO 133
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Ile Ile Leu Thr Gln Ser Pro Ala Thr Leu Ser Leu Ser Pro Gly
1               5                   10                  15

Glu Arg Ala Thr Leu Ser Cys Arg Ala Asn Ser Gly Ile Ser Phe Ile
                20                  25                  30

Asn Trp Tyr Gln Gln Lys Pro Gly Gln Ala Pro Arg Leu Leu Ile Tyr
            35                  40                  45

Gly Thr Ala Asn Leu Ala Ser Gly Ile Pro Ala Arg Phe Gly Gly Ser
        50                  55                  60

Gly Ser Gly Arg Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 134
<211> LENGTH: 202
<212> TYPE: PRT
<213> ORGANISM: Homo sapiens

<400> SEQUENCE: 134

Met Cys Tyr Gly Lys Cys Ala Arg Cys Ile Gly His Ser Leu Val Gly
1               5                   10                  15

Leu Ala Leu Leu Cys Ile Ala Ala Asn Ile Leu Leu Tyr Phe Pro Asn
                20                  25                  30

Gly Glu Thr Lys Tyr Ala Ser Glu Asn His Leu Ser Arg Phe Val Trp
            35                  40                  45

Phe Phe Ser Gly Ile Val Gly Gly Gly Leu Leu Met Leu Leu Pro Ala

```
                 50                  55                  60
Phe Val Phe Ile Gly Leu Glu Gln Asp Asp Cys Cys Gly Cys Cys Gly
 65                  70                  75                  80

His Glu Asn Cys Gly Lys Arg Cys Ala Met Leu Ser Ser Val Leu Ala
                 85                  90                  95

Ala Leu Ile Gly Ile Ala Gly Ser Gly Tyr Cys Val Ile Val Ala Ala
                100                 105                 110

Leu Gly Leu Ala Glu Gly Pro Leu Cys Leu Asp Ser Leu Gly Gln Trp
                115                 120                 125

Asn Tyr Thr Phe Ala Ser Thr Glu Gly Gln Tyr Leu Leu Asp Thr Ser
                130                 135                 140

Thr Trp Ser Glu Cys Thr Glu Pro Lys His Ile Val Glu Trp Asn Val
145                 150                 155                 160

Ser Leu Phe Ser Ile Leu Leu Ala Leu Gly Gly Ile Glu Phe Ile Leu
                165                 170                 175

Cys Leu Ile Gln Val Ile Asn Gly Val Leu Gly Gly Ile Cys Gly Phe
                180                 185                 190

Cys Cys Ser His Gln Gln Gln Tyr Asp Cys
                195                 200

<210> SEQ ID NO 135
<211> LENGTH: 48
<212> TYPE: PRT
<213> ORGANISM: Homo sapiens

<400> SEQUENCE: 135

Glu Gly Pro Leu Cys Leu Asp Ser Leu Gly Gln Trp Asn Tyr Thr Phe
 1               5                  10                  15

Ala Ser Thr Glu Gly Gln Tyr Leu Leu Asp Thr Ser Trp Ser Glu
                20                  25                  30

Cys Thr Glu Pro Lys His Ile Val Glu Trp Asn Val Ser Leu Phe Ser
                35                  40                  45
```